(12) United States Patent
Goto

(10) Patent No.: US 9,783,481 B2
(45) Date of Patent: *Oct. 10, 2017

(54) CARBONYL DERIVATIVE, LIQUID CRYSTAL COMPOSITION CONTAINING COMPOUND THEREOF AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Mayumi Goto, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/615,159

(22) Filed: Feb. 5, 2015

(65) Prior Publication Data
US 2015/0218452 A1 Aug. 6, 2015

(30) Foreign Application Priority Data
Feb. 5, 2014 (JP) .................................. 2014-20186

(51) Int. Cl.
| | | |
|---|---|---|
| *G02F 1/13* | (2006.01) | |
| *C07C 62/38* | (2006.01) | |
| *C09K 19/30* | (2006.01) | |
| *C07C 49/84* | (2006.01) | |
| *C07C 49/80* | (2006.01) | |
| *C07D 309/06* | (2006.01) | |
| *C07D 493/08* | (2006.01) | |
| *C07D 319/06* | (2006.01) | |
| *C09K 19/06* | (2006.01) | |
| *C09K 19/14* | (2006.01) | |
| *C09K 19/32* | (2006.01) | |
| *C09K 19/34* | (2006.01) | |
| *C09K 19/04* | (2006.01) | |

(52) U.S. Cl.
CPC .............. *C07C 62/38* (2013.01); *C07C 49/80* (2013.01); *C07C 49/84* (2013.01); *C07D 309/06* (2013.01); *C07D 319/06* (2013.01); *C07D 493/08* (2013.01); *C09K 19/062* (2013.01); *C09K 19/14* (2013.01); *C09K 19/3003* (2013.01); *C09K 19/3028* (2013.01); *C09K 19/3066* (2013.01); *C09K 19/32* (2013.01); *C09K 19/322* (2013.01); *C07C 2101/14* (2013.01); *C09K 2019/0425* (2013.01); *C09K 2019/0444* (2013.01); *C09K 2019/3422* (2013.01); *C09K 2019/3425* (2013.01)

(58) Field of Classification Search
CPC ...................................................... C09K 19/062
See application file for complete search history.

(56) References Cited

U.S. PATENT DOCUMENTS

| | | | |
|---|---|---|---|
| 6,576,303 B1 | 6/2003 | Tamura et al. | |
| 2005/0007541 A1* | 1/2005 | Sasada | ............... C09K 19/0403 349/183 |
| 2007/0200092 A1* | 8/2007 | Matsui | .................... C07C 25/18 252/299.01 |

FOREIGN PATENT DOCUMENTS

| | | |
|---|---|---|
| EP | 1731493 A1 | 12/2006 |
| WO | 2000-039063 A | 7/2000 |
| WO | 2005-095311 A | 10/2005 |

* cited by examiner

*Primary Examiner* — Chanceity Robinson
(74) *Attorney, Agent, or Firm* — Hogan Lovells US LLP

(57) ABSTRACT

To provide a liquid crystal compound satisfying at least one of physical properties such as a high stability to heat, light and so forth, a high clearing point, a low minimum temperature of a liquid crystal phase, a small viscosity, a suitable optical anisotropy, a large dielectric anisotropy, a suitable elastic constant and an excellent compatibility with other liquid crystal compounds; a liquid crystal composition containing the compound; and a liquid crystal display device including the composition. The compound is represented by formula (1):

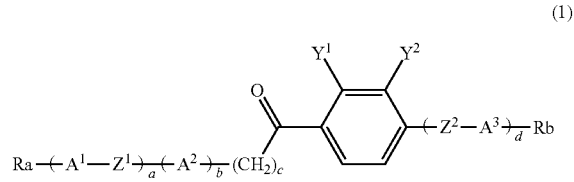

(1)

wherein, for example, Ra and Rb are alkyl having 1 to 10 carbons, alkenyl having 2 to 10 carbons or alkoxy having 1 to 9 carbons; $A^1$, $A^2$ and $A^3$ are 1,4-cyclohexylene or 1,4-phenylene; $Z^1$ and $Z^2$ are single bonds, $-(CH_2)_2-$, $-CH=CH-$, $-COO-$, $-OCO-$, $-CF_2O-$, $-OCF_2-$, $-CH_2O-$ or $-OCH_2-$; $Y^1$ is $-CF_2H$ or $-CF_3$; $Y^2$ is fluorine; and a, b and d are 0, 1, 2 or 3, and c is 1 or 3.

11 Claims, No Drawings

CARBONYL DERIVATIVE, LIQUID CRYSTAL COMPOSITION CONTAINING COMPOUND THEREOF AND LIQUID CRYSTAL DISPLAY DEVICE

TECHNICAL FIELD

The invention relates to a liquid crystal compound being a carbonyl derivative, a liquid crystal composition and a liquid crystal display device. More specifically, the invention relates to a compound that has an alkyloxy or alkyleneoxy skeleton and has a negative dielectric anisotropy, a liquid crystal composition containing the compound, and a liquid crystal display device including the composition.

BACKGROUND ART

A liquid crystal display device is widely utilized for a display of a personal computer, a television and so forth. The device utilizes optical anisotropy, dielectric anisotropy and so forth of a liquid crystal compound. As an operating mode of the liquid crystal display device, various modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

Among the modes, the IPS mode, the FFS mode and the VA mode are known to improve narrowness of a viewing angle being a disadvantage of the operating mode such as the TN mode and the STN mode. In the liquid crystal display device having the mode of the kind, a liquid crystal composition having a negative dielectric anisotropy is mainly used. In order to further improve characteristics of the liquid crystal display device, the liquid crystal compound contained in the composition preferably has physical properties described in (1) to (8) below:

(1) high stability to heat, light and so forth;
(2) high clearing point;
(3) low minimum temperature of a liquid crystal phase;
(4) small viscosity ($\eta$);
(5) suitable optical anisotropy ($\Delta n$);
(6) large negative dielectric anisotropy ($\Delta \in$);
(7) suitable elastic constant ($K_{33}$: bend elastic constant); and
(8) excellent compatibility with other liquid crystal compounds.

An effect of the physical properties of the liquid crystal compound on the characteristics of the device is as described below. A compound having a high stability to heat, light and so forth as described in (1) increases a voltage holding ratio of the device. Thus, a service life of the device becomes long. A compound having a high clearing point as described in (2) extends a temperature range in which the device can be used. A compound having a low minimum temperature of the liquid crystal phase such as a nematic phase and a smectic phase, as described in (3), in particular, a compound having a low minimum temperature of the nematic phase, also extends a temperature range in which the device can be used. A compound having a small viscosity as described in (4) shortens a response time of the device.

A compound having a suitable optical anisotropy as described in (5) improves a contrast of the device. According to a design of the device, a compound having a large optical anisotropy or a small optical anisotropy, more specifically, a compound having a suitable optical anisotropy, is required. When the response time is shortened by decreasing a cell gap of the device, a compound having a large optical anisotropy is suitable. A compound having a large negative dielectric anisotropy as described in (6) decreases a threshold voltage of the device. Thus, an electric power consumption of the device is decreased.

With regard to (7), a compound having a large elastic constant decreases the response time of the device. A compound having a small elastic constant decreases the threshold voltage of the device. Therefore, a suitable elastic constant is required according to characteristics to be desirably improved. A compound having an excellent compatibility with other liquid crystal compounds as described in (8) is preferred. The reason is that physical properties of the composition are adjusted by mixing liquid crystal compounds having different physical properties.

As a component of the liquid crystal composition having the negative dielectric anisotropy ($\Delta \in$), study has been conducted so far on many liquid crystal compounds in which hydrogen in a lateral position on a benzene ring is replaced by fluorine. For example, compounds (a) and (b) have been reported. However, while compounds (a), (b) and (c) have negative dielectric anisotropy ($\Delta \in$), values thereof is not always large in several cases, and may be insufficient in the order to reduce a driving voltage of the liquid crystal display device having the modes such as the VA mode and the IPS mode in several cases.

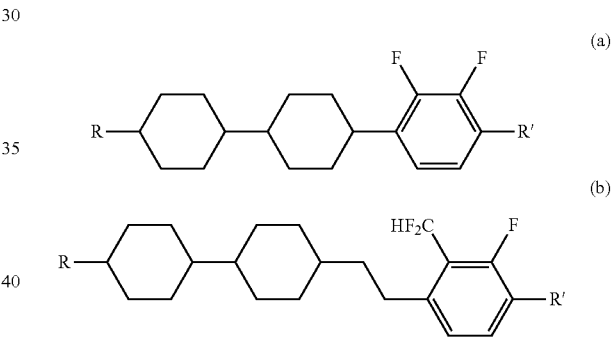

From such a circumstance, development has been desired for a compound having excellent physical properties and a suitable balance with regard to the physical properties (1) to (8) described above. In particular, the compound having the large negative dielectric anisotropy has been required.

CITATION LIST

Patent Literature

Patent literature No. 1: WO 2000/039063 A.
Patent literature No. 2: WO 2005/095311 A.

SUMMARY OF INVENTION

Technical Problem

A first object of the invention is to provide a liquid crystal compound satisfying at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. The object is to provide a compound having a particularly large negative dielectric anisotropy. A second object is to provide a liquid crystal composition that contains the compound and satisfies at least one of physical properties such as a high maximum temperature of a nematic phase, a low minimum temperature of the nematic phase, a small viscosity, a suitable optical anisotropy, a large negative dielectric anisotropy and a suitable elastic constant. The object is to provide a liquid crystal composition having a suitable balance regarding at least two of the physical properties. A third object is to provide a liquid crystal display device that includes the composition and has a wide temperature range in which the device can be used, a short response time, a large voltage holding ratio, a low threshold voltage, a large contrast ratio and a long service life.

Solution to Problem

The invention concerns to a compound represented by formula (1), a liquid crystal composition containing the compound, and a liquid crystal display device including the composition. The compound represented by formula (1) is:

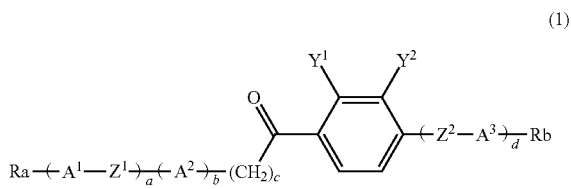

(1)

wherein, in formula (1),

Ra and Rb are independently hydrogen, halogen or alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—, and in the groups, at least one of hydrogen may be replaced by fluorine;

$A^1$, $A^2$ and $A^3$ are independently 1,4-cyclohexylene, 1,4-phenylene, cyclohexene-1,4-diyl, 2,6,7-trioxabicyclo[2.2.2]octane-1,4-diyl, decahydronaphthalene-2,6-diyl, 1,2,3,4-tetrahydronaphthalene-2,6-diyl or naphthalene-2,6-diyl, and in the groups, one of —$CH_2$— may be replaced by —O—, —S—, —CO— or —$SiH_2$—, and at least one of —$(CH_2)_2$— may be replaced by —CH=CH— or —CH=N—, and in the groups, at least one of hydrogen may be replaced by halogen, —C≡N, —$CF_3$, —$CHF_2$, —$CH_2F$, —$OCF_3$, —$OCHF_2$ or —$OCH_2F$;

$Z^1$ and $Z^2$ are independently a single bond or alkylene having 1 to 4 carbons, and in the alkylene, at least one of —$CH_2$— may be replaced by —O—, —S—, —CO— or —$SiH_2$—, and at least one of —$(CH_2)_2$— may be replaced by —CH=CH— or —C≡C—, and in the groups, at least one of hydrogen may be replaced by halogen;

$Y^1$ is —$CF_2H$ or —$CF_3$, and $Y^2$ is hydrogen, halogen, —$CFH_2$, —$CF_2H$ or —$CF_3$;

a, b and d each are 0, 1, 2 or 3, and a sum of a, b and d is 4 or less, and when a, b or d is 2 or more, two of ring $A^1$ selected from two or more of ring $A^1$, two of ring $A^2$ selected from two or more of ring $A^2$, two of ring $A^3$ selected from two or more of ring $A^3$, two of $Z^1$ selected from two or more of $Z^1$, or two of $Z^2$ selected from two or more of $Z^2$ may be identical or different; and c is 0, 1, 2, 3, 4, 5, 6, 7, 8, 9 or 10.

Advantageous Effects of Invention

A first advantage of the invention is to provide a liquid crystal compound satisfying at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. The advantage is to provide a compound having a particularly large negative dielectric anisotropy. A second advantage is to provide a liquid crystal composition that contains the compound and satisfies at least one of physical properties such as a high maximum temperature of a nematic phase, a low minimum temperature of the nematic phase, a small viscosity, a suitable optical anisotropy, a large negative dielectric anisotropy and a suitable elastic constant. The advantage is to provide a liquid crystal composition having a suitable balance regarding at least two of the physical properties. A third advantage is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase or a smectic phase, and also for a compound having no liquid crystal phases but being useful as a component for a liquid crystal composition. The liquid crystal compound, the liquid crystal composition and a liquid crystal display device may be occasionally abbreviated as "compound," "composition" and "device," respectively. The liquid crystal display device is a generic term for a liquid crystal display panel and a liquid crystal display module. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as a maximum temperature. A minimum temperature of the nematic phase may be occasionally abbreviated as a minimum temperature. "Compound represented by formula (1)" may be occasionally abbreviated as "compound (1)." A composition containing the compound represented by formula (1) may be occasionally abbreviated as composition (1). The abbreviation may also apply to a compound represented by formula (2) or the like. In formula (1), formula (2) or the like, a symbol $A^1$, $D^1$ or the like surrounded by a hexagonal shape corresponds to ring $A^1$, ring $D^1$ or the like, respectively. A plurality of ring $A^1$ are described in one formula or different formulas. In the compounds, two groups represented by arbitrary two of ring $A^1$ may be identical or different. The rule is also applied to a symbol ring $A^2$, $Z^2$ or the like. Moreover, the rule is also applied to two of ring $A^1$ when 1 is 2. An amount of the compound expressed in terms of "percent" is expressed in terms of "weight percent (% by weight)" based on the total weight of the composition.

An expression "at least one of "A" may be replaced by "B"" means that a position of "A" is arbitrary when the number of "A" is 1, and also when the number of "A" is two or more, positions thereof can be selected without limitation. An expression "at least one of A may be replaced by B, C or D" means inclusion of a case where arbitrary A is replaced by B, a case where arbitrary A is replaced by C, and a case where arbitrary A is replaced by D, and also a case where a plurality of A are replaced by at least two of B, C or D. For example, alkyl in which at least one of —CH$_2$— may be replaced by —O— or —CH=CH— includes alkyl, alkenyl, alkoxy, alkoxyalkyl, alkoxyalkenyl and alkenyloxyalkyl. In addition, replacement of two successive —CH$_2$— by —O— to form —O—O— is not preferred. In alkyl or the like, replacement of —CH$_2$— of a methyl part (—CH$_2$—H) by —O— to form —O—H is not preferred, either.

Then, 2-fluoro-1,4-phenylene means two divalent groups described below. In a chemical formula thereof, fluorine may be leftward (L) or rightward (R). The rule is also applied to an asymmetrical divalent ring such as tetrahydropyran-2,5-diyl.

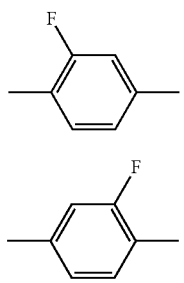

(L)

(R)

The invention includes the content described in items 1 to 15 below.

Item 1. A compound represented by formula (1):

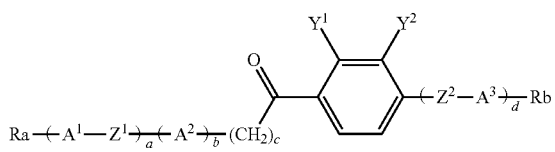

(1)

wherein, in formula (1),

Ra and Rb are independently hydrogen, halogen or alkyl having 1 to 10 carbons, and in the alkyl, at least one of —CH$_2$— may be replaced by —O—, —S—, —CO— or —SiH$_2$—, and at least one of —(CH$_2$)$_2$— may be replaced by —CH=CH— or —C≡C—, and in the groups, at least one of hydrogen may be replaced by fluorine;

A$^1$, A$^2$ and A$^3$ are independently 1,4-cyclohexylene, 1,4-phenylene, cyclohexene-1,4-diyl, 2,6,7-trioxabicyclo[2.2.2]octane-1,4-diyl, decahydronaphthalene-2,6-diyl, 1,2,3,4-tetrahydronaphthalene-2,6-diyl or naphthalene-2,6-diyl, and in the groups, one of —CH$_2$— may be replaced by —O—, —S—, —CO— or —SiH$_2$—, and at least one of —(CH$_2$)$_2$— may be replaced by —CH=CH— or —CH=N—, and in the groups, at least one of hydrogen may be replaced by halogen, —C≡N, —CF$_3$, —CHF$_2$, —CH$_2$F, —OCF$_3$, —OCHF$_2$ or —OCH$_2$F;

Z$^1$ and Z$^2$ are independently a single bond or alkylene having 1 to 4 carbons, and in the alkylene, at least one of —CH$_2$— may be replaced by —O—, —S—, —CO— or —SiH$_2$—, and at least one of —(CH$_2$)$_2$— may be replaced by —CH=CH— or —C≡C—, and in the groups, at least one of hydrogen may be replaced by halogen;

Y$^1$ is —CF$_2$H or —CF$_3$, and Y$^2$ is hydrogen, halogen, —CFH$_2$, —CF$_2$H or —CF$_3$;

a, b and d are independently 0, 1, 2 or 3, and a sum of a, b and d is 4 or less, and when a, b or d is 2 or more, two of ring A$^1$ selected from two or more of ring A$^1$, two of ring A$^2$ selected from two or more of ring A$^2$, two of ring A$^3$ selected from two or more of ring A$^3$, two of Z$^1$ selected from two or more of Z$^1$, or two of Z$^2$ selected from two or more of Z$^2$ may be identical or different; and c is 0, 1, 2, 3, 4, 5, 6, 7, 8, 9 or 10.

Item 2. The compound according to item 1, represented by formula (1-0):

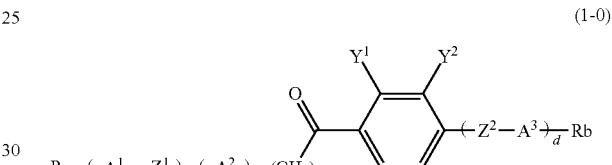

(1-0)

wherein, in formula (1-0),

Ra and Rb are independently hydrogen, halogen or alkyl having 1 to 10 carbons, and in the alkyl, at least one of —CH$_2$— may be replaced by —O—, —S—, —CO— or —SiH$_2$—, and at least one of —(CH$_2$)$_2$— may be replaced by —CH=CH— or —C≡C—, and in the groups, at least one of hydrogen may be replaced by fluorine;

A$^1$, A$^2$ and A$^3$ are independently 1,4-cyclohexylene, 1,4-phenylene, cyclohexene-1,4-diyl, 2,6,7-trioxabicyclo[2.2.2]octane-1,4-diyl, decahydronaphthalene-2,6-diyl, 1,2,3,4-tetrahydronaphthalene-2,6-diyl or naphthalene-2,6-diyl, and in the groups, one of —CH$_2$— may be replaced by —O—, —S—, —CO— or —SiH$_2$—, at least one of —(CH$_2$)$_2$— may be replaced by —CH=CH— or —CH=N—, and at least one of hydrogen may be replaced by halogen, —C≡N, —CF$_3$, —CHF$_2$, —CH$_2$F, —OCF$_3$, —OCHF$_2$ or —OCH$_2$F;

Z$^1$ and Z$^2$ are independently a single bond or alkylene having 1 to 4 carbons, and in the alkylene, at least one of —CH$_2$— may be replaced by —O—, —S—, —CO— or —SiH$_2$—, and at least one of —(CH$_2$)$_2$— may be replaced by —CH=CH— or —C≡C—, and in the groups, at least one of hydrogen may be replaced by halogen;

Y$^1$ is —CF$_2$H or —CF$_3$, and Y$^2$ is hydrogen, halogen, —CFH$_2$, —CF$_2$H or —CF$_3$;

a, b and d are independently 0, 1, 2 or 3, and a sum of a, b and d is 4 or less, and when a, b or d is 2 or more, two of ring A$^1$ selected from two or more of ring A$^1$, two of ring A$^2$ selected from two or more of ring A$^2$, two of ring A$^3$ selected from two or more of ring A$^3$, two of Z$^1$ selected from two or more of Z$^1$, or two of Z$^2$ selected from two or more of Z$^2$ may be identical or different; and c is 0, 1, 2, 3, 4, 5 or 6.

Item 3. The compound according to item 1, represented by any one of formulas (1-1) to (1-10):

(1-1) 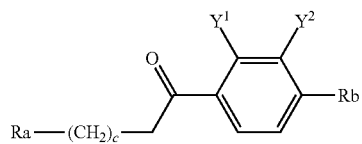

(1-2) 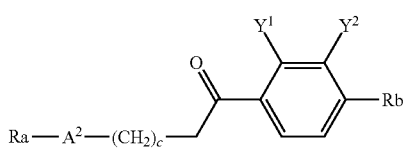

(1-3) 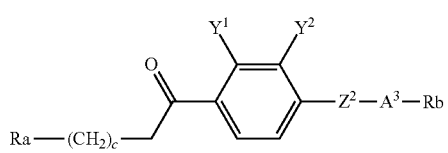

(1-4) 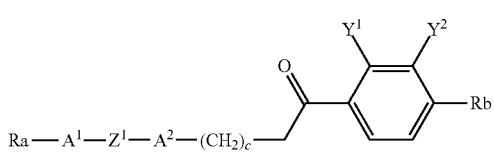

(1-5) 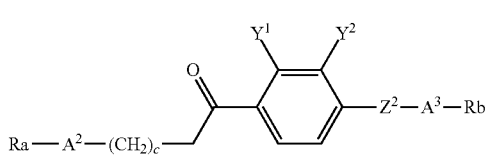

(1-6) 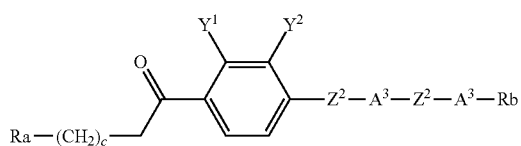

(1-7) 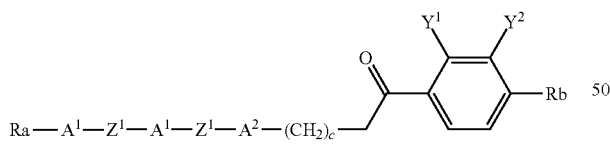

(1-8) 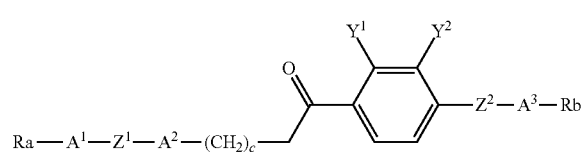

(1-9) 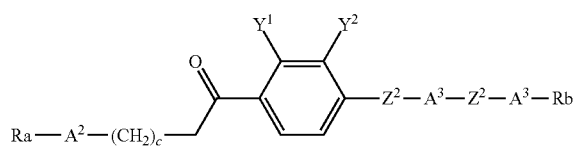

-continued (1-10) 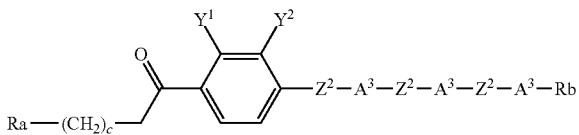

wherein, in formulas (1-1) to (1-10),

Ra and Rb are independently fluorine, chlorine or alkyl having 1 to 10 carbons, and in the alkyl, at least one of —CH$_2$— may be replaced by —O— or —CO—, and at least one of —(CH$_2$)$_2$— may be replaced by —CH=CH— or —C≡C—, and in the groups, at least one of hydrogen may be replaced by fluorine;

A$^1$, A$^2$ and A$^3$ are independently 1,4-cyclohexylene, 1,4-phenylene, 2-fluoro-1,4-phenylene, 2,3-difluoro-1,4-phenylene, 3,5-difluoro-1,4-phenylene, 2,5-difluoro-1,4-phenylene, cyclohexene-1,4-diyl, tetrahydropyran-2,5-diyl, 1,3-dioxane-2,5-diyl, tetrahydro-2H-pyran-2-one-3,6-diyl, pyridine-2,5-diyl, pyrimidine-2,5-diyl, 2,6,7-trioxabicyclo[2.2.2]octane-1,4-diyl, decahydronaphthalene-2,6-diyl, 1,2,3,4-tetrahydronaphthalene-2,6-diyl or naphthalene-2,6-diyl, and in the groups, at least one of hydrogen may be replaced by halogen, —C≡N, —CF$_3$, —CHF$_2$, —CH$_2$F, —OCF$_3$, —OCHF$_2$ or —OCH$_2$F;

Z$^1$ and Z$^2$ are independently a single bond, —(CH$_2$)$_2$—, —(CH$_2$)$_4$—, —COO—, —OCO—, —CH$_2$O—, —OCH$_2$—, —CF$_2$O—, —OCF$_2$—, —CH=CH—, —CF=CF—, —C≡C—, —CH$_2$CO—, —COCH$_2$—, —CH$_2$SiH$_2$—, —SiH$_2$CH$_2$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—;

Y$^1$ is —CF$_2$H or —CF$_3$, and Y$^2$ is hydrogen, halogen, —CFH$_2$, —CF$_2$H or —CF$_3$; and c is 0, 1, 2, 3, 4, 5 or 6.

Item 4. The compound according to item 1, represented by any one of formulas (1-11) to (1-20):

(1-11) 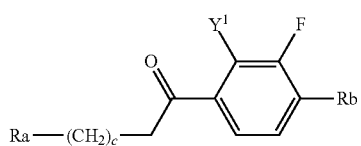

(1-12) 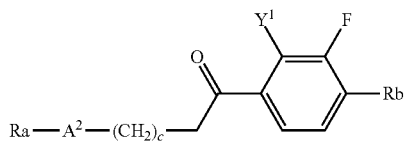

(1-13) 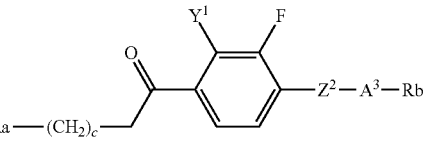

(1-14) 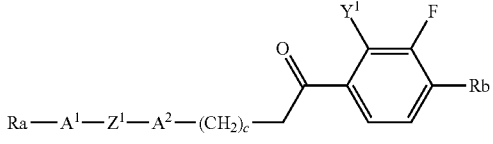

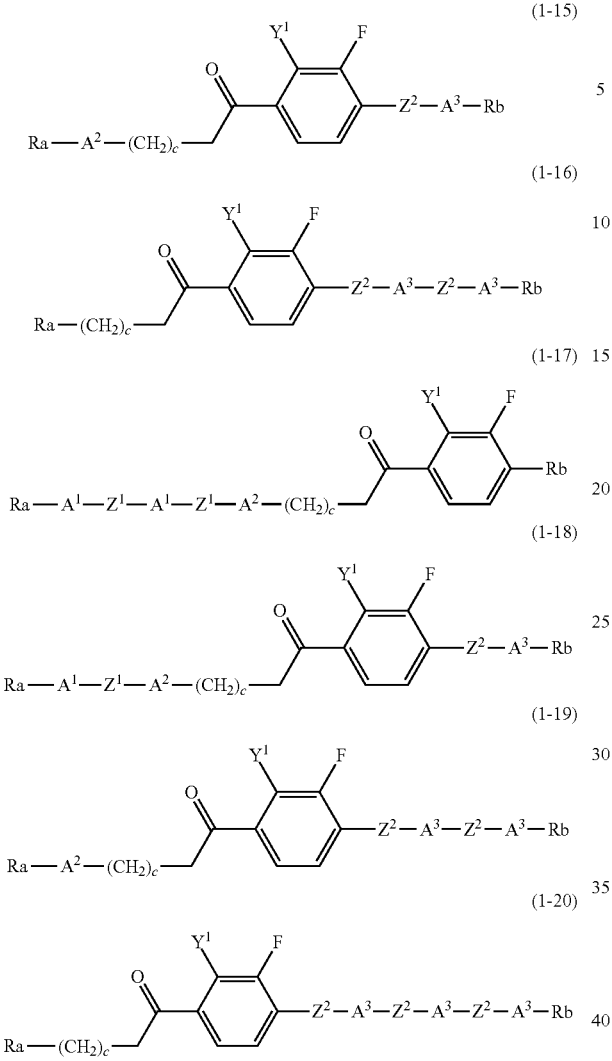
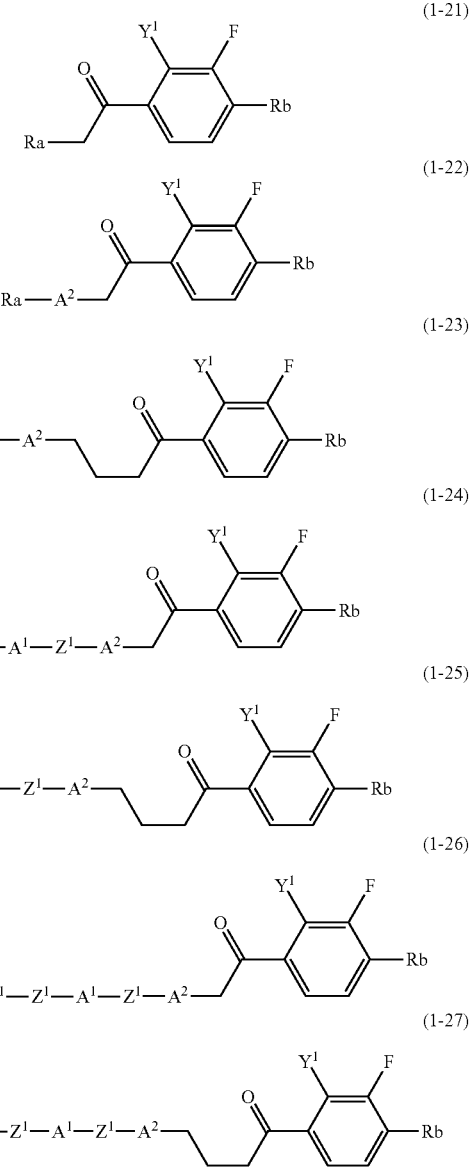

wherein, in formulas (1-11) to (1-20),

Ra and Rb are independently fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, alkyl having 1 to 10 carbons in which at least one of hydrogen is replaced by fluorine, alkoxy having 1 to 9 carbons in which at least one of hydrogen is replaced by fluorine, or alkenyl having 2 to 10 carbons in which at least one of hydrogen is replaced by fluorine;

$A^1$, $A^2$ and $A^3$ are independently 1,4-cyclohexylene, 1,4-phenylene, 2-fluoro-1,4-phenylene, 2,3-difluoro-1,4-phenylene, cyclohexene-1,4-diyl or tetrahydropyran-2,5-diyl;

$Z^1$ and $Z^2$ are independently a single bond, —(CH$_2$)$_2$—, —(CH$_2$)$_4$—, —COO—, —OCO—, —CH$_2$O—, —OCH$_2$—, —CF$_2$O—, —OCF$_2$—, —CH=CH—, —CF=CF—, —C≡C—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—;

$Y^1$ is —CF$_2$H or —CF$_3$; and c is 0, 1, 2, 3, 4, 5 or 6.

Item 5. The compound according to item 1, represented by any one of formulas (1-21) to (1-27):

wherein, in formulas (1-21) to (1-27),

Ra and Rb are independently alkyl having 1 to 10 carbons, alkenyl having 2 to 10 carbons, alkoxy having 1 to 9 carbons, fluorinated alkyl having 1 to 10 carbons or fluorinated alkoxy having 1 to 9 carbons;

$A^1$ and $A^2$ are independently 1,4-cyclohexylene, 1,4-phenylene, 2-fluoro-1,4-phenylene, 2,3-difluoro-1,4-phenylene, cyclohexene-1,4-diyl or tetrahydropyran-2,5-diyl;

$Z^1$ is independently a single bond, —(CH$_2$)$_2$—, —(CH$_2$)$_4$—, —CH$_2$O—, —OCH$_2$—, —CF$_2$O—, —OCF$_2$—, —CH=CH— or —C≡C—; and $Y^1$ is —CF$_2$H or —CF$_3$.

Item 6. The compound according to item 5, wherein, in formulas (1-21) to (1-27) according to item 5, Ra and Rb are independently alkyl having 1 to 10 carbons, alkenyl having 2 to 10 carbons or alkoxy having 1 to 9 carbons;

$A^1$ and $A^2$ are independently 1,4-cyclohexylene, 1,4-phenylene, 2-fluoro-1,4-phenylene, 2,3-difluoro-1,4-phenylene or tetrahydropyran-2,5-diyl;

$Z^1$ is a single bond; and $Y^1$ is —CF$_2$H or —CF$_3$.

Item 7. The compound according to item 5, wherein, in formulas (1-21) to (1-27) according to item 5, Ra and Rb are independently alkyl having 1 to 10 carbons or alkoxy having 1 to 9 carbons;

$A^1$ and $A^2$ are independently 1,4-cyclohexylene or 1,4-phenylene;

$Z^1$ is a single bond; and $Y^1$ is $CF_2H$.

Item 8. The compound according to item 5, wherein, in formulas (1-21) to (1-27) according to item 5, Ra and Rb are independently alkyl having 1 to 10 carbons or alkoxy having 1 to 9 carbons;

$A^1$, $A^2$ and $A^3$ are independently 1,4-cyclohexylene or 1,4-phenylene;

$Z^1$ and $Z^2$ are a single bond; and $Y^1$ is $-CF_3$.

Item 9. A liquid crystal composition, containing at least one compound according to any one of items 1 to 8.

Item 10. The liquid crystal composition according to item 9, further containing at least one compound selected from the group of compounds represented by formulas (6) to (12):

$R^{14}$ is alkyl having 1 to 10 carbons, and in the alkyl, at least one of $-CH_2-$ may be replaced by $-O-$ and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of $-CH_2-$ may be replaced by $-O-$, and at least one of hydrogen may be replaced by fluorine;

$S^{11}$ is hydrogen or methyl;

X is $-CF_2-$, $-O-$ or $-CHF-$;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, $-CH_2CH_2-$, $-COO-$, $-CH_2O-$, $-OCF_2-$ or $-OCF_2CH_2CH_2-$;

$L^{15}$ and $L^{16}$ are independently fluorine or chlorine; and

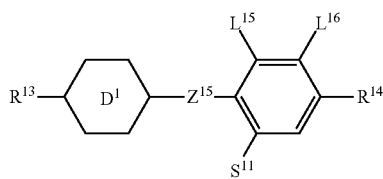
(6)

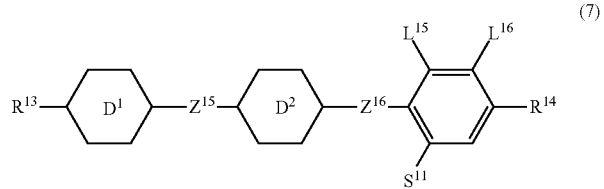
(7)

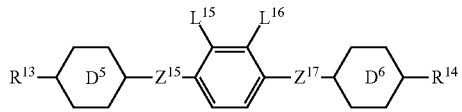
(8)

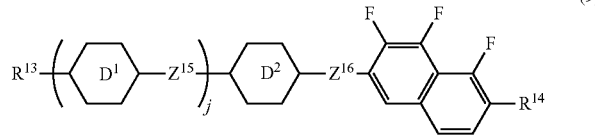
(9)

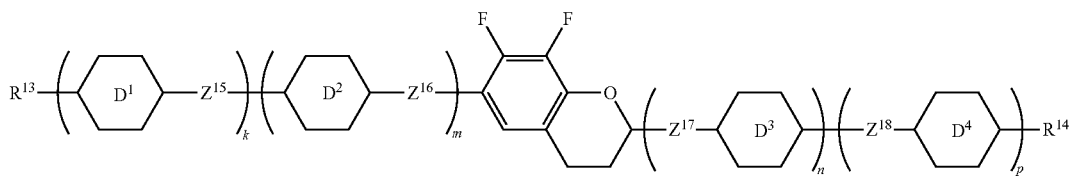
(10)

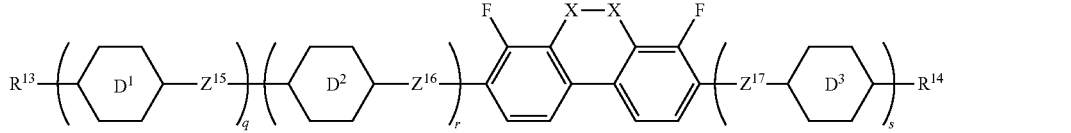
(11)

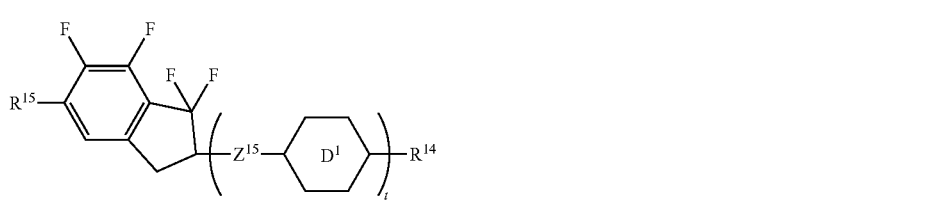
(12)

wherein, in formulas (6) to (12), $R^{13}$ is alkyl having 1 to 10 carbons or alkenyl having 2 to 10 carbons, and in the alkyl and the alkenyl, at least one of $-CH_2-$ may be replaced by $-O-$ and at least one of hydrogen may be replaced by fluorine;

j, k, m, n, p, q, r and s are independently 0 or 1, a sum of k, m, n and p is 1 or 2, a sum of q, r and s is 0, 1, 2 or 3, and t is 1, 2 or 3.

Item 11. The liquid crystal composition according to item 9 or 10, further containing at least one compound selected from the group of compounds represented by formulas (13) to (15):

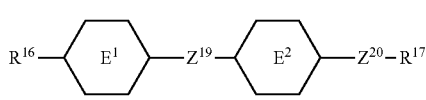
(13)

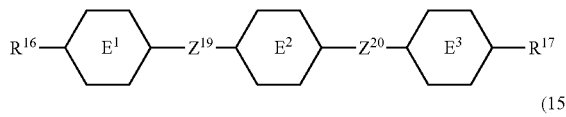
(14)

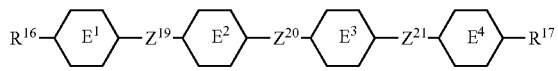
(15)

wherein, in formulas (13) to (15), $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH═CH—, —C≡C— or —COO—.

Item 12. The liquid crystal composition according to any one of items 9 to 11, further containing at least one compound selected from the group of compounds represented by formulas (2) to (4):

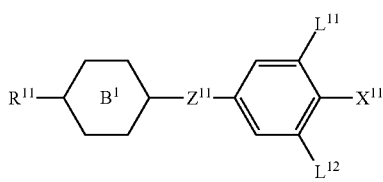
(2)

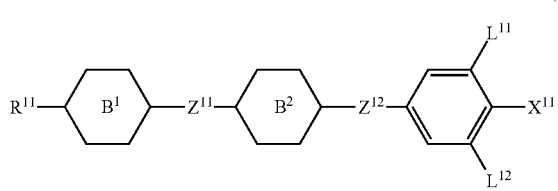
(3)

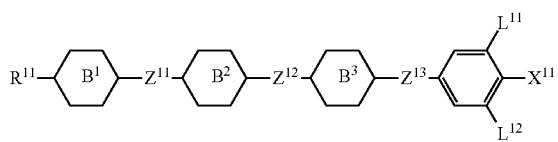
(4)

wherein, in formulas (2), (3), (4)

$R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH═CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 13. The liquid crystal composition according to any one of items 9 to 12, further containing at least one compound selected from the group of compounds represented by formula (5):

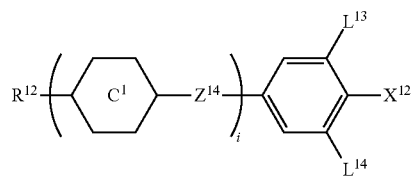
(5)

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{12}$ is —C≡N or —C≡C—C≡N;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 14. The liquid crystal composition according to any one of items 9 to 13, further containing at least one optically active compound and/or at least one polymerizable compound.

Item 15. The liquid crystal composition according to any one of items 9 to 14, further containing at least one antioxidant and/or at least one ultraviolet light absorbent.

Item 16. A liquid crystal display device, including the liquid crystal composition according to any one of items 9 to 15.

The compound, the liquid crystal composition and the liquid crystal display device according to the invention will be described in the order.

1-1. Compound (1)

Compound (1) of the invention will be described. Preferred examples of a terminal group, a ring structure, a bonding group or the like in compound (1), and an effect of the groups on physical properties are also applied to a subordinate formula of formula (1) for compound (1).

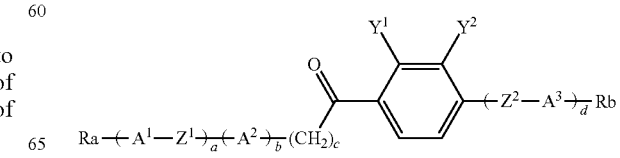
(1)

In formula (1), Ra and Rb are independently hydrogen, halogen or alkyl having 1 to 10 carbons, and in the alkyl, at least one of —$CH_2$— may be replaced by —O—, —S—, —CO— or —$SiH_2$—, and at least one of —$(CH_2)_2$— may be replaced by —CH=CH— or —C≡C—, and in the groups, at least one of hydrogen may be replaced by fluorine. The groups have a straight chain or a branched chain, and do not include a cyclic group such as cyclohexyl. In the groups, the straight chain is preferred to the branched chain.

A preferred configuration of —CH=CH— in alkenyl depends on a position of a double bond. A trans configuration is preferred in alkenyl having the double bond in an odd-numbered position, such as —CH=$CHCH_3$, —CH=$CHC_2H_5$, —CH=$CHC_3H_7$, —CH=$CHC_4H_9$, —$C_2H_4$CH=$CHCH_3$ or —$C_2H_4$CH=$CHC_2H_5$. A cis configuration is preferred in alkenyl having the double bond in an even-numbered position, such as —$CH_2$CH=$CHCH_3$, —$CH_2$CH=$CHC_2H_5$ or —$CH_2$CH=$CHC_3H_7$. The alkenyl compound having the preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

Preferred examples of Ra or Rb include alkyl, alkoxy, alkenyl and alkenyloxy. Further preferred examples of Ra or Rb include alkyl, alkoxy and alkenyl.

Examples of alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$ and —$C_{15}H_{31}$.

Examples of alkoxy include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$, —$OC_{11}H_{23}$, —$OC_{12}H_{25}$, —$OC_{13}H_{27}$ and —$OC_{14}H_{29}$.

Examples of alkoxyalkyl include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ and —$(CH_2)_5$—$OCH_3$.

Examples of alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ and —$(CH_2)_3$—CH=$CH_2$.

Examples of alkenyloxy include —$OCH_2$CH=$CH_2$, —$OCH_2$CH=$CHCH_3$ and —$OCH_2$CH=$CHC_2H_5$.

Examples of alkyl in which at least one of hydrogen is replaced by halogen include —$CH_2F$, —$CHF_2$, —$CF_3$, —$(CH_2)_2$—F, —$CF_2CH_3$, —$CF_2CH_2F$, —$CF_2CHF_2$, —$CH_2CF_3$, —$CF_2CF_3$, —$(CH_2)_3$—F, —$CF_2CH_2CH_3$, —$CH_2$CHF$CH_3$, —$CH_2CF_2CH_3$, —$(CF_2)_3$—F, —$CF_2$CHF$CF_3$, —CHF$CF_2CF_3$, —$(CH_2)_4$—F, —$CF_2(CH_2)_2CH_3$, —$(CF_2)_4$—F, —$(CH_2)_5$—F, —$(CF_2)_5$—F, —$CH_2Cl$, —$CHCl_2$, —$CCl_3$, —$(CH_2)_2$—Cl, —$CCl_2CH_3$, —$CCl_2CH_2Cl$, —$CCl_2CHCl_2$, —CH2$CCl_3$, —$CCl_2CCl_3$, —$(CH_2)_3$—Cl, —$CCl_2CH_2CH_3$, —$(CCl_2)_3$—Cl, —$CCl_2$CHCl$CCl_3$, —CHCl$CCl_2CCl_3$, —$(CH_2)_4$—Cl, —$(CCl_2)_4$—Cl, —$CCl_2(CH_2)_2CH_3$, —$(CH_2)_5$—Cl and —$(CCl_2)_5$—Cl.

Examples of alkoxy in which at least one of hydrogen is replaced by halogen include —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2$CHF$CF_3$, —OCHF$CF_2CF_3$, —O$(CH_2)_4$—F, —O—$(CF_2)_4$—F, —O—$(CH_2)_5$—F, —O—$(CF_2)_5$—F, —$OCH_2$CHF$CH_3$, —$OCH_2Cl$, —$OCHCl_2$, —$OCCl_3$, —O—$(CH_2)_2$—Cl, —$OCCl_2CH_2Cl$, —$OCCl_2CHCl_2$, —$OCH_2CCl_3$, —O—$(CH_2)_3$—Cl, —O—$(CCl_2)_3$—Cl, —$OCCl_2$CHCl$CCl_3$, —OCHCl$CCl_2CCl_3$, —O$(CH_2)_4$—Cl, —O—$(CCl_2)_4$—Cl, —O—$(CH_2)_5$—Cl and —O—$(CCl_2)_5$—Cl.

Examples of alkenyl in which at least one of hydrogen is replaced by halogen include —CH=CHF, —CH=$CF_2$, —CF=CHF, —CH=$CHCH_2F$, —CH=$CHCF_3$, —$(CH_2)_2$—CH=$CF_2$, —$CH_2$CH=$CHCF_3$, —CH=$CHCF_2CF_3$, —CH=CHCl, —CH=$CCl_2$, —CCl=CHCl, —CH=$CHCH_2Cl$, —CH=$CHCCl_3$, —$(CH_2)_2$—CH=$CCl_2$, —$CH_2$CH=$CHCCl_3$ and —CH=$CHCCl_2CCl_3$.

In formula (1), $A^1$, $A^2$ and $A^3$ are independently 1,4-cyclohexylene, 1,4-phenylene, cyclohexene-1,4-diyl, 2,6,7-trioxabicyclo[2.2.2]octane-1,4-diyl, decahydronaphthalene-2,6-diyl, 1,2,3,4-tetrahydronaphthalene-2,6-diyl or naphthalene-2,6-diyl, and in the groups, one of —$CH_2$— may be replaced by —O—, —S—, —CO— or —$SiH_2$—, at least one of —$(CH_2)_2$— may be replaced by —CH=CH— or —CH=N—, and at least one of hydrogen may be replaced by halogen, —C≡N, —$CF_3$, —$CHF_2$, —$CH_2F$, —$OCF_3$, —$OCHF_2$ or —$OCH_2F$.

Preferred examples of 1,4-phenylene in which at least one of hydrogen is replaced by halogen include groups represented by formulas (A-1) to (A-17). In order to have a large negative dielectric anisotropy, a group represented by formulas (A-1), (A-5), (A-6), (A-7), (A-8), (A-9), (A-10) or (A-11) is further preferred.

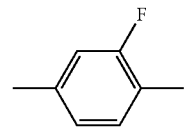

(A-1)

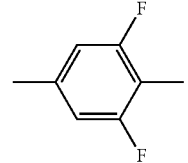

(A-2)

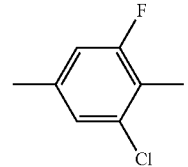

(A-3)

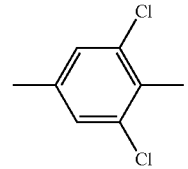

(A-4)

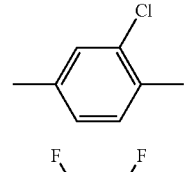

(A-5)

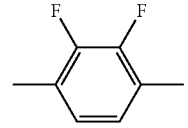

(A-6)

Preferred examples of $A^1$, $A^2$ or $A^3$ include 1,4-cyclohexylene, 1,4-phenylene, 2-fluoro-1,4-phenylene, 2,3-difluoro-1,4-phenylene, cyclohexene-1,4-diyl or tetrahydropyran-2,5-diyl. Further preferred examples thereof include 1,4-cyclohexylene, 1,4-phenylene, 2-fluoro-1,4-phenylene, 2,3-difluoro-1,4-phenylene and tetrahydropyran-2,5-diyl. Still further preferred examples thereof include 1,4-cyclohexylene and 1,4-phenylene. Cis and trans configurations exist in 1,4-cyclohexylene. From a viewpoint of a high maximum temperature, the trans configuration is preferred.

$Z^1$ and $Z^2$ are independently a single bond or alkylene having 1 to 4 carbons, and in the alkylene, at least one of —$CH_2$— may be replaced by —O—, —S—, —CO— or —$SiH_2$—, and at least one of —$(CH_2)_2$— may be replaced by —CH=CH— or —C≡C—, and in the groups, at least one of hydrogen may be replaced by halogen.

Preferred examples of $Z^1$ or $Z^2$ include a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— and —$(CH_2)_2$—CH=CH—. Further preferred examples thereof include a single bond, —$(CH_2)_2$—, —CH=CH—, —COO—, —OCO—, —$CF_2O$—, —$OCF_2$—, —$CH_2O$— and —$OCH_2$—. Still further preferred examples thereof include a single bond, —$(CH_2)_2$—, —$CH_2O$— and —$OCH_2$—.

$Y^1$ is —$CF_2H$ or —$CF_3$, and $Y^2$ is hydrogen, halogen, —$CFH_2$, —$CF_2H$ or —$CF_3$. Preferred examples of $Y^2$ include hydrogen or halogen. Further preferred examples of $Y^2$ include fluorine.

Then, a, b and d are independently 0, 1, 2 or 3, and a sum of a, b and d is 4 or less, and when a, b or d is 2 or more, two of ring $A^1$ selected from two or more of ring $A^1$, two of ring $A^2$ selected from two or more of ring $A^2$, two of ring $A^3$ selected from two or more of ring $A^3$, two of $Z^1$ selected from two or more of $Z^1$, or two of $Z^2$ selected from two or more of $Z^2$ may be identical or different. Examples of preferred combinations of a, b and d include (a=0, b=0, d=0), (a=0, b=1, d=0), (a=1, b=0, d=0), (a=1, b=1, d=0), (a=2, b=0, d=0), (a=0, b=0, d=1) or (a=0, b=0, d=2).

Then, c is 0, 1, 2, 3, 4, 5, 6, 7, 8, 9 or 10. Examples of preferred c include 1, 3 or 5, and examples of further preferred c include 1 or 3.

1-2. Physical Properties of Compound (1)

In compound (1), physical properties such as a clearing point, optical anisotropy and dielectric anisotropy can be arbitrarily adjusted by suitably selecting Ra, Rb, ring $A^1$, ring $A^2$, ring $A^3$, $Z^1$, $Z^2$, and a combination of a, b, c and d. Compound (1) may contain an isotope such as $^2H$ (deuterium) and $^{13}C$ in an amount larger than an amount of natural abundance because no significant difference is in the physical properties of the compound. A main effect of kinds of Ra or the like on the physical properties of compound (1) will be described below.

When Ra or Rb has a straight chain, a temperature range of the liquid crystal phase is wide and viscosity is small.

When Ra or Rb has a branched chain, compatibility with other liquid crystal compounds is good. A compound in which Ra or Rb is optically active is useful as a chiral dopant. A reverse twisted domain to be generated in the liquid crystal display device can be prevented by adding the compound to the composition. A compound in which both of Ra and Rb are not optically active is useful as a component of the composition. When Ra or Rb is alkenyl, a preferred configuration depends on a position of the double bond. An alkenyl compound having the preferred configuration has a small viscosity, the high maximum temperature or the wide temperature range of the liquid crystal phase. When Ra or Rb is alkoxy, the alkenyl compound has the high maximum temperature.

When all of ring $A^1$, ring $A^2$ and ring $A^3$ are 1,4-cyclohexylene, the clearing point is high and the viscosity is small. When at least one of ring $A^1$, ring $A^2$ and ring $A^3$ is 1,4-phenylene, or 1,4-phenylene in which at least one of hydrogen is replaced by halogen, the optical anisotropy is comparatively large and an orientational order parameter is comparatively large. When all of ring $A^1$, ring $A^2$ and ring $A^3$ are 1,4-phenylene, 1,4-phenylene in which at least one of hydrogen is replaced by halogen, or a combination thereof, the optical anisotropy is particularly large. When at least one of ring $A^1$, ring $A^2$ and ring $A^3$ is 2-fluoro-1,4-phenylene, 2-chloro-1,4-phenylene, 2,3-difluoro-1,4-phenylene, 2,3-dichloro-1,4-phenylene, 2-chloro-3-fluoro-1,4-phenylene or tetrahydropyran-2,5-diyl, the negative dielectric anisotropy is particularly large.

When at least one of $Z^1$ and $Z^2$ is a single bond, —$CH_2CH_2$—, —CH=CH—, —$CF_2O$— or —$OCF_2$—, the viscosity is small. When at least one of $Z^1$ and $Z^2$ is —CH=CH—, —$CH_2O$— or —$OCH_2$—, the temperature range of the liquid crystal phase is wide, and an elastic constant (K) is large. When at least one of $Z^1$ and $Z^2$ is a single bond, —CH=CH—, —C≡C—, —COO—, —OCO— or —CF=CF—, the clearing point is high. When at least one of $Z^1$ and $Z^2$ is —CH=CH—, —C≡C— or —CF=CF—, the optical anisotropy is large. When at least one of $Z^1$ and $Z^2$ is —$CH_2O$— or —$OCH_2$—, the negative dielectric anisotropy is large. When all of $Z^1$ and $Z^2$ are a single bond, —$CH_2CH_2$—, —$CH_2O$— or —$OCH_2$—, chemical stability is high. When at least one of $Z^1$ and $Z^2$ is —$(CH_2)_2$—, —CH=CH—, —COO—, —OCO—, —$CF_2O$—, —$OCF_2$—, —$CH_2O$— or —$OCH_2$—, the compatibility with other liquid crystal compounds is good.

Compound (1) has a carbonyl group in structure thereof, and a —$CF_2H$ group or a —$CF_3$ group bonded with a phenylene ring in an adjacent position thereof. Compound (1) has the large negative dielectric anisotropy due to an effect of such structure.

1-3. Preferred Compound

Preferred examples of compound (1) include compounds (1-1) to (1-10) according to item 2.

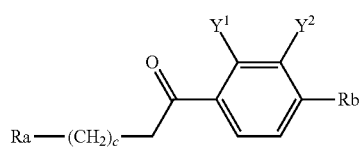
(1-1)

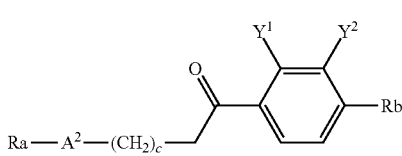
(1-2)

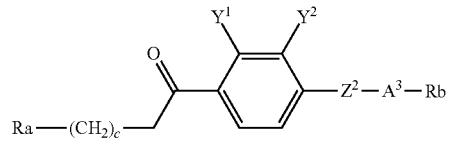
(1-3)

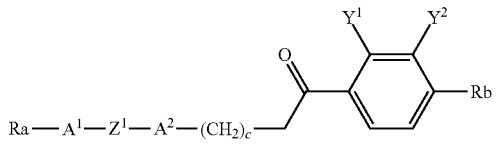
(1-4)

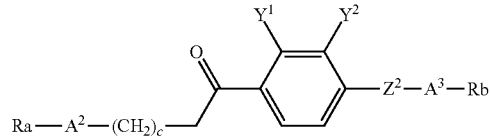
(1-5)

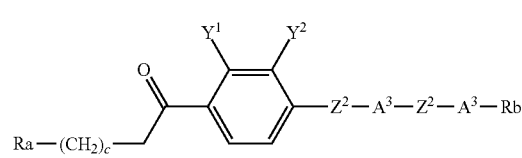
(1-6)

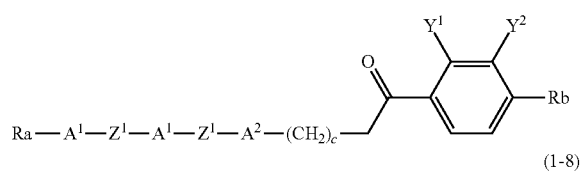
(1-7)

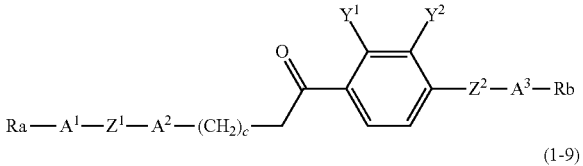
(1-8)

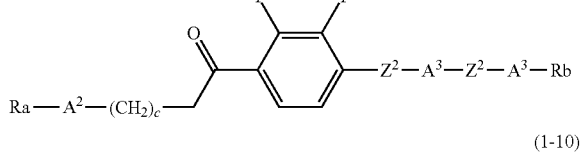
(1-9)

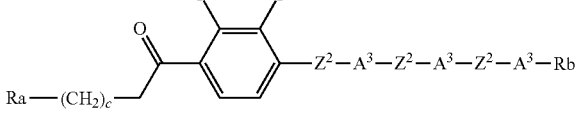
(1-10)

wherein, in formulas (1-1) to (1-10),

Ra and Rb are independently fluorine, chlorine or alkyl having 1 to 10 carbons, and in the alkyl, at least one of —$CH_2$— may be replaced by —O— or —CO—, and at least one of —$(CH_2)_2$— may be replaced by —CH=CH— or —C≡C—, and in the groups, at least one of hydrogen may be replaced by fluorine;

$A^1$, $A^2$ and $A^3$ are independently 1,4-cyclohexylene, 1,4-phenylene, 2-fluoro-1,4-phenylene, 2,3-difluoro-1,4-phenylene, 3,5-difluoro-1,4-phenylene, 2,5-difluoro-1,4-phenylene, cyclohexene-1,4-diyl, tetrahydropyran-2,5-diyl, 1,3-dioxane-2,5-diyl, tetrahydro-2H-pyran-2-one-3,6-diyl, pyridine-2,5-diyl, pyrimidine-2,5-diyl, 2,6,7-trioxabicyclo[2.2.2]octane-1,4-diyl, decahydronaphthalene-2,6-diyl, 1,2,3,4-tetrahydronaphthalene-2,6-diyl or naphthalene-2,6-diyl, and in the groups, at least one of hydrogen may be replaced by halogen, —C≡N, —CF$_3$, —CHF$_2$, —CH$_2$F, —OCF$_3$, —OCHF$_2$ or —OCH$_2$F;

$Z^1$ and $Z^2$ are independently a single bond, —(CH$_2$)$_2$—, —(CH$_2$)$_4$—, —COO—, —OCO—, —CH$_2$O—, —OCH$_2$—, —CF$_2$O—, —OCF$_2$—, —CH=CH—, —CF=CF—, —C≡C—, —CH$_2$CO—, —COCH$_2$—, —CH$_2$SiH$_2$—, —SiH$_2$CH$_2$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—;

$Y^1$ is —CF$_2$H or —CF$_3$, and $Y^2$ is hydrogen, halogen, —CFH$_2$, —CF$_2$H or CF$_3$; and c is 0, 1, 2, 3, 4, 5 or 6.

Further preferred examples of compound (1) include compounds (1-11) to (1-20) according to item 3.

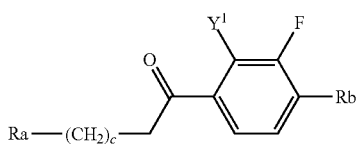
(1-11)

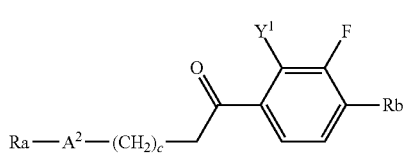
(1-12)

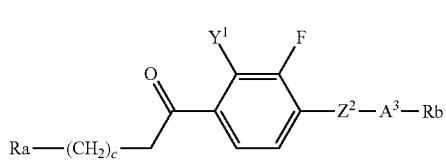
(1-13)

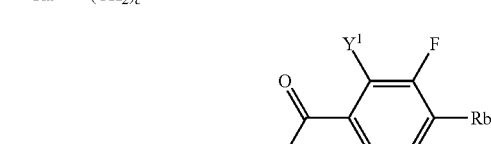
(1-14)

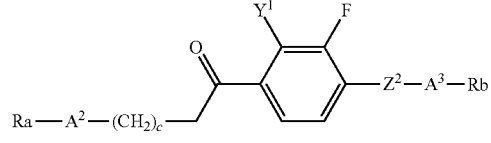
(1-15)

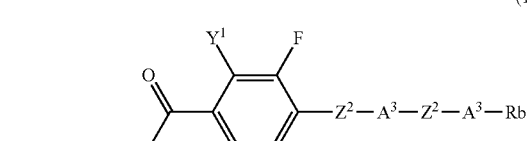
(1-16)

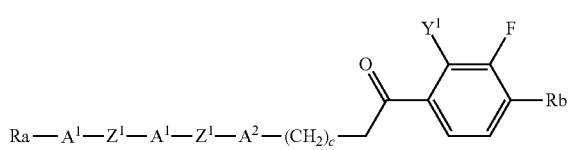
(1-17)

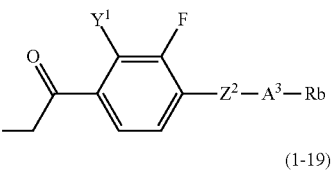
(1-18)

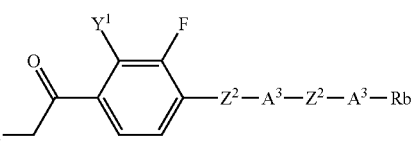
(1-19)

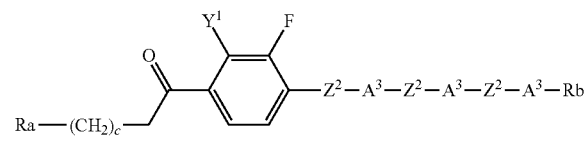
(1-20)

wherein, in formulas (1-11) to (1-20),

Ra and Rb are independently fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, alkyl having 1 to 10 carbons in which at least one of hydrogen is replaced by fluorine, alkoxy having 1 to 9 carbons in which at least one of hydrogen is replaced by fluorine, or alkenyl having 2 to 10 carbons in which at least one of hydrogen is replaced by fluorine;

$A^1$, $A^2$ and $A^3$ are independently 1,4-cyclohexylene, 1,4-phenylene, 2-fluoro-1,4-phenylene, 2,3-difluoro-1,4-phenylene or cyclohexene-1,4-diyll;

$Z^1$ and $Z^2$ are independently a single bond, —(CH$_2$)$_2$—, —(CH$_2$)$_4$—, —COO—, —OCO—, —CH$_2$O—, —OCH$_2$—, —CF$_2$O—, —OCF$_2$—, —CH=CH—, —CF=CF—, —C≡C—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—;

$Y^1$ is —CF$_2$H or —CF$_3$; and c is 0, 1, 2, 3, 4, 5 or 6.

Still further preferred examples of compound (1) include compounds (1-21) to (1-27) according to item 4.

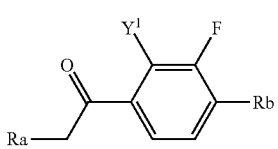
(1-21)

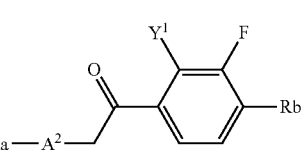
(1-22)

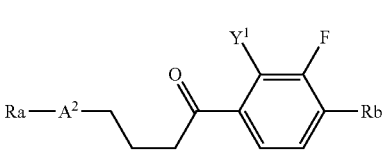
(1-23)

(1-24)
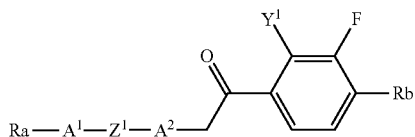

(1-25)
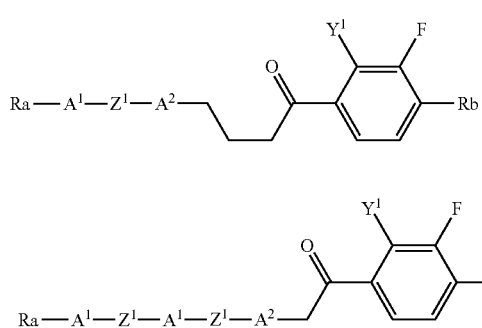

(1-26)
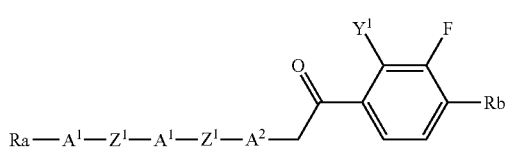

(1-27)
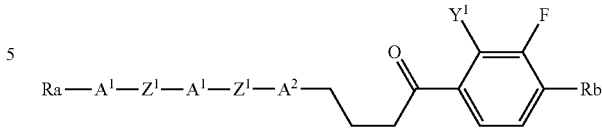

wherein, in formulas (1-21) to (1-27), Ra and Rb are independently alkyl having 1 to 10 carbons, alkenyl having 2 to 10 carbons, alkoxy having 1 to 9 carbons, alkyl having 1 to 10 carbons in which at least one of hydrogen is replaced by fluorine, or alkoxy having 1 to 9 carbons in which at least one of hydrogen is replaced by fluorine;

$A^1$ and $A^2$ are independently 1,4-cyclohexylene, 1,4-phenylene, 2-fluoro-1,4-phenylene, 2,3-difluoro-1,4-phenylene or cyclohexene-1,4-diyl;

$Z^1$ is independently a single bond, —$(CH_2)_2$—, —$(CH_2)_4$—, —$CH_2O$—, —$OCH_2$—, —$CF_2O$—, —$OCF_2$—, —CH=CH— or —C≡C—; and $Y^1$ is —$CF_2H$ or —$CF_3$.

Specific examples of preferred examples of compound (1) include compounds represented by formulas (1-28) to (1-83).

(1-28)
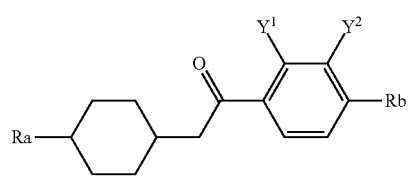

(1-29)
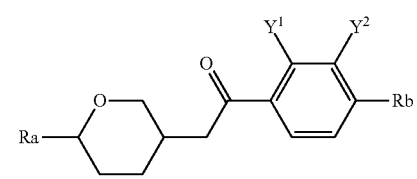

(1-30)
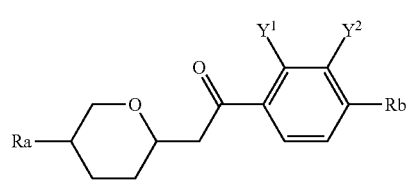

(1-31)
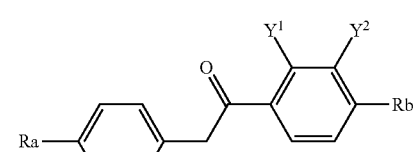

(1-32)
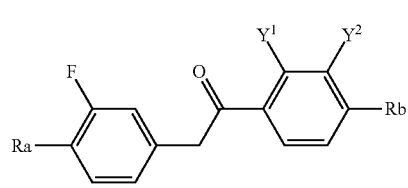

(1-33)
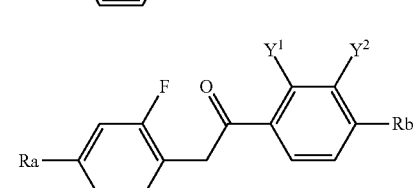

(1-34)
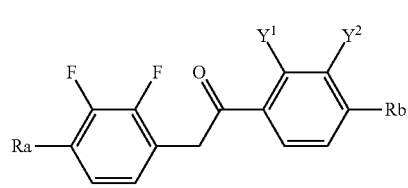

(1-35)
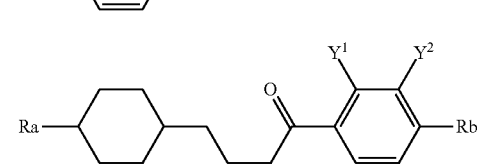

(1-36)
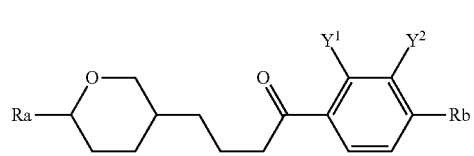

(1-37)
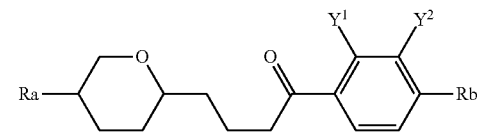

(1-38)
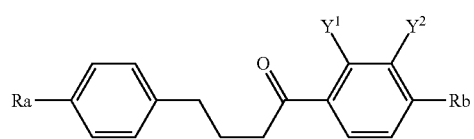

(1-39)
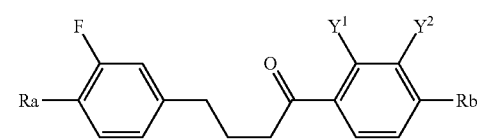

-continued
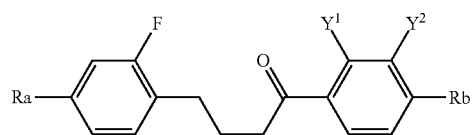
(1-40)
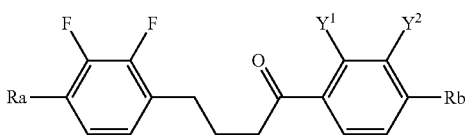
(1-41)
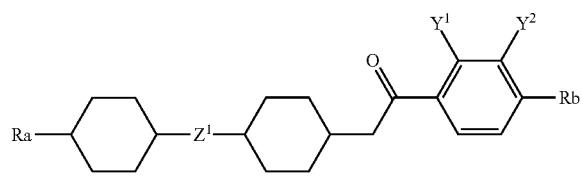
(1-42)
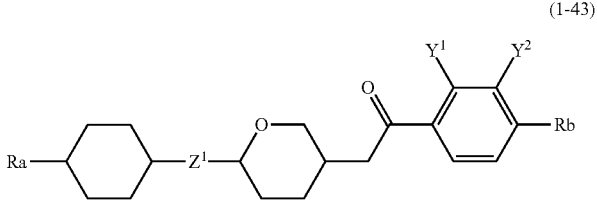
(1-43)
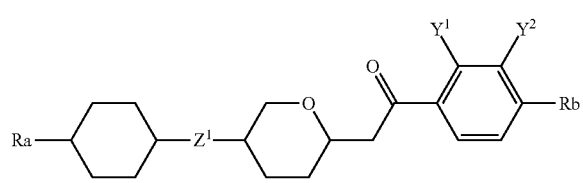
(1-44)
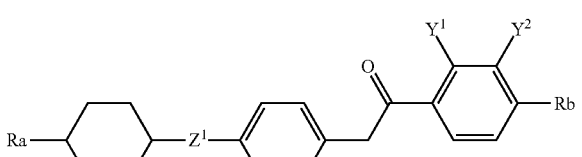
(1-45)
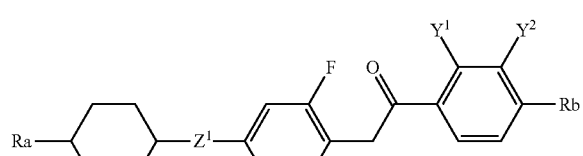
(1-46)
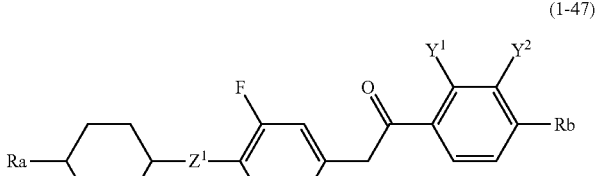
(1-47)
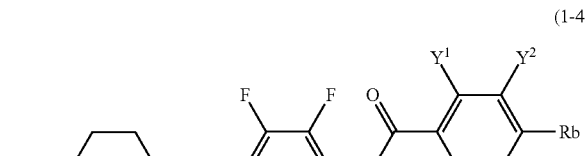
(1-48)
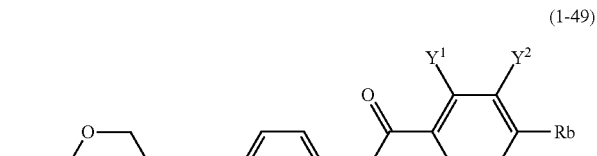
(1-49)
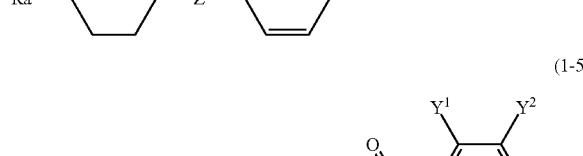
(1-50)
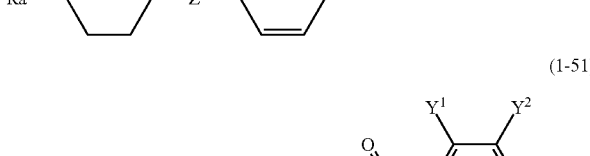
(1-51)
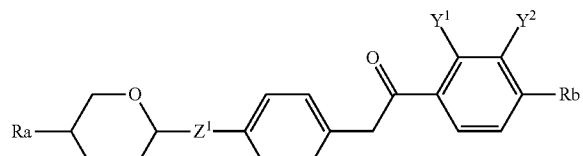
(1-52)
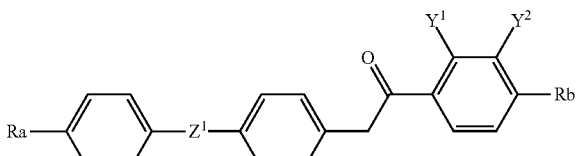
(1-53)
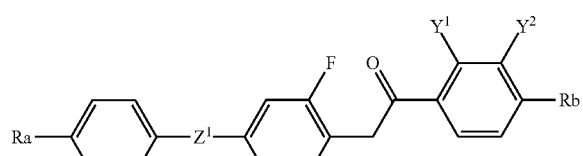
(1-54)
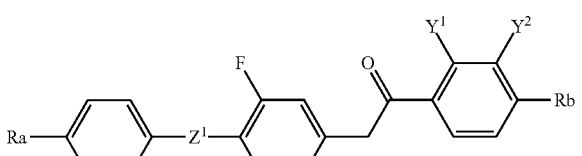
(1-55)
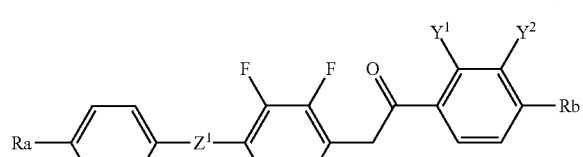
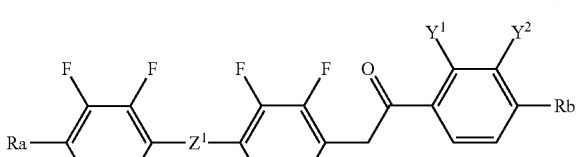

-continued
(1-56)
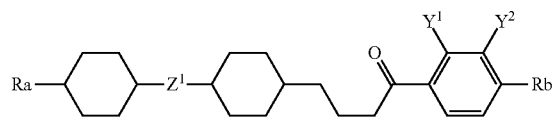
(1-57)
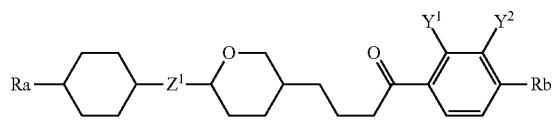
(1-58)
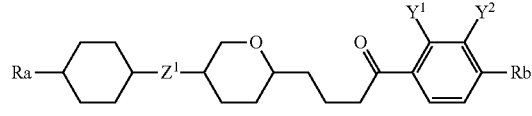
(1-59)
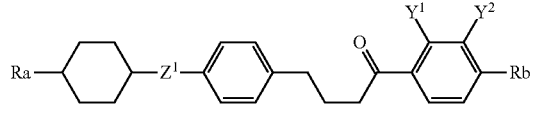
(1-60)
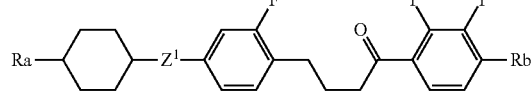
(1-61)
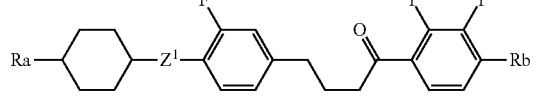
(1-62)
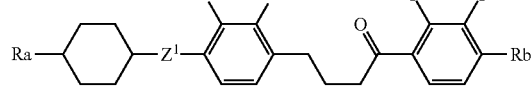
(1-63)
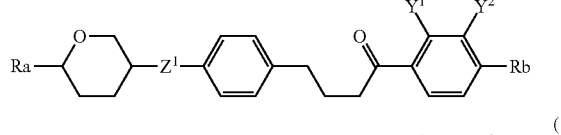
(1-64)
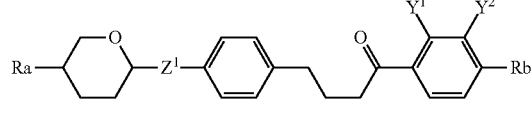
(1-65)
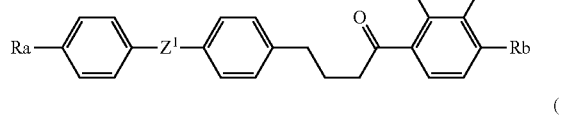
(1-66)
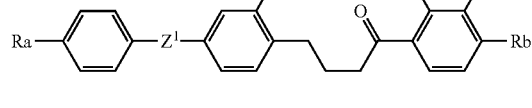
(1-67)
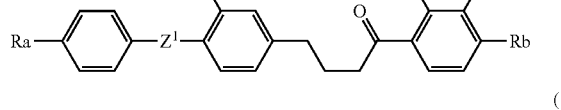
(1-68)
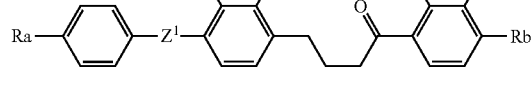
(1-69)
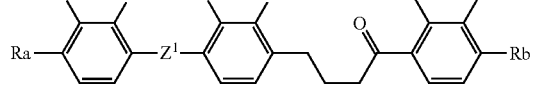
(1-70)
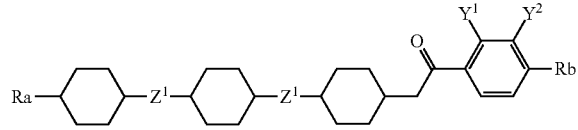
(1-71)
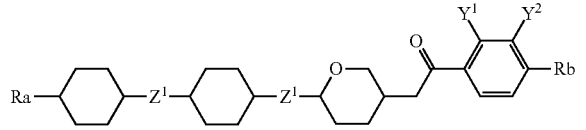
(1-72)
(1-73)
(1-74)
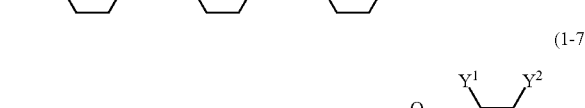
(1-75)
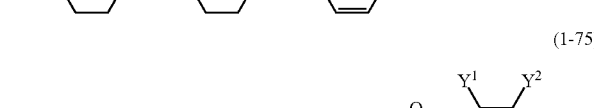
(1-76)
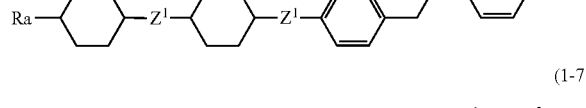
(1-77)
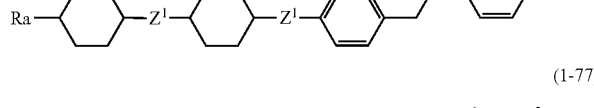

-continued

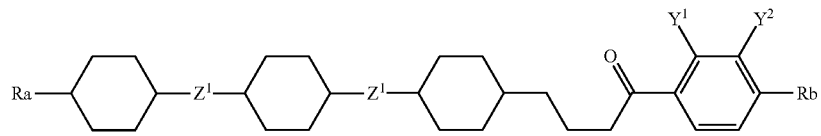

(1-78)

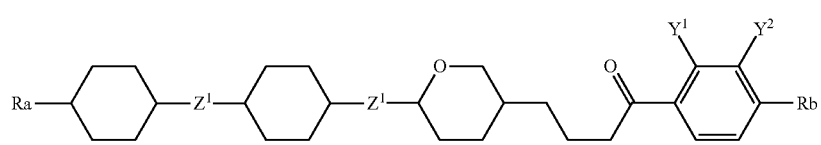

(1-79)

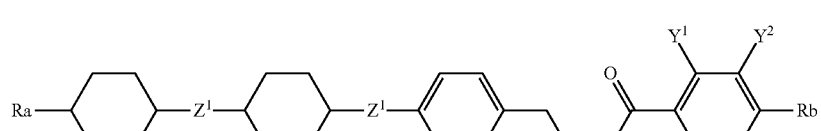

(1-80)

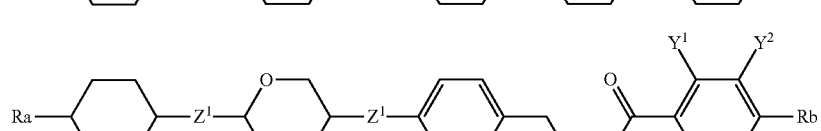

(1-81)

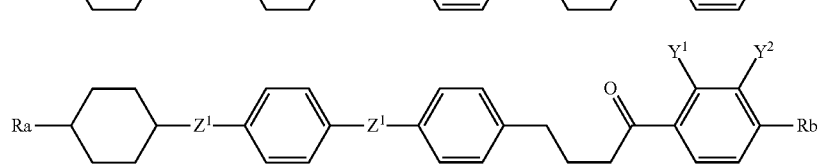

(1-82)

(1-83)

wherein, in formulas (1-28) to (1-83), Ra and Rb are independently fluorine, alkyl having 1 to 10 carbons, alkenyl having 2 to 10 carbons, alkoxy having 1 to 9 carbons, alkoxyalkyl having 2 to 9 carbons, alkenyloxy having 3 to 9 carbons, alkyl having 1 to 10 carbons in which at least one of hydrogen is replaced by fluorine, alkoxy having 1 to 9 carbons in which at least one of hydrogen is replaced by fluorine, or alkenyl having 2 to 10 carbons in which at least one of hydrogen is replaced by fluorine;

$Z^1$ is independently a single bond, $-(CH_2)_2-$, $-(CH_2)_4-$, $-COO-$, $-OCO-$, $-CH_2O-$, $-OCH_2-$, $-CF_2O-$, $-OCF_2-$, $-CH=CH-$ or $H-C\equiv C-$; and $Y^1$ is $-CF_2H$ or $-CF_3$, and $Y^2$ is hydrogen, halogen, $CFH_2$, $CF_2H$ or $CF_3$.

1-4. Synthesis of Compound (1)

A method for preparing compound (1) will be described. Compound (1) can be prepared by suitably combining methods in synthetic organic chemistry. Methods for introducing an objective terminal group, ring or bonding group into a starting material are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.).

1-4-1. Formation of a Bonding Group

An example of a method for forming a bonding group in compound (1) is as described in the scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1G) correspond to compound (1) or an intermediate of compound (1).

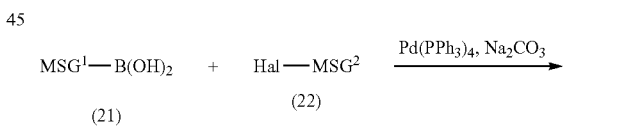

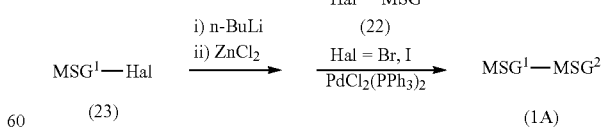

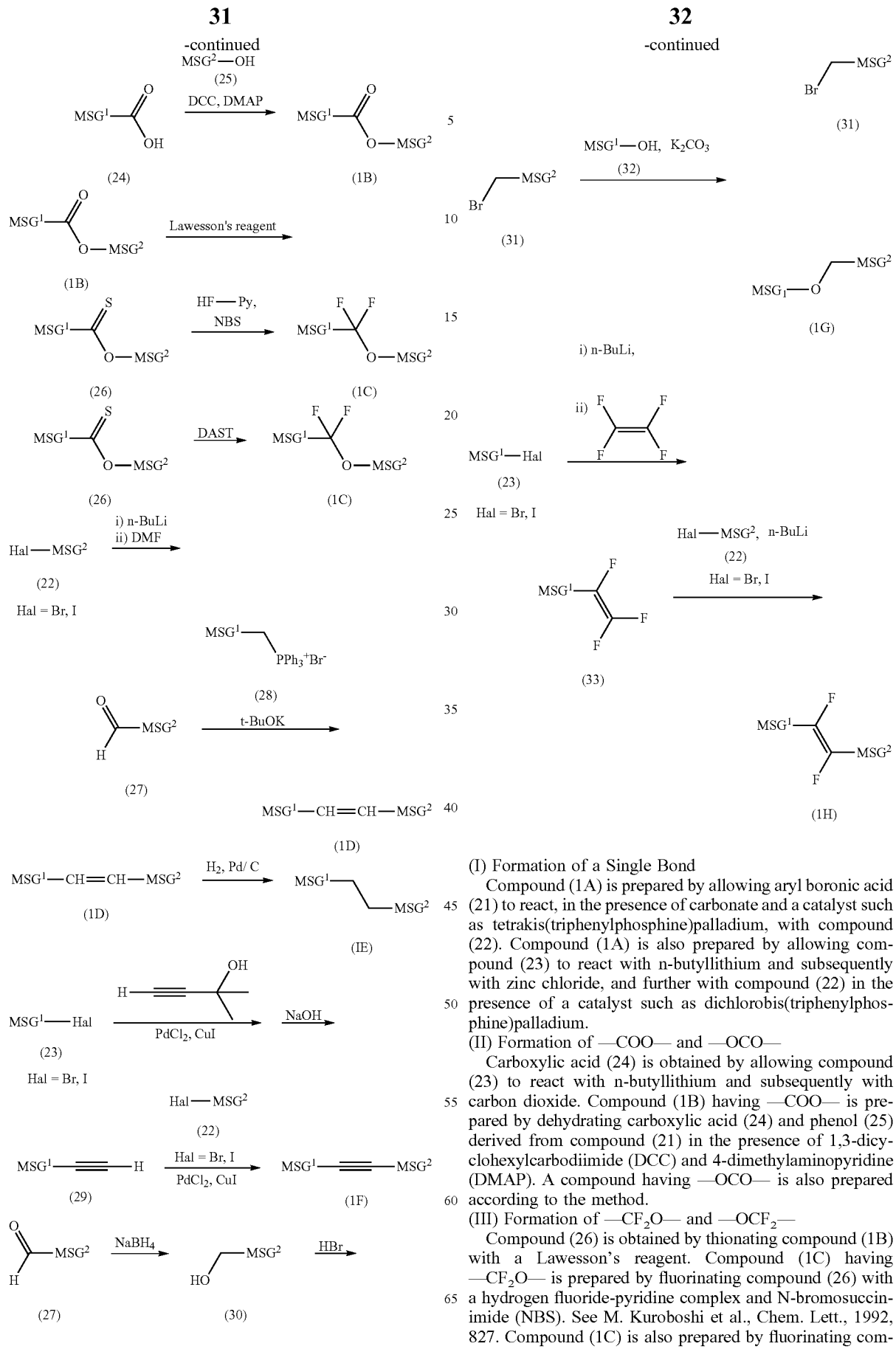

(I) Formation of a Single Bond

Compound (1A) is prepared by allowing aryl boronic acid (21) to react, in the presence of carbonate and a catalyst such as tetrakis(triphenylphosphine)palladium, with compound (22). Compound (1A) is also prepared by allowing compound (23) to react with n-butyllithium and subsequently with zinc chloride, and further with compound (22) in the presence of a catalyst such as dichlorobis(triphenylphosphine)palladium.

(II) Formation of —COO— and —OCO—

Carboxylic acid (24) is obtained by allowing compound (23) to react with n-butyllithium and subsequently with carbon dioxide. Compound (1B) having —COO— is prepared by dehydrating carboxylic acid (24) and phenol (25) derived from compound (21) in the presence of 1,3-dicyclohexylcarbodiimide (DCC) and 4-dimethylaminopyridine (DMAP). A compound having —OCO— is also prepared according to the method.

(III) Formation of —CF$_2$O— and —OCF$_2$—

Compound (26) is obtained by thionating compound (1B) with a Lawesson's reagent. Compound (1C) having —CF$_2$O— is prepared by fluorinating compound (26) with a hydrogen fluoride-pyridine complex and N-bromosuccinimide (NBS). See M. Kuroboshi et al., Chem. Lett., 1992, 827. Compound (1C) is also prepared by fluorinating compound (26) with (diethylamino)sulfur trifluoride (DAST). See W. H. Bunnelle et al., J. Org. Chem. 1990, 55, 768. A compound having —OCF$_2$— is also prepared according to the method.

(IV) Formation of —CH═CH—

Aldehyde (27) is obtained by allowing compound (22) to react with n-butyllithium and subsequently with N,N-dimethylformamide (DMF). Compound (1D) is prepared by allowing phosphorus ylide to react with aldehyde (27), in which the phosphorus ylide is generated by allowing phosphonium salt (28) to react with potassium tert-butoxide. A cis isomer is generated depending on reaction conditions, and therefore the cis isomer is isomerized into a trans isomer according to a publicly known method, when necessary.

(V) Formation of —CH$_2$CH$_2$—

Compound (1E) is prepared by hydrogenating compound (1D) in the presence of a catalyst such as palladium on carbon.

(VI) Formation of —C≡C—

Compound (29) is obtained by allowing compound (23) to react with 2-methyl-3-butyn-2-ol in the presence of a catalyst including dichloropalladium and copper iodide, and then deprotecting the resulting product under basic conditions. Compound (1F) is prepared by allowing compound (29) to react with compound (22) in the presence of a catalyst including dichlorobis(triphenylphosphine)palladium and copper halide.

(VII) Formation of —CH$_2$O— and —OCH$_2$—

Compound (30) is obtained by reducing compound (27) with sodium borohydride. Compound (31) is obtained by brominating the resulting product with hydrobromic acid. Compound (1G) is prepared by allowing compound (32) to react with compound (31) in the presence of potassium carbonate. A compound having —OCH$_2$— is also prepared according to the method.

(VIII) Formation of —CF═CF—

Compound (33) is obtained by treating compound (23) with n-butyllithium and then allowing the resulting treated material to react with tetrafluoroethylene. Compound (1H) is prepared by treating compound (22) with n-butyllithium and then allowing the resulting treated material to react with compound (33).

1-4-2. Formation of Ring A$^1$ and Ring A$^2$

Starting materials are marketed or preparation methods are well known for rings such as 1,4-cyclohexylene, 1,4-cyclohexenylene, 1,4-phenylene, 2-fluoro-1,4-phenylene, 2,3-difluoro-1,4-phenylene, tetrahydropyran-2,5-diyl and 1,3-dioxane-2,5-diyl.

1-4-3. Synthesis Examples

An example of a method for preparing compound (1) is as described below.

Compound (1-a) in which Y$^1$ in compound (1) is —CF$_2$H will be first described.

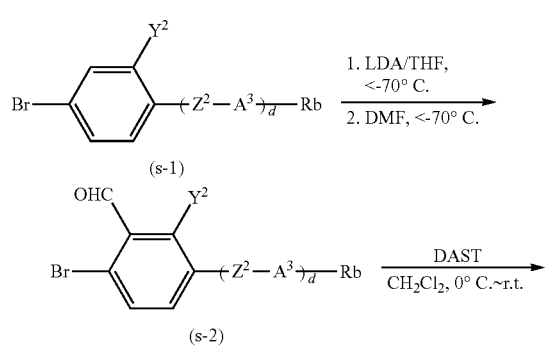

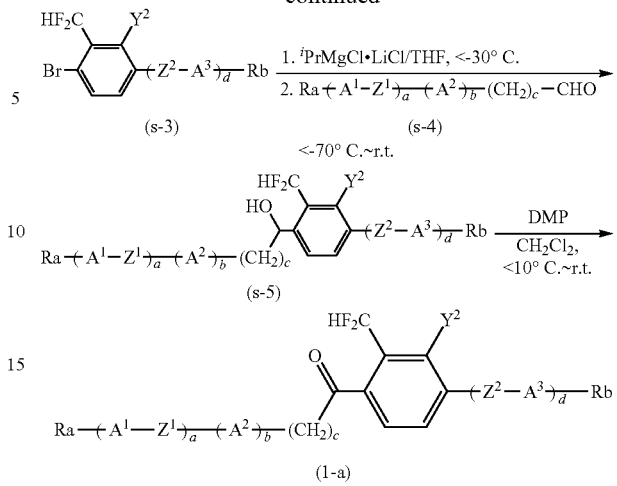

Aldehyde (s-2) is obtained by treating compound (s-1) obtained by a publicly known method with lithium diisopropylamide (LDA) and then adding N,N-dimethylformamide (DMF) to the resulting treated material. Next, (s-3) is obtained by treating compound (s-2) with a fluorinating agent such as (diethylamino)sulfur trifluoride (DAST). Next, (1-a) can be obtained by treating (s-3) with a THF solution of isopropylmagnesium bromide and lithium chloride, and then adding aldehyde (s-4) thereto to obtain alcohol (s-5), and then oxidizing the resulting product using Dess-Martin periodinane (DMP). In the compounds, Ra, Rb, ring A$^1$, ring A$^2$, ring A$^3$, Z$^1$, Z$^2$, Y$^2$, a, b, c and d are defined in a manner identical with the definitions in item 1.

Next, compound (1-b) in which Y$^1$ in compound (1) is —CF$_3$ will be described.

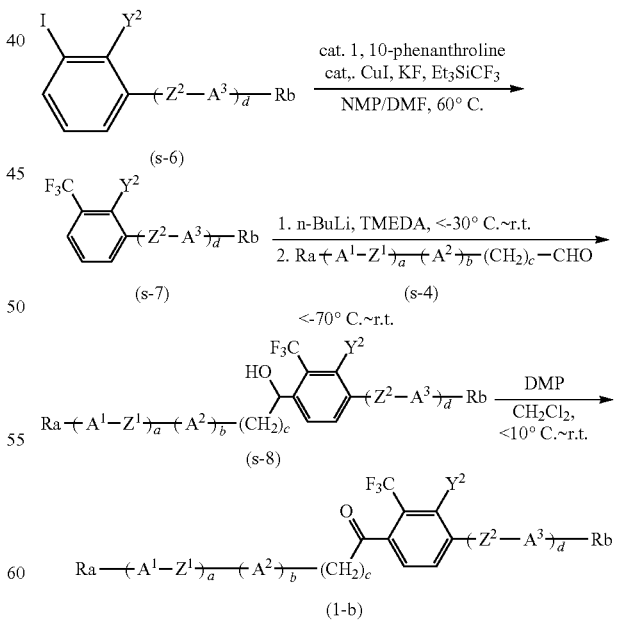

Compound (s-7) is obtained by treating compound (s-6) obtained by a publicly known method, in the presence of a catalyst amount of 1,10-phenanthroline, and a catalyst amount of copper iodide and potassium fluoride, with trifluoromethyltriethylsilane. Then, (1-b) can be obtained by treating compound (s-7) with s-butyllithium in the presence of tetramethylethylenediamine (TMEDA) and then adding aldehyde (s-4) thereto to obtain alcohol (s-8), and then oxidizing the resulting product using Dess-Martin periodinane (DMP). In the compounds, Ra, Rb, ring $A^1$, ring $A^2$, ring $A^3$, $Z^1$, $Z^2$, $Y^2$, a, b, c and d are defined in a manner identical with the definitions in item 1.

2. Composition (1)

Liquid crystal composition (1) of the invention will be described. Composition (1) contains at least one compound (1) as component A. Composition (1) may contain two or more compounds (1). A component in the liquid crystal compound may be compound (1) only. In order to develop excellent physical properties, composition (1) preferably contains at least one of compounds (1) in the range of approximately 1 to approximately 99% by weight. In a composition having a positive dielectric anisotropy, a preferred content of compound (1) is in the range of approximately 5 to approximately 60% by weight. In a composition having a negative dielectric anisotropy, a preferred content of compound (1) is approximately 30% by weight or less. Composition (1) may also contain compound (1) and various liquid crystal compounds that are not described herein.

A preferred composition contains a compound selected from components B, C, D and E shown below. When composition (1) is prepared, components can be selected, for example, by taking dielectric anisotropy of compound (1) into consideration. A composition prepared by suitably selecting the components has a high maximum temperature of a nematic phase, a low minimum temperature of the nematic phase, a small viscosity, a suitable optical anisotropy, a large dielectric anisotropy and a suitable elastic constant.

Component B includes compounds (2) to (4). Component C includes compound (5). Component D includes compounds (6) to (12). Component E includes compounds (13) to (15). The components will be described in the order.

Component B includes a compound having a halogen-containing group or a fluorine-containing group at a right terminal Specific preferred examples of component B include compounds (2-1) to (2-16), compounds (3-1) to (3-113) and compounds (4-1) to (4-57).

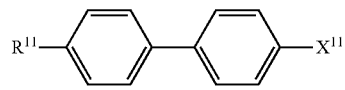

(2-1)

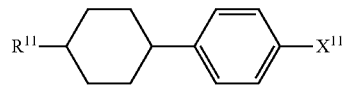

(2-2)

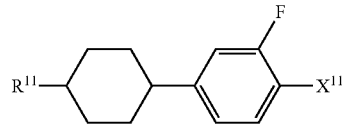

(2-3)

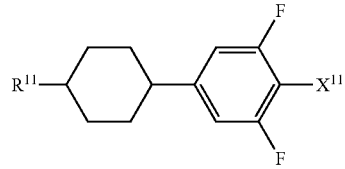

(2-4)

-continued

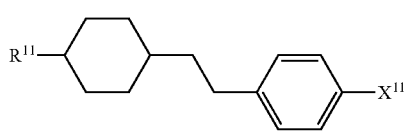

(2-5)

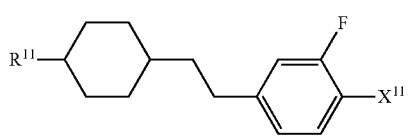

(2-6)

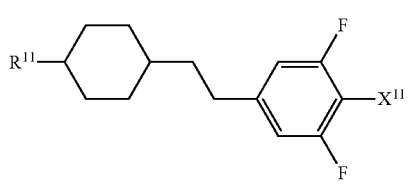

(2-7)

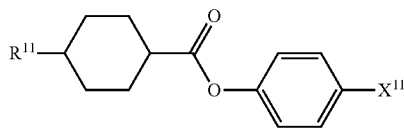

(2-8)

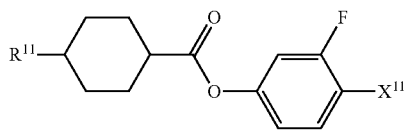

(2-9)

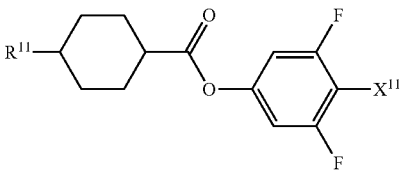

(2-10)

(2-11)

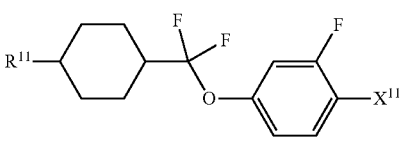

(2-12)

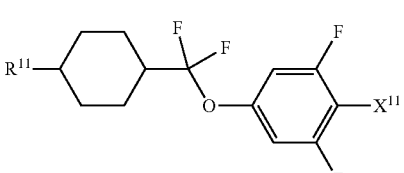

(2-13)

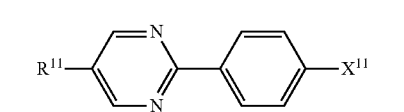

(2-14)

(2-15) 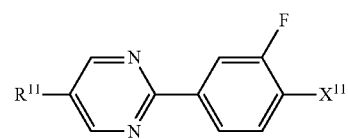
(2-16) 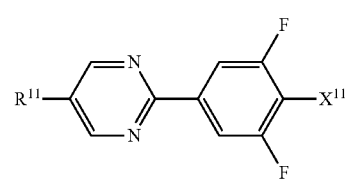
(3-1) 
(3-2) 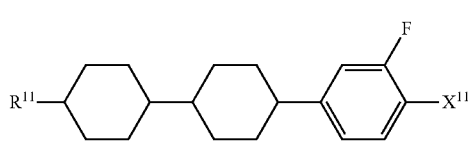
(3-3) 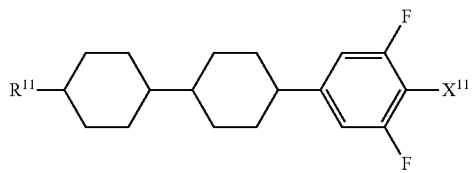
(3-4) 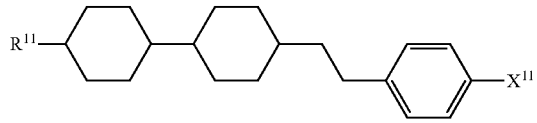
(3-5) 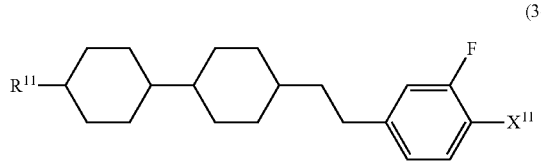
(3-6) 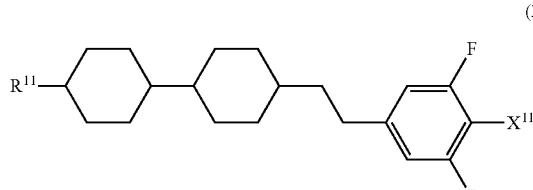
(3-7) 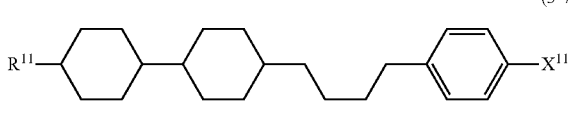
(3-8) 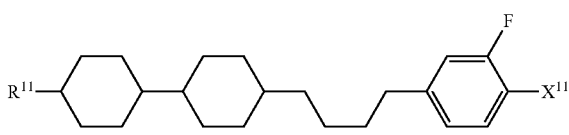
(3-9) 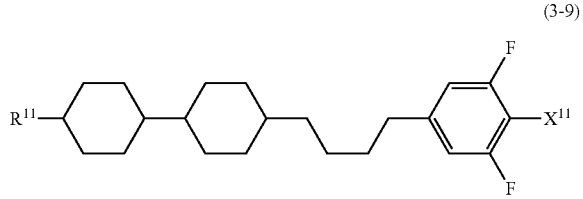
(3-10) 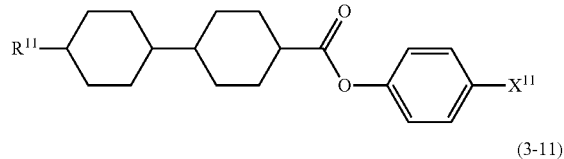
(3-11) 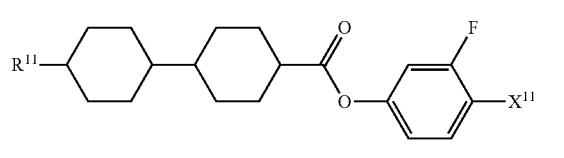
(3-12) 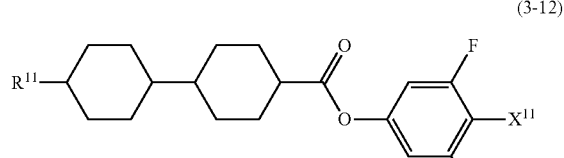
(3-13) 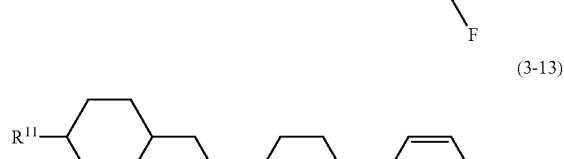
(3-14) 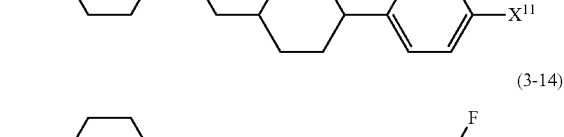
(3-15) 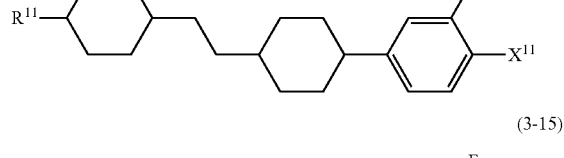
(3-16) 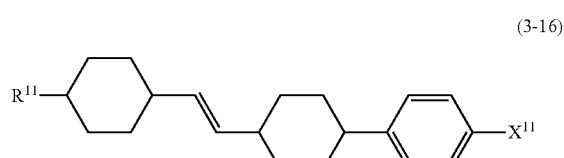
(3-17) 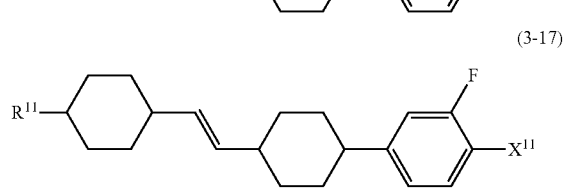

(3-18)
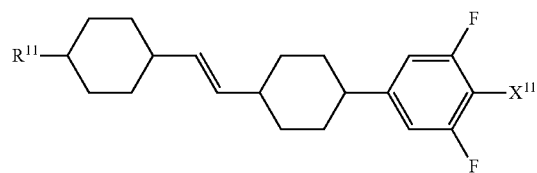
(3-19)
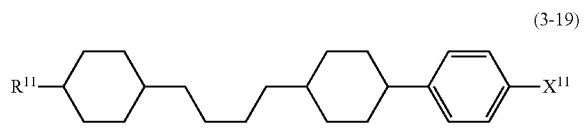
(3-20)
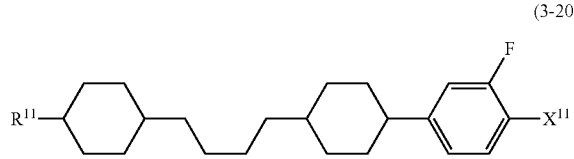
(3-21)
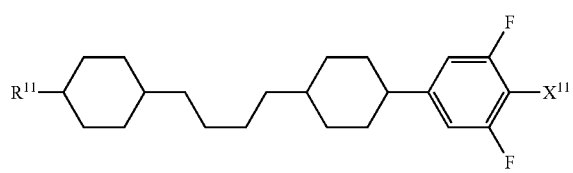
(3-22)
(3-23)
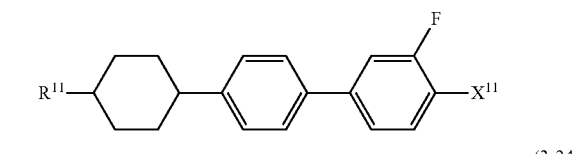
(3-24)
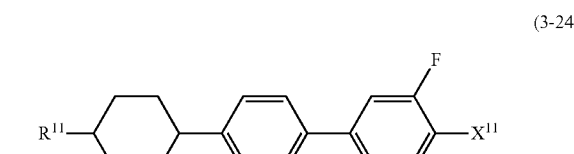
(3-25)
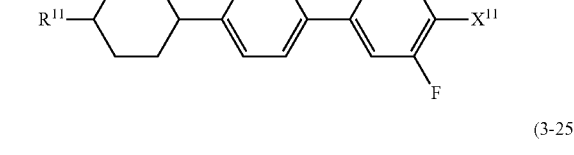
(3-26)
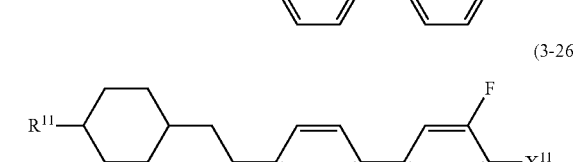
(3-27)
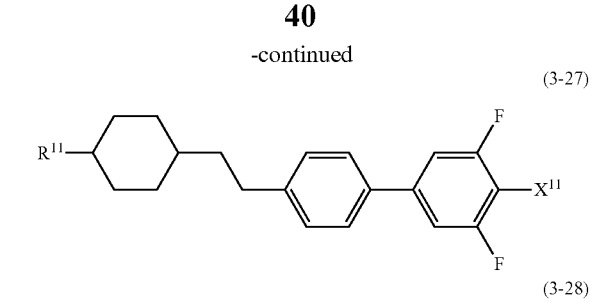
(3-28)
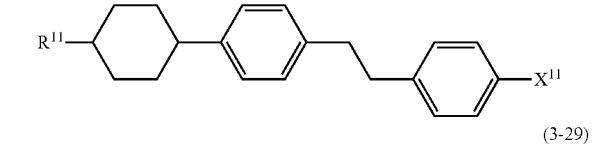
(3-29)
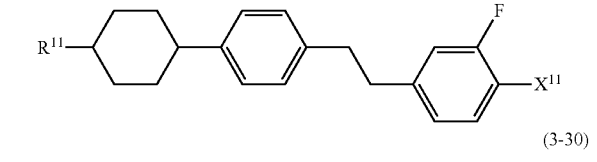
(3-30)
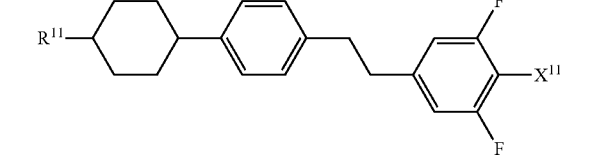
(3-31)
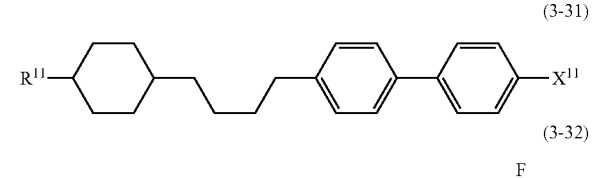
(3-32)
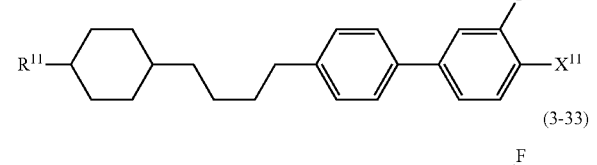
(3-33)
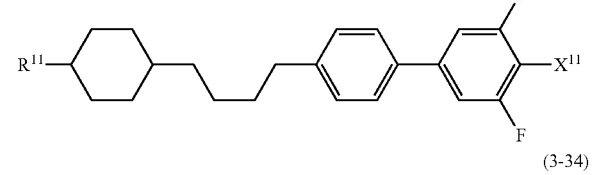
(3-34)
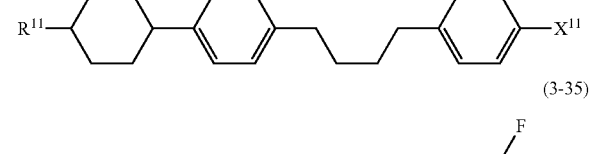
(3-35)
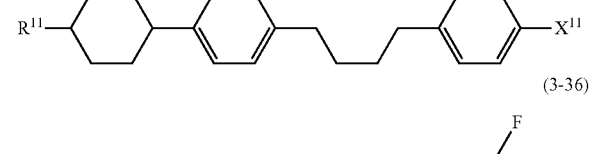
(3-36)
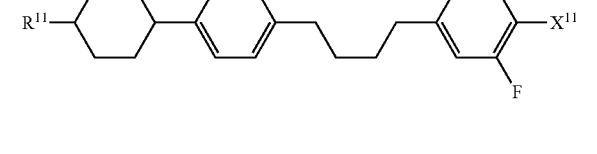

(3-37) 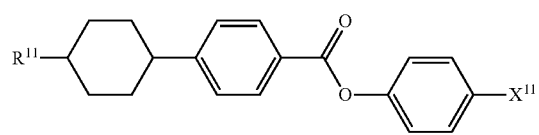
(3-38) 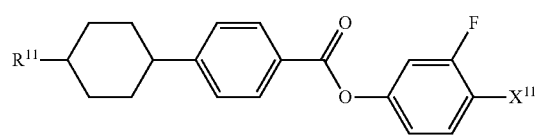
(3-39) 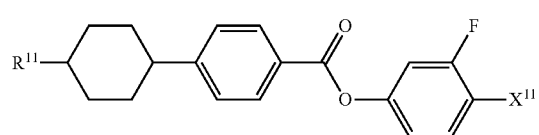
(3-40) 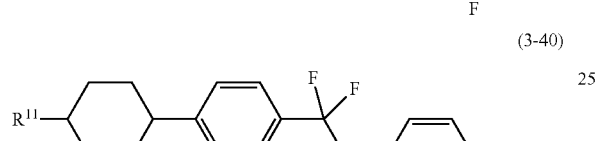
(3-41) 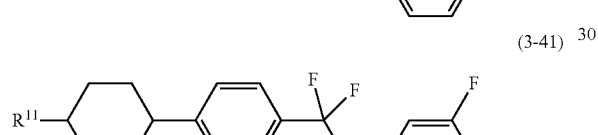
(3-42) 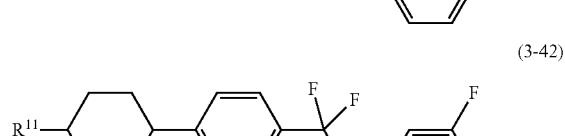
(3-43) 
(3-44) 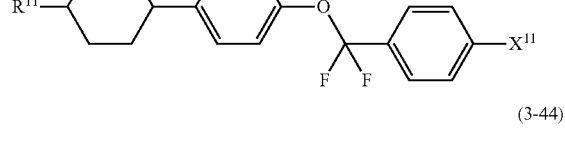
(3-45) 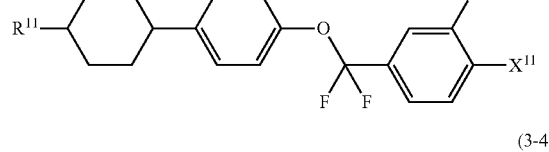
(3-46) 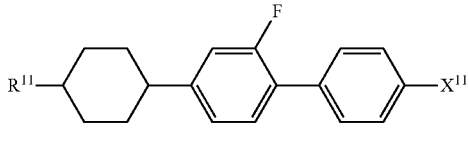
(3-47) 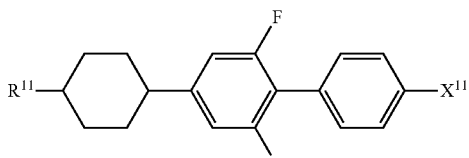
(3-48) 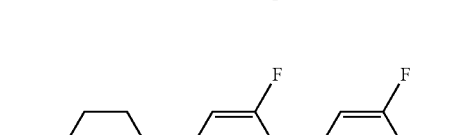
(3-49) 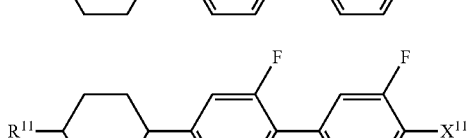
(3-50) 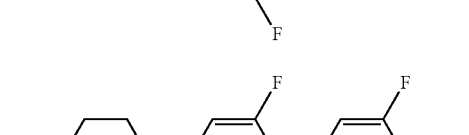
(3-51) 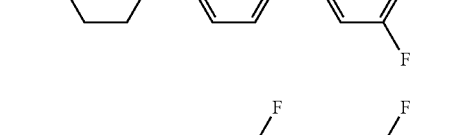
(3-52) 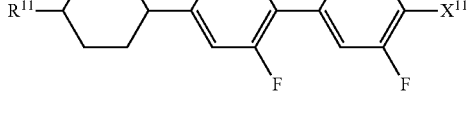
(3-53) 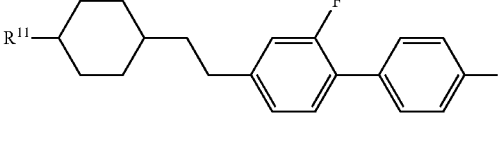
(3-54) 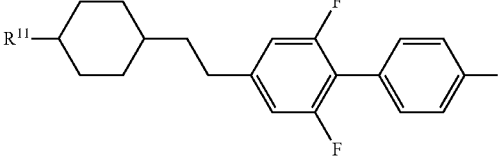

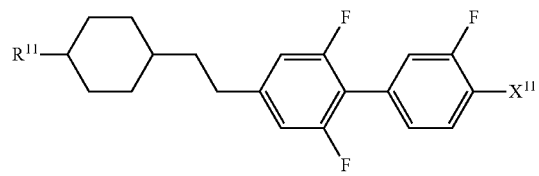
(3-55)
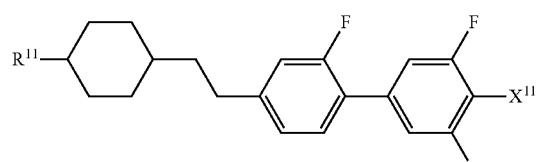
(3-56)
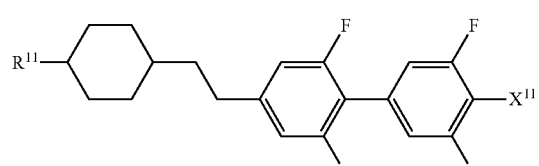
(3-57)
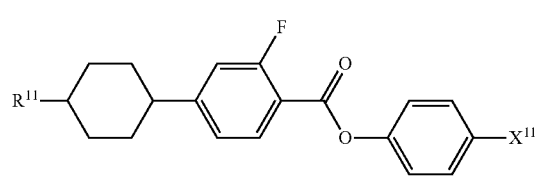
(3-58)
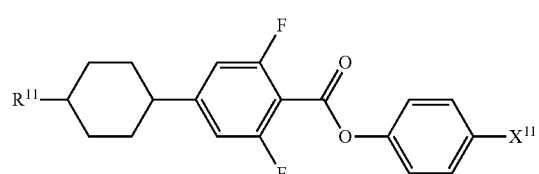
(3-59)
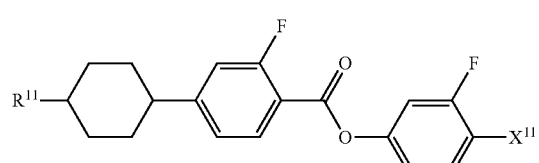
(3-60)
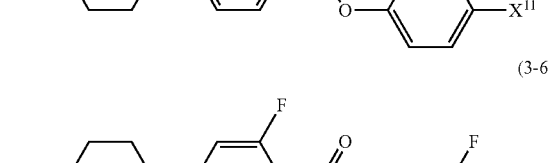
(3-61)
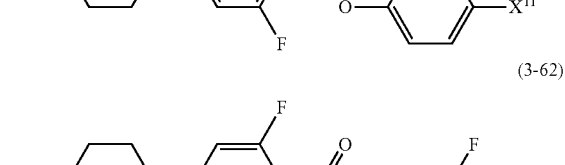
(3-62)
(3-63)
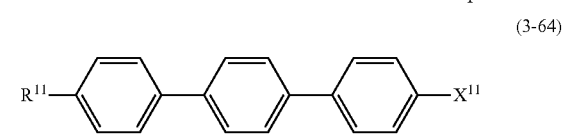
(3-64)
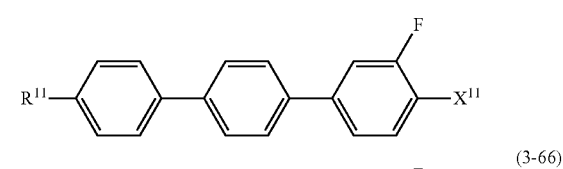
(3-65)
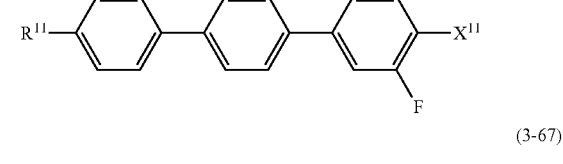
(3-66)
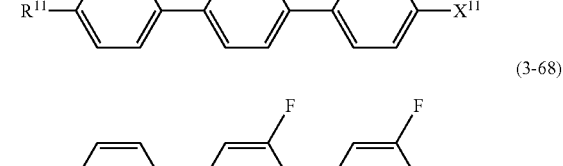
(3-67)
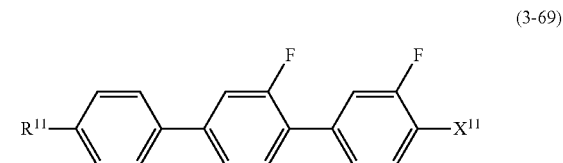
(3-68)
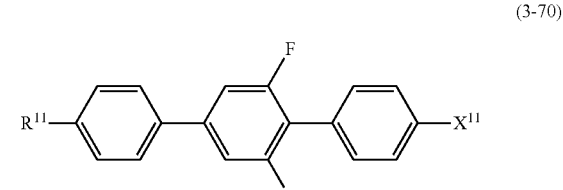
(3-69)
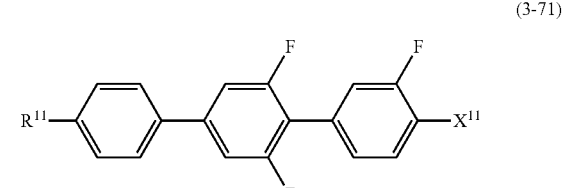
(3-70)
(3-71)

(3-72) 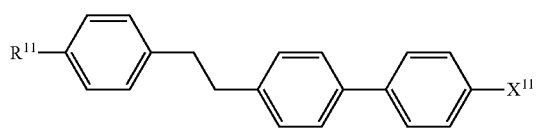
(3-73) 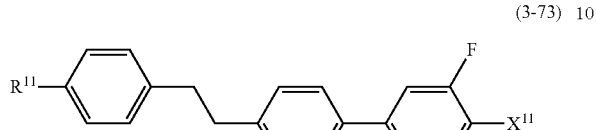
(3-74) 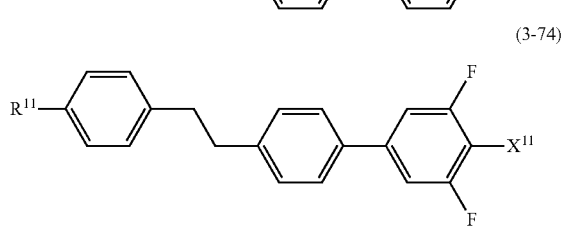
(3-75) 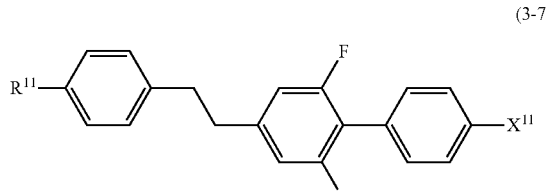
(3-76) 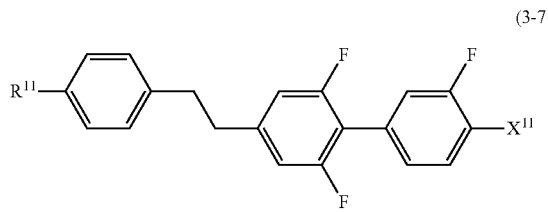
(3-77) 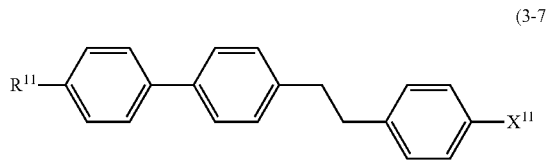
(3-78) 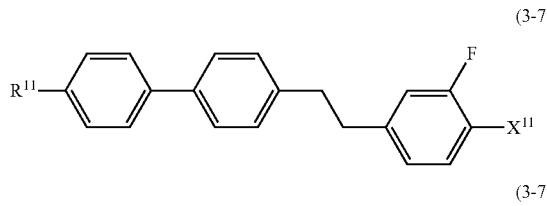
(3-79) 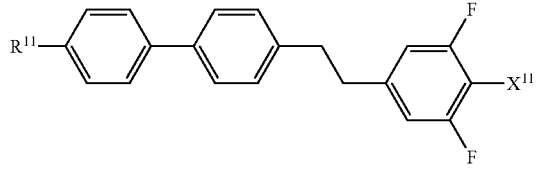
(3-80) 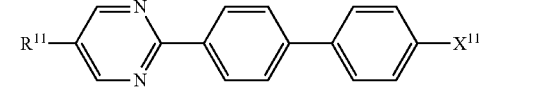
(3-81) 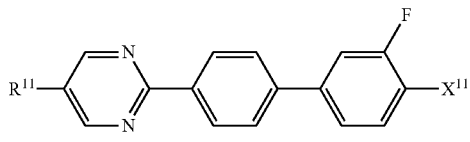
(3-82) 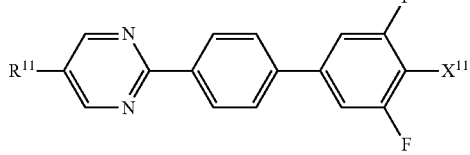
(3-83) 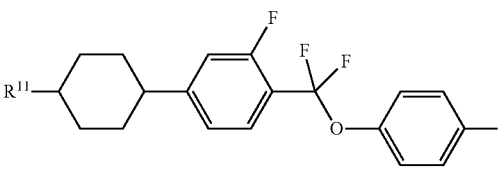
(3-84) 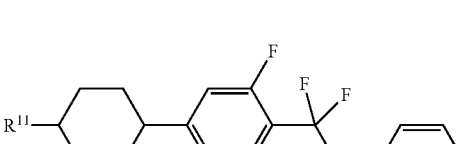
(3-85) 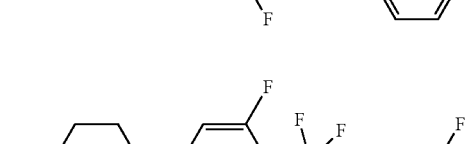
(3-86) 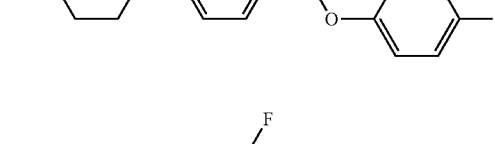
(3-87) 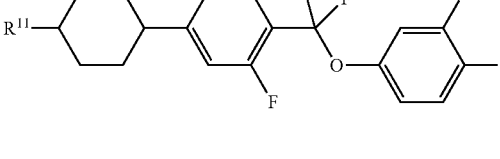
(3-88) 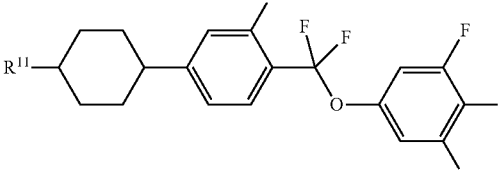
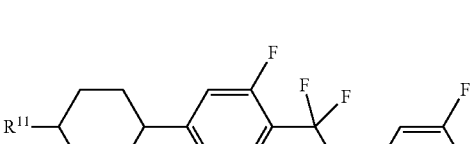

(3-89)
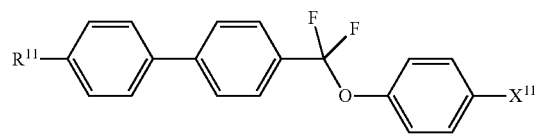
(3-90)
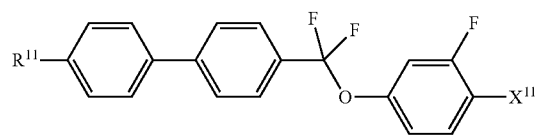
(3-91)
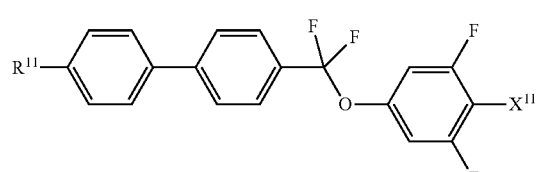
(3-92)
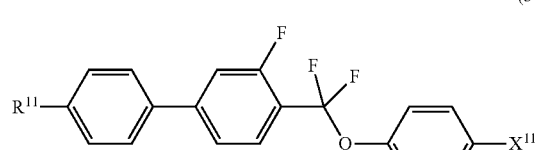
(3-93)
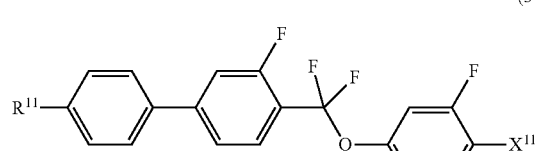
(3-94)
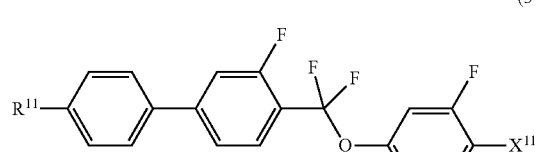
(3-95)
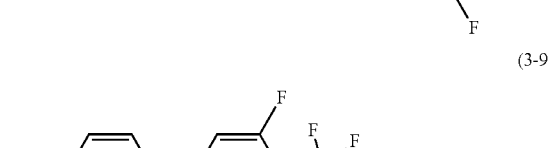
(3-96)
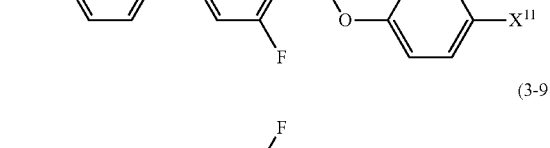
(3-97)
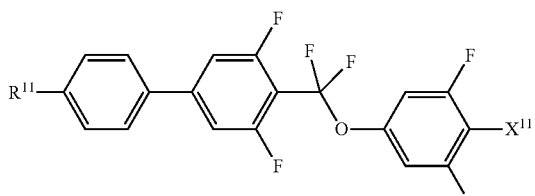
(3-98)
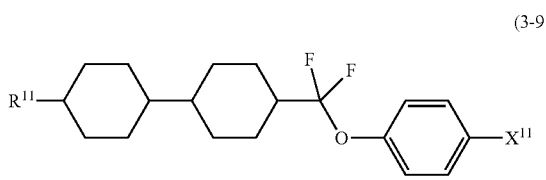
(3-99)
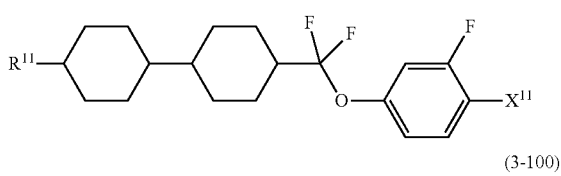
(3-100)
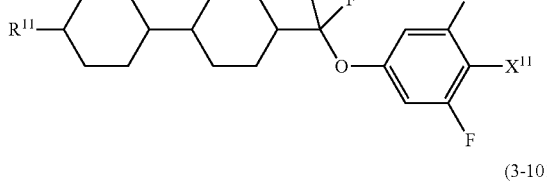
(3-101)
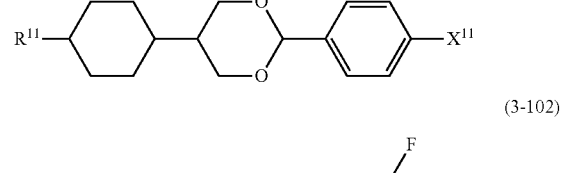
(3-102)
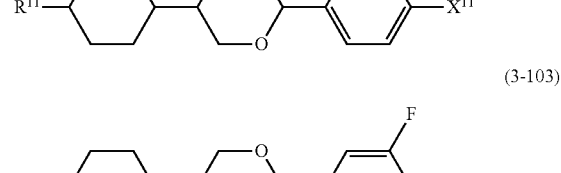
(3-103)
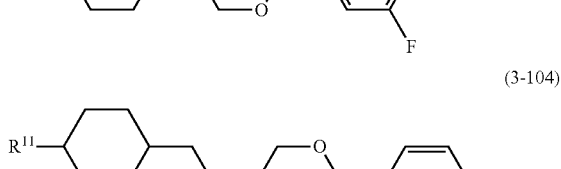
(3-104)
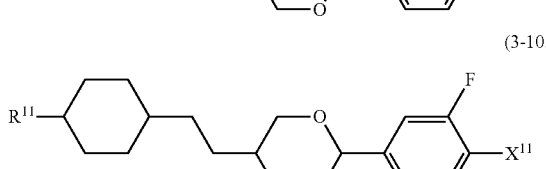
(3-105)
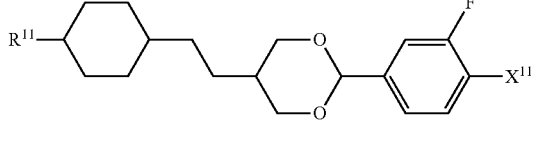

(3-106) 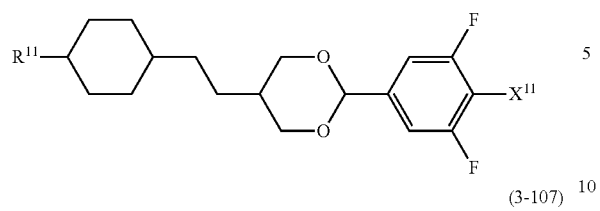
(3-107) 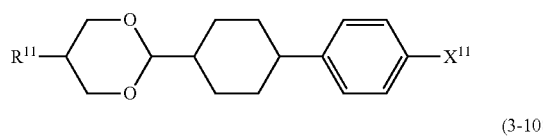
(3-108) 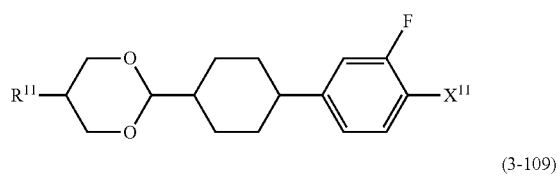
(3-109) 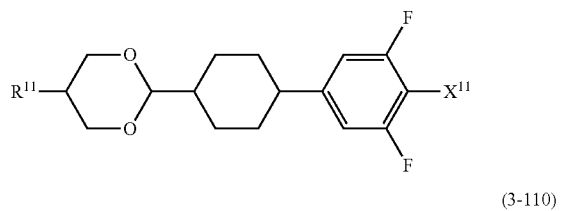
(3-110) 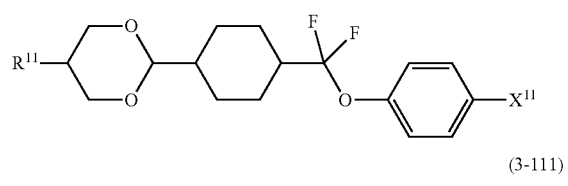
(3-111) 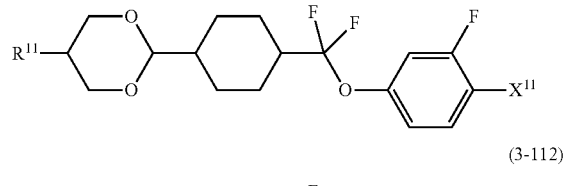
(3-112) 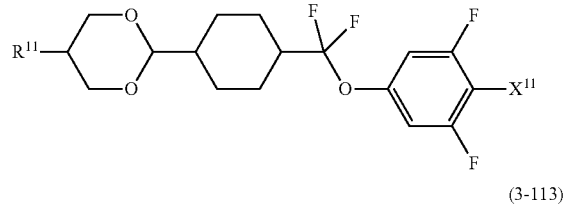
(3-113) 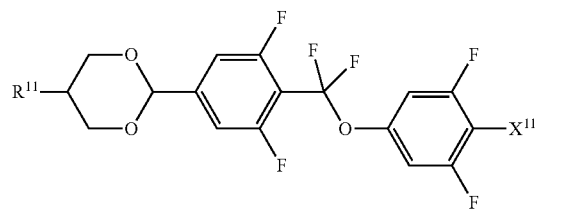
(4-1) 
(4-2) 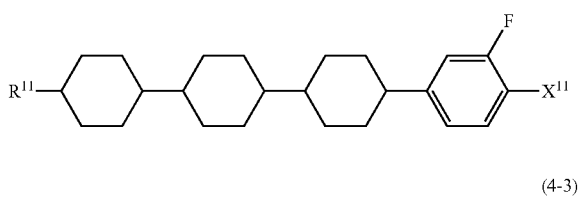
(4-3) 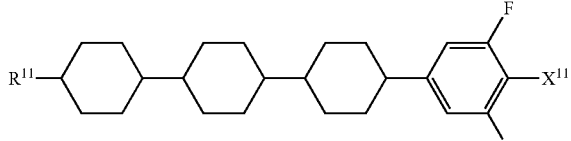
(4-4) 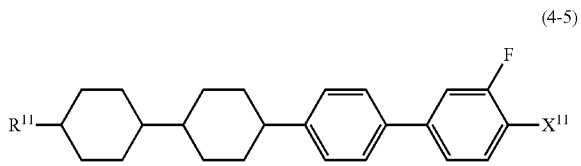
(4-5) 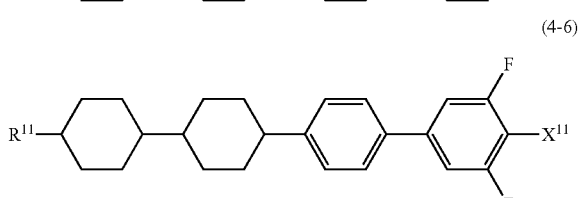
(4-6) 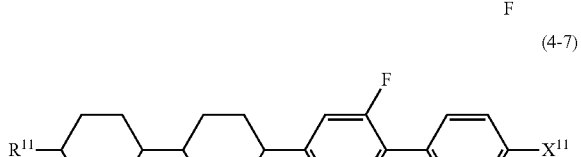
(4-7) 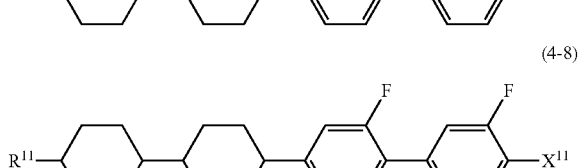
(4-8) 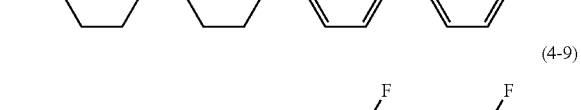
(4-9) 
(4-10) 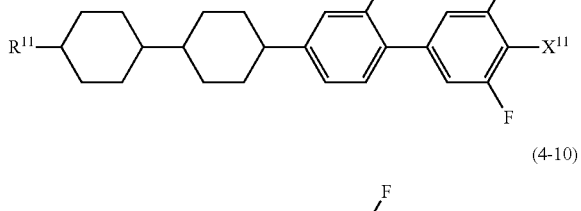

(4-11)
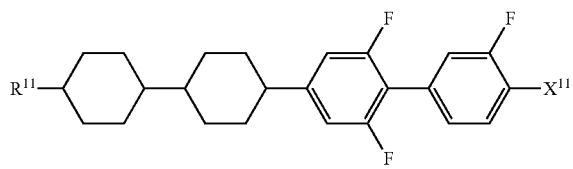
(4-12)
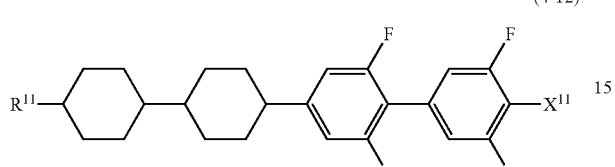
(4-13)
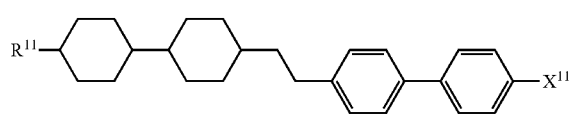
(4-14)
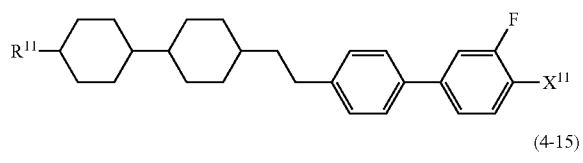
(4-15)
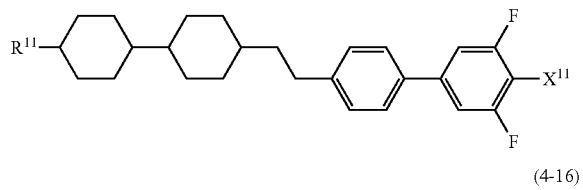
(4-16)
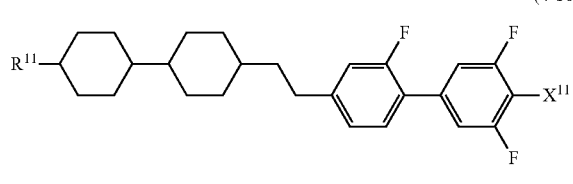
(4-17)
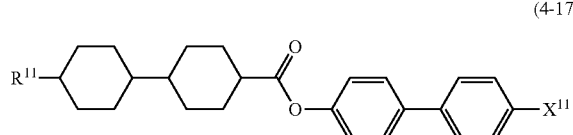
(4-18)
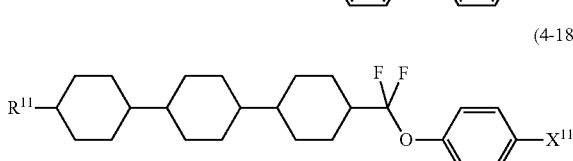
(4-19)
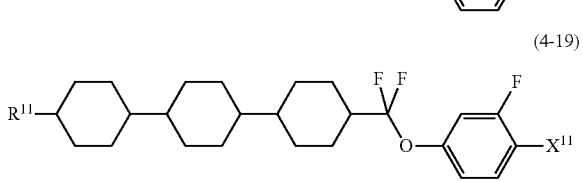
(4-20)
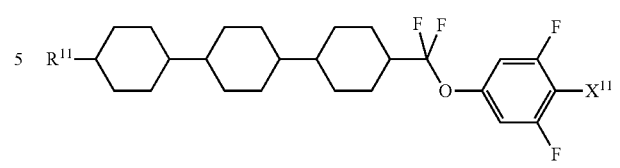
(4-21)
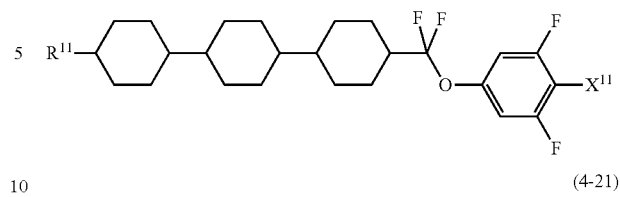
(4-22)
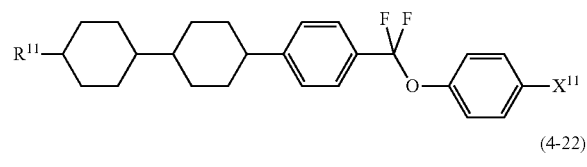
(4-23)
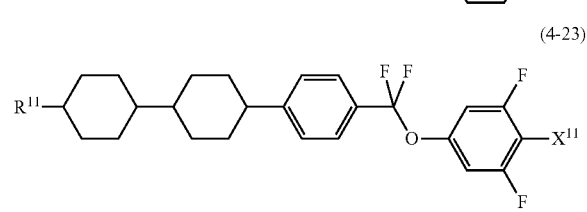
(4-24)
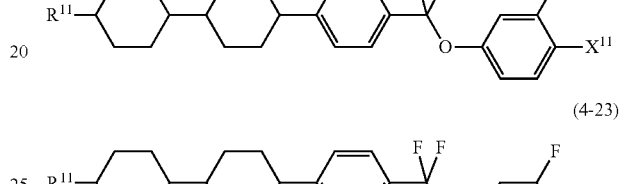
(4-25)
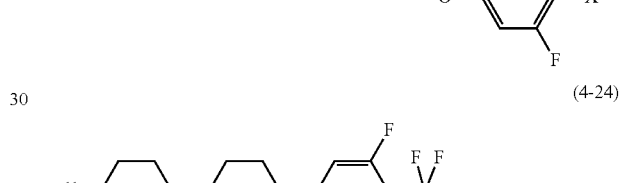
(4-26)
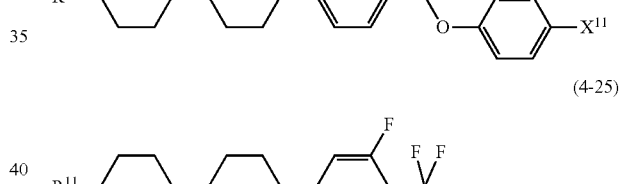
(4-27)
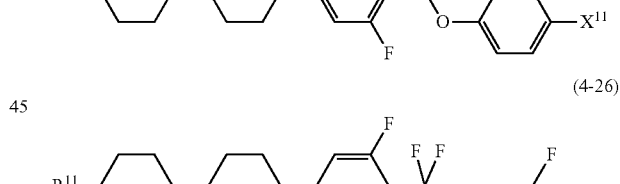
(4-28)
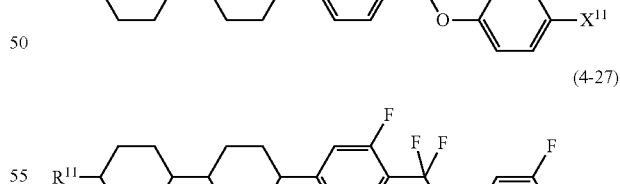

(4-29)
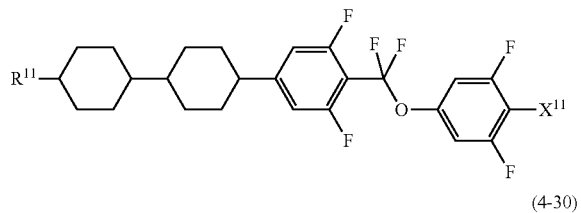
(4-30)
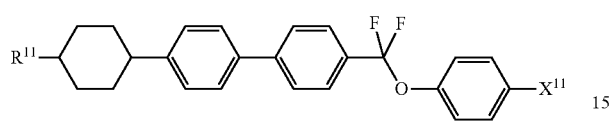
(4-31)
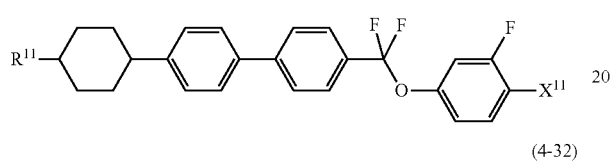
(4-32)
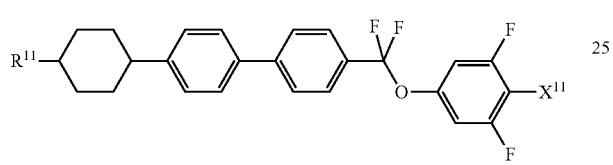
(4-33)
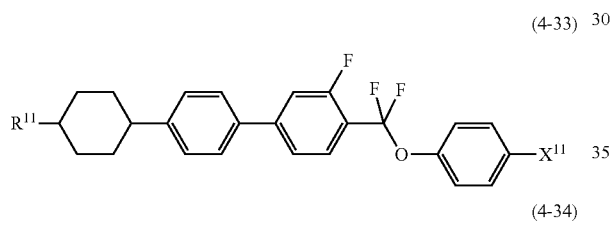
(4-34)
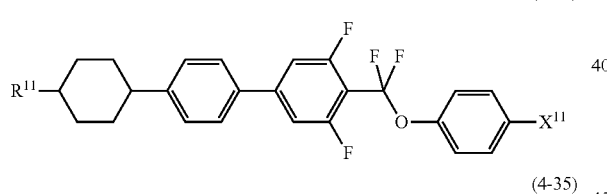
(4-35)
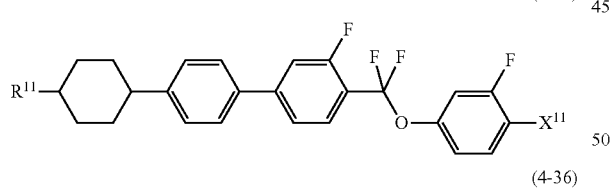
(4-36)
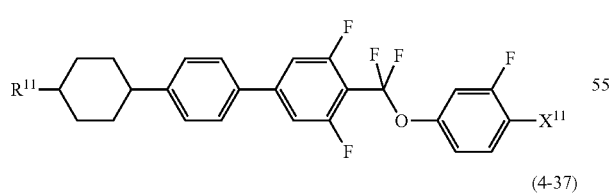
(4-37)
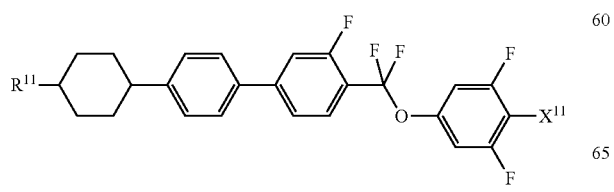
(4-38)
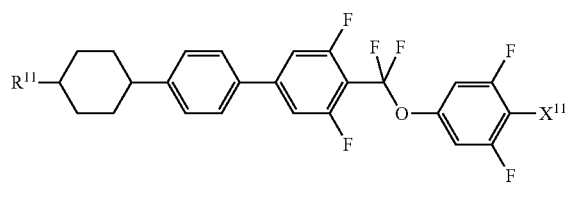
(4-39)
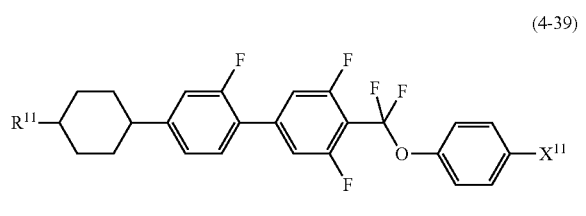
(4-40)
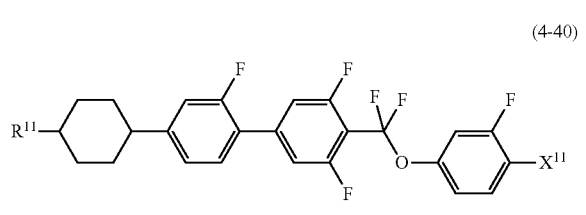
(4-41)
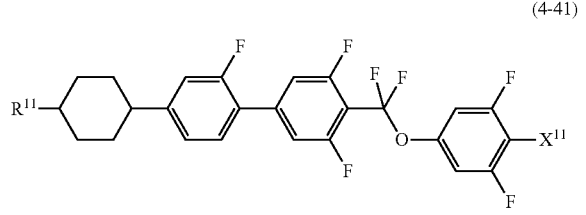
(4-42)
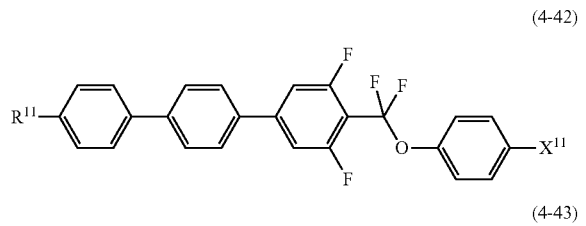
(4-43)
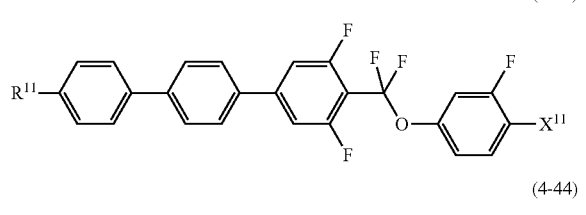
(4-44)
(4-45)
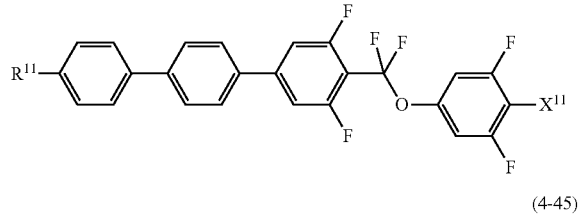

(4-46)
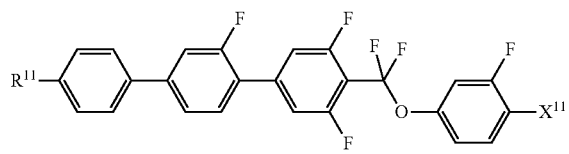

(4-47)
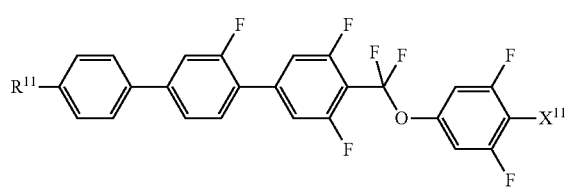

(4-48)
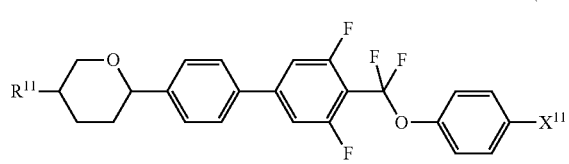

(4-49)
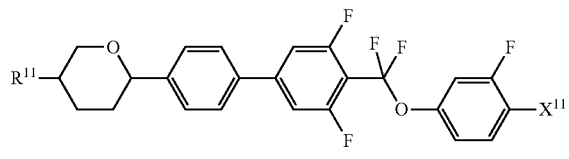

(4-50)
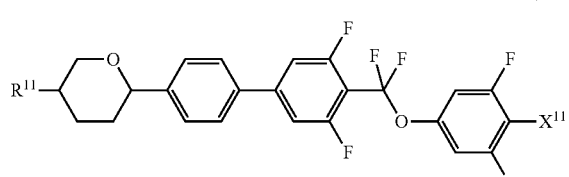

(4-51)
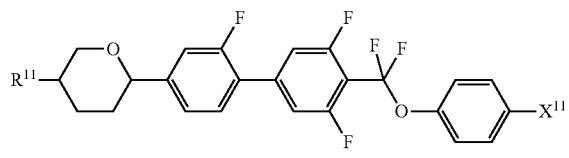

(4-52)
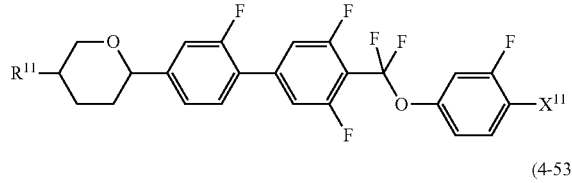

(4-53)
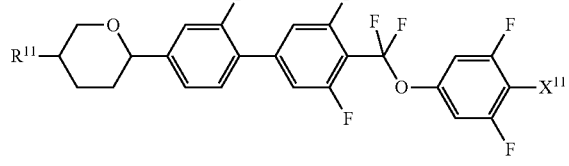

(4-54)
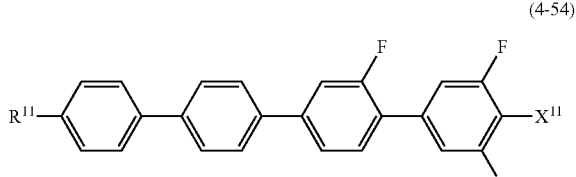

(4-55)
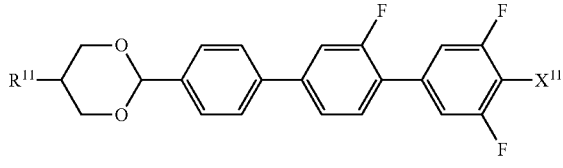

(4-56)
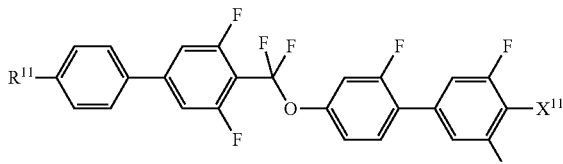

(4-57)
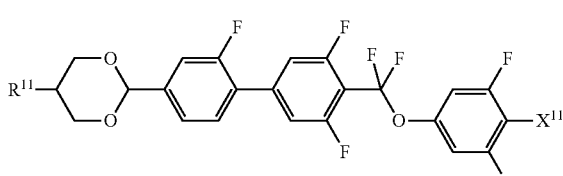

In the compounds (component B), $R^{11}$ and $X^{11}$ are defined in a manner identical with the definitions in formulas (2) to (4) described in item 12.

Component B has the positive dielectric anisotropy, and superb stability to heat, light and so forth, and therefore is used for preparing a composition for a TFT mode or a PSA mode. A content of component B is suitably in the range of approximately 1 to approximately 99% by weight, preferably, approximately 10 to approximately 97% by weight, and further preferably, approximately 40 to approximately 95% by weight, based on the total weight of the liquid crystal composition. Viscosity of the composition can be adjusted by further adding compounds (12) to (14) (Component E).

Component C includes compound (5) in which a right terminal group is —C≡N or —C≡C—C≡N. Preferred examples of component C include compounds (5-1) to (5-64).

(5-1)
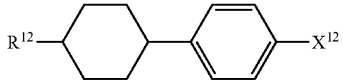

(5-2)
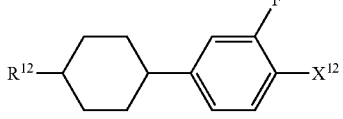

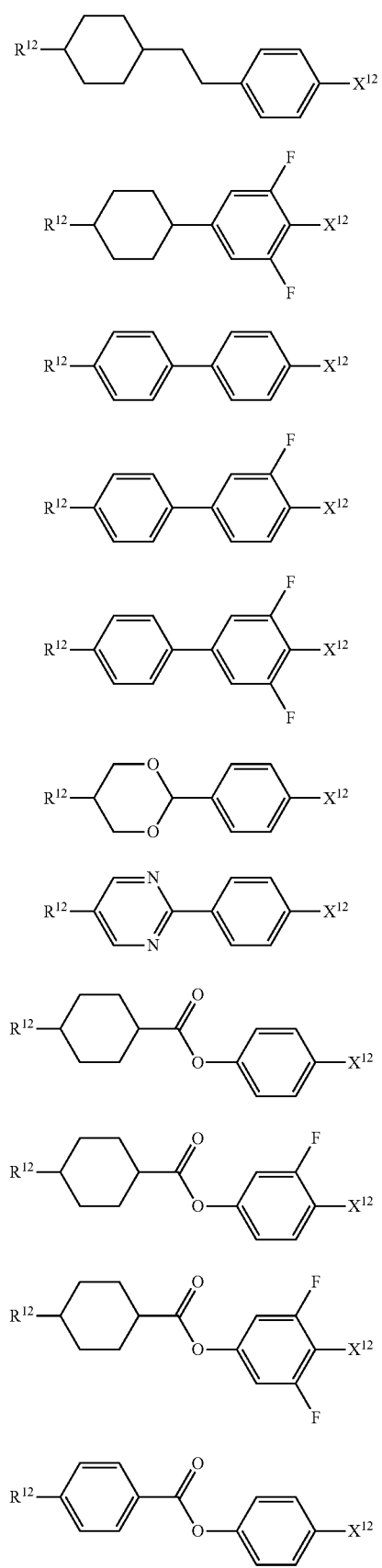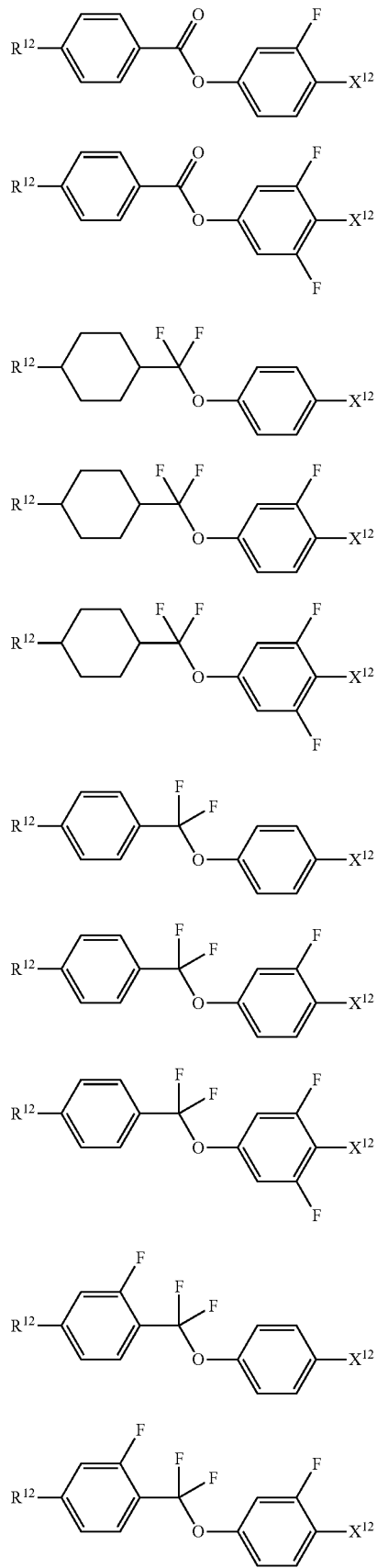

(5-24) 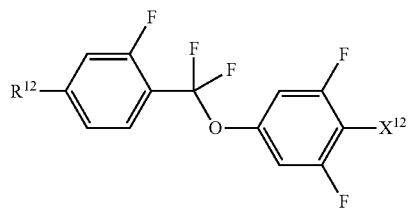
(5-25) 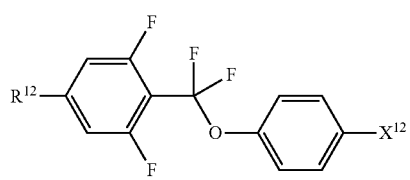
(5-26) 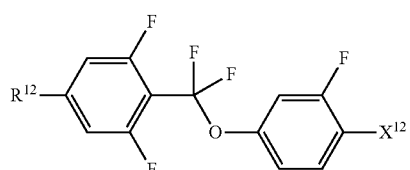
(5-27) 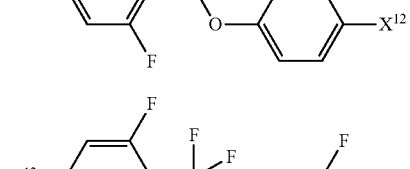
(5-28) 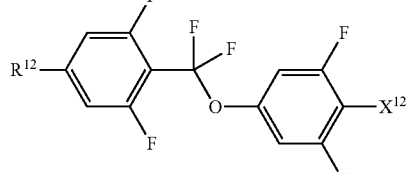
(5-29) 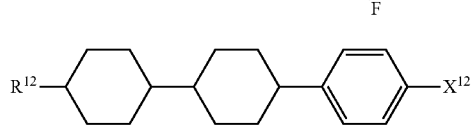
(5-30) 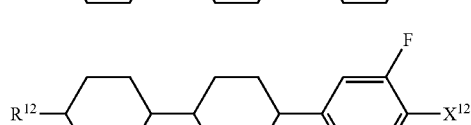
(5-31) 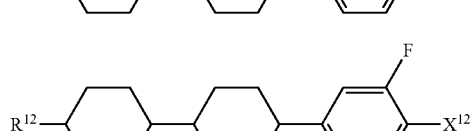
(5-32) 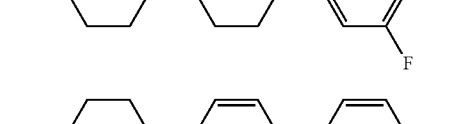
(5-33) 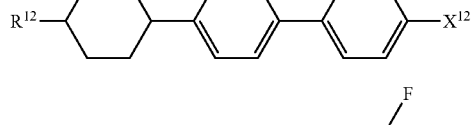
(5-34) 
(5-35) 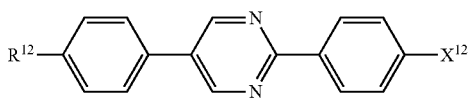
(5-36) 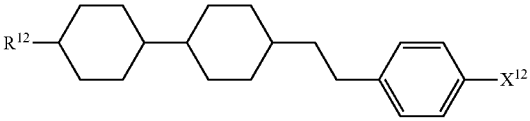
(5-37) 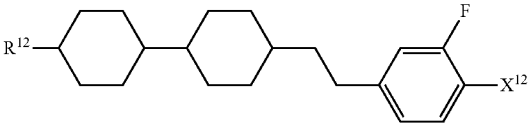
(5-38) 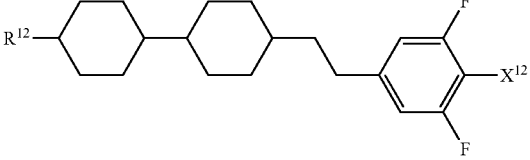
(5-39) 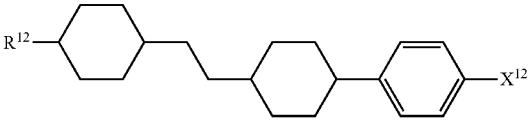
(5-40) 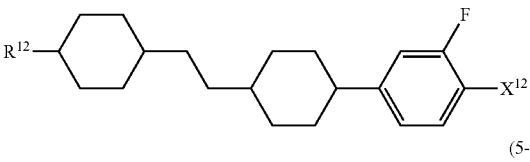
(5-41) 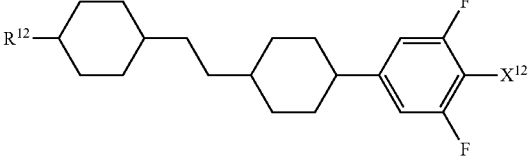
(5-42) 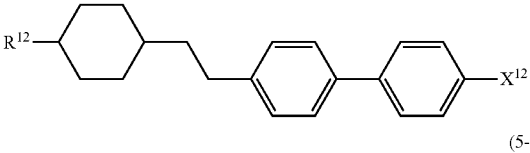
(5-43) 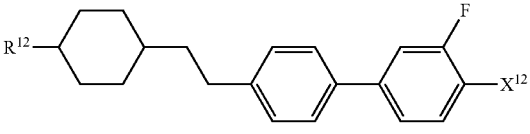

(5-44)
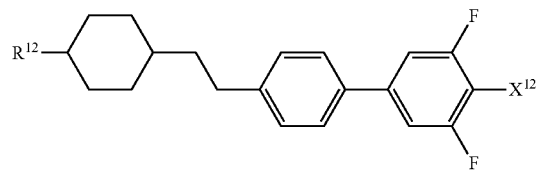
(5-45)
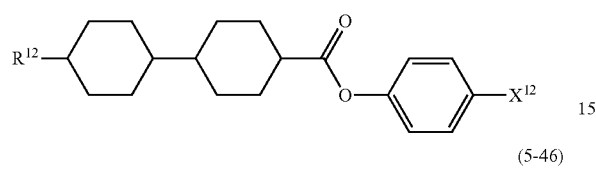
(5-46)
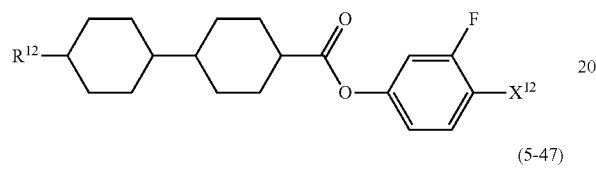
(5-47)
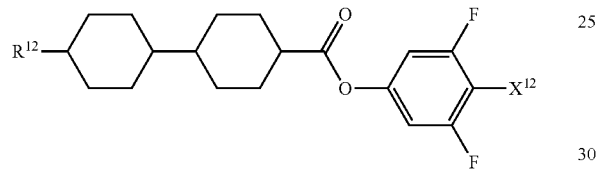
(5-48)
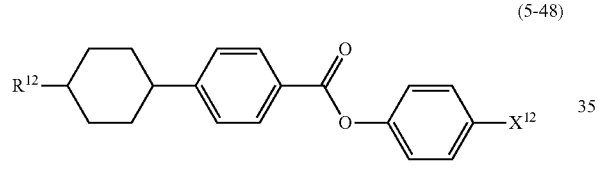
(5-49)
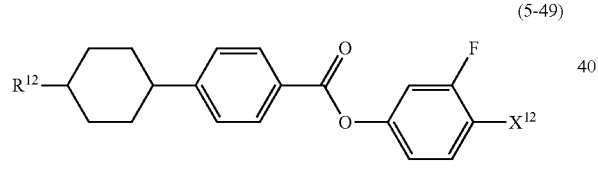
(5-50)
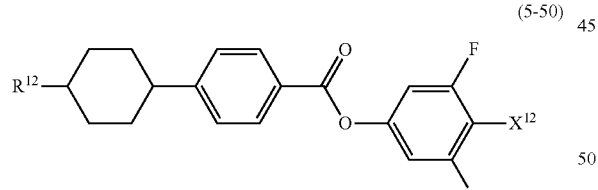
(5-51)
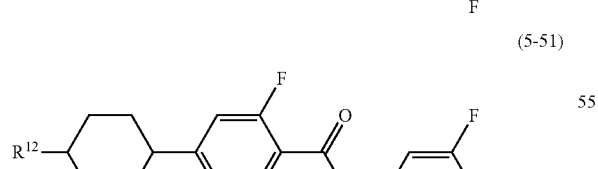
(5-52)
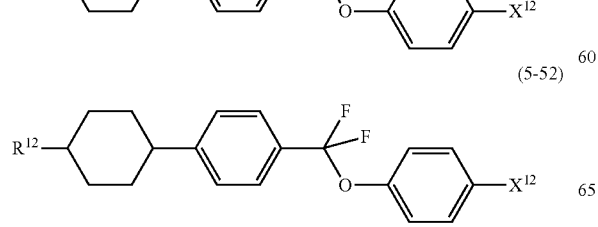
(5-53)
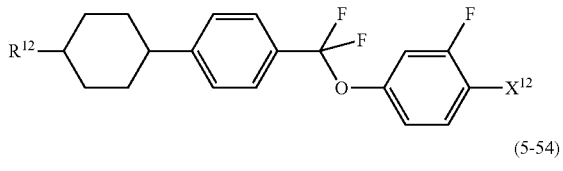
(5-54)
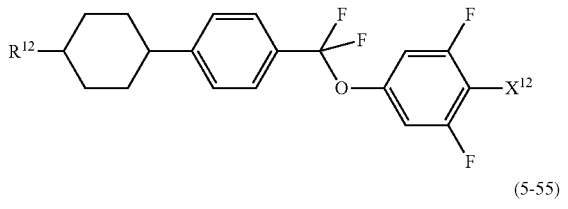
(5-55)
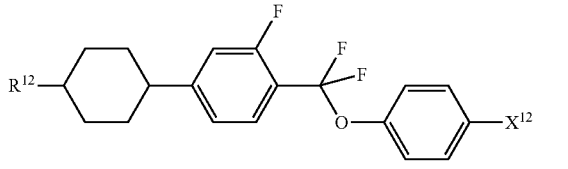
(5-56)
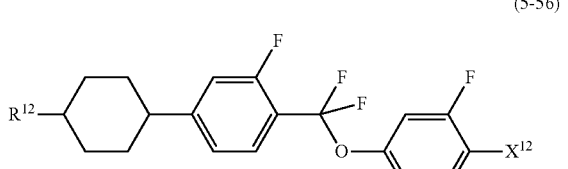
(5-57)
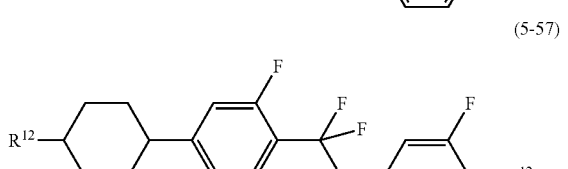
(5-58)
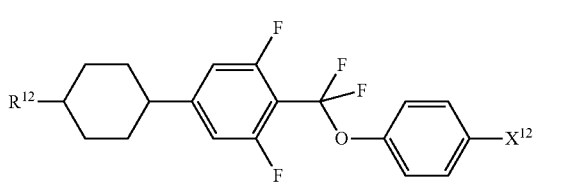
(5-59)
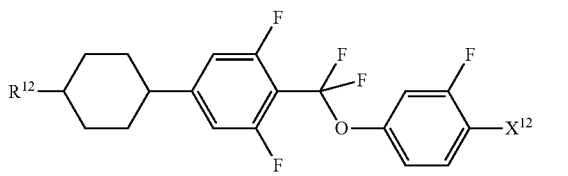
(5-60)
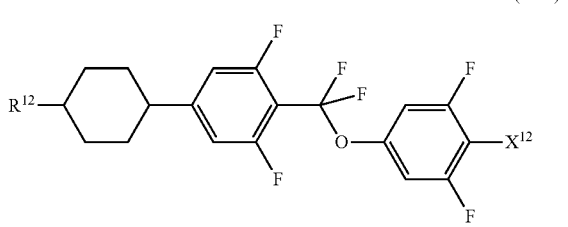

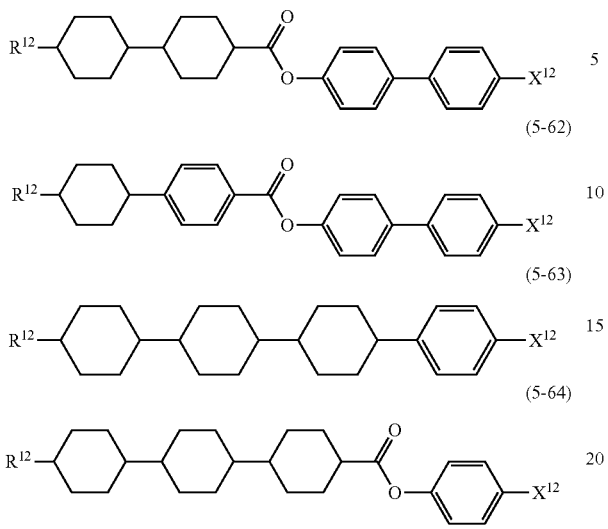

In the compounds (component C), $R^{12}$ and $X^{12}$ are defined in a manner identical with the definition in formula (5) described in item 13.

Component C has the positive dielectric anisotropy and a value thereof is large, and therefore is mainly used for preparing a composition for an STN mode, a TN mode or the PSA mode. Dielectric anisotropy of the composition can be increased by adding component C. Component C is effective in extending the temperature range of the liquid crystal phase, adjusting the viscosity or adjusting the optical anisotropy. Component C is also useful for adjusting a voltage-transmittance curve of the device.

When a composition for the STN mode or the TN mode is prepared, a content of component C is suitably in the range of approximately 1 to approximately 99% by weight, preferably, in the range of approximately 10 to approximately 97% by weight, and further preferably, in the range of approximately 40 to approximately 95% by weight, based on the total weight of the composition. In the composition, the temperature range of the liquid crystal phase, the viscosity, the optical anisotropy, the dielectric anisotropy and so forth can be adjusted by adding component E.

Component D includes compounds (6) to (12). The compounds have a benzene ring in which replacement in lateral positions is made by two halogen atoms, such as 2,3-difluoro-1,4-phenylene. Specific preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3).

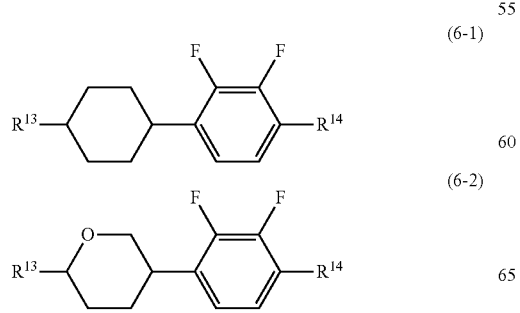

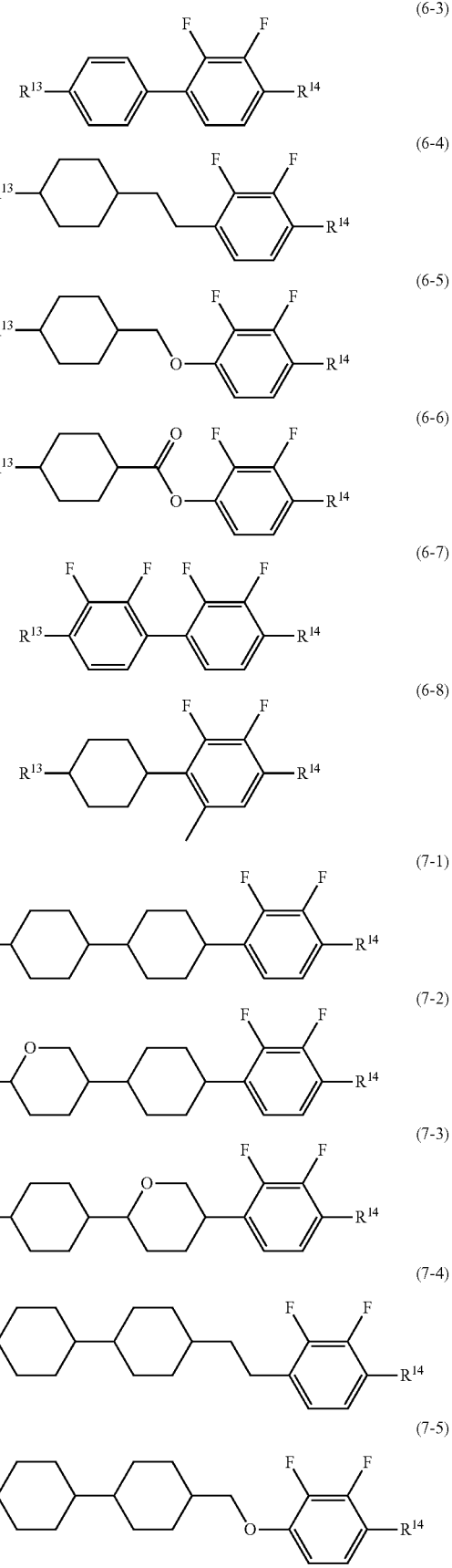

(7-6) 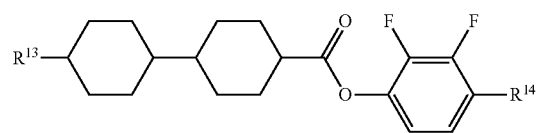
(7-7) 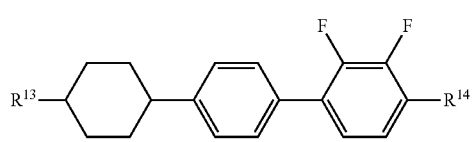
(7-8) 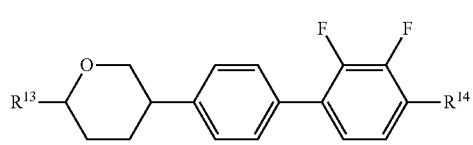
(7-9) 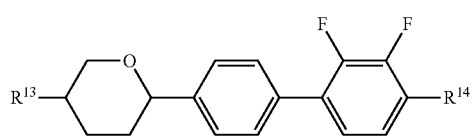
(7-10) 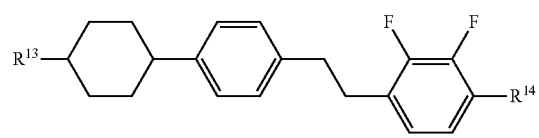
(7-11) 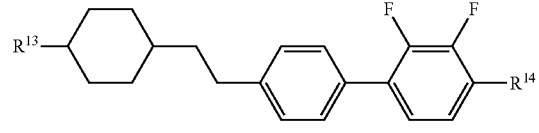
(7-12) 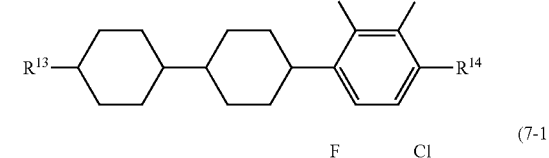
(7-13) 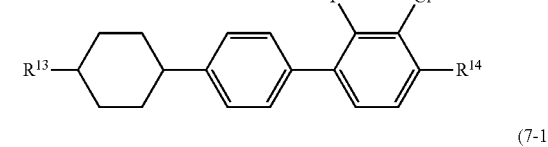
(7-14) 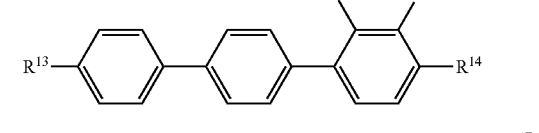
(7-15) 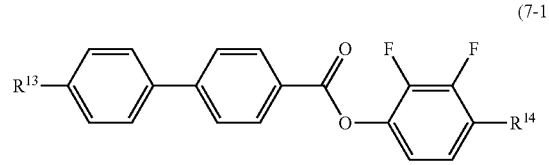
(7-16) 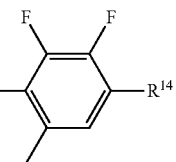
(7-17) 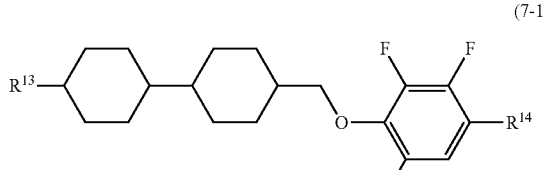
(8-1) 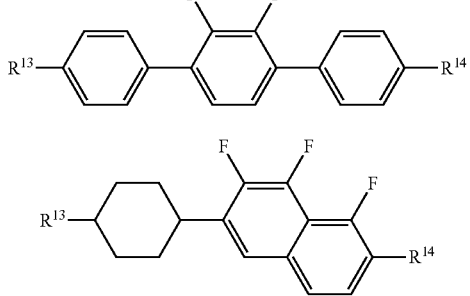
(9-1) 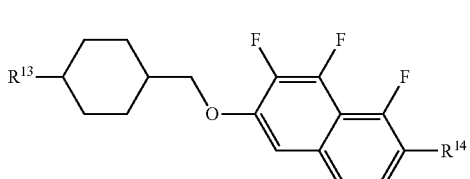
(9-2) 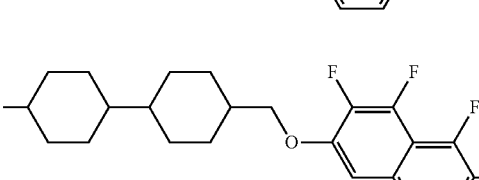
(9-3) 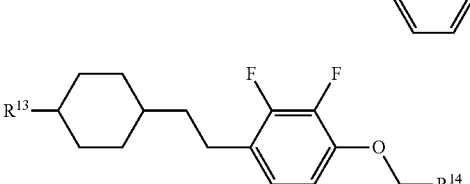
(10-1) 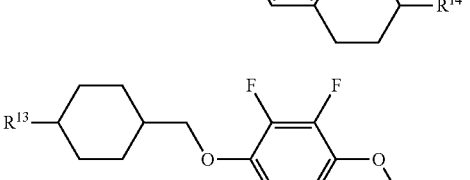
(10-2) 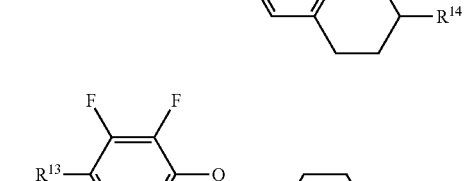
(10-3)

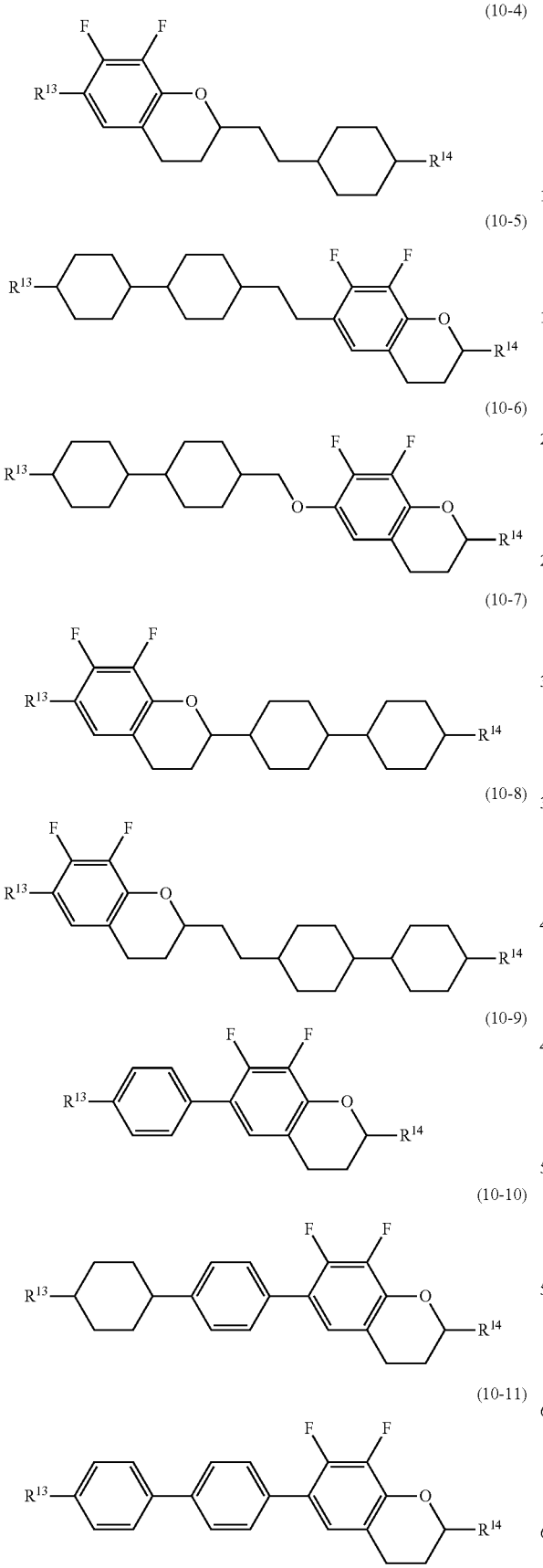

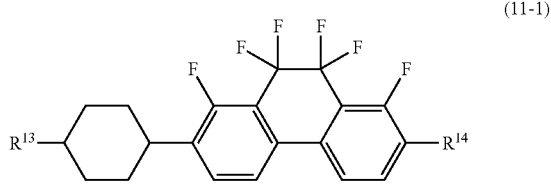

In the compounds (component D), $R^{13}$, $R^{14}$ and $R^{15}$ are defined in a manner identical with the definitions in formulas (6) to (12) described in item 9.

Component D includes a compound having the negative dielectric anisotropy. Component D is mainly used for preparing a composition for a VA mode or the PSA mode. Among types of component D, compound (6) includes a bicyclic compound, and therefore is effective mainly in adjusting the viscosity, the optical anisotropy or the dielectric anisotropy. Compounds (7) and (8) include a tricyclic compound, and therefore are effective in increasing the maximum temperature, the optical anisotropy or the dielectric anisotropy. Compounds (9) to (12) are effective in increasing the dielectric anisotropy.

When a liquid crystal composition for the VA mode or the PSA mode is prepared, a content of component D is preferably approximately 40% by weight or more, and further preferably, in the range of approximately 50 to approximately 95% by weight, based on the total weight of the composition. When component D is added to a composition having the positive dielectric anisotropy, a content of component D is preferably approximately 30% by weight or less based on the total weight of the composition. Addition of component D allows adjustment of the elastic constant of the composition and the voltage-transmittance curve of the device.

Component E includes a compound in which two terminal groups are alkyl or the like. Specific preferred examples of component E include compounds (13-1) to (13-11), compounds (14-1) to (14-19) and compounds (15-1) to (15-7).

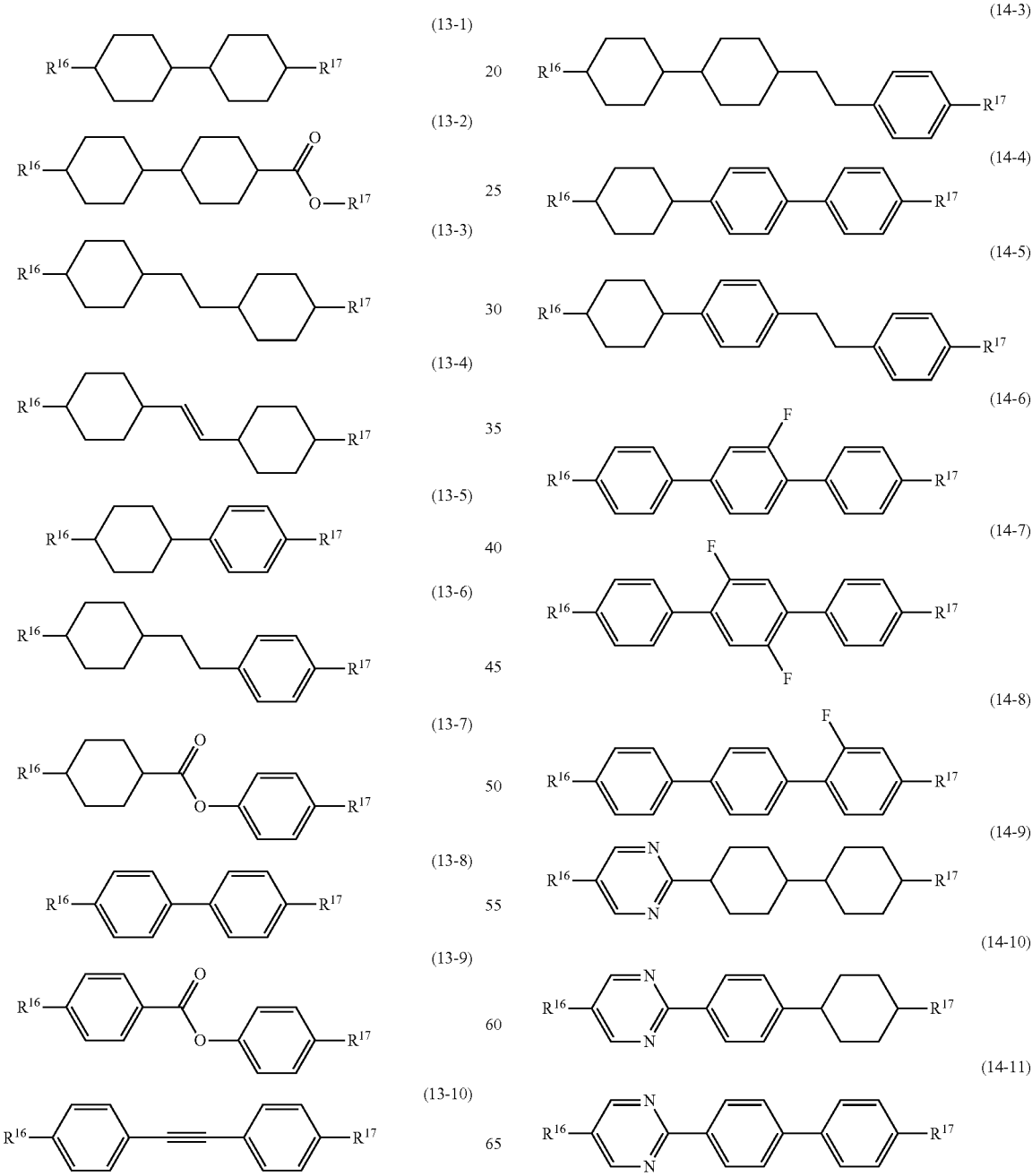

(14-12)
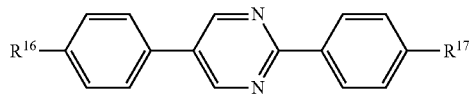

(14-13)
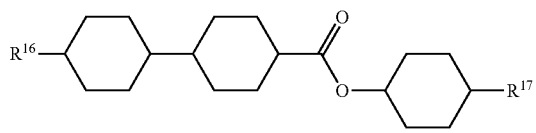

(14-14)
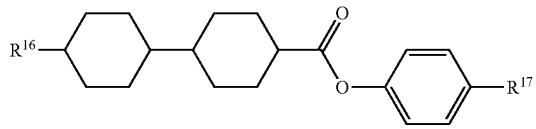

(14-15)
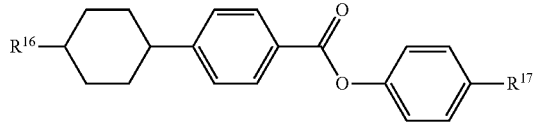

(14-16)
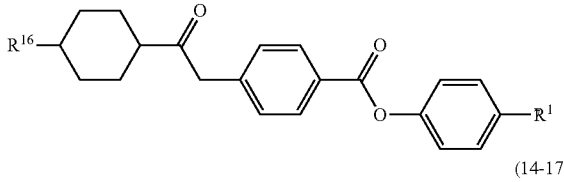

(14-17)
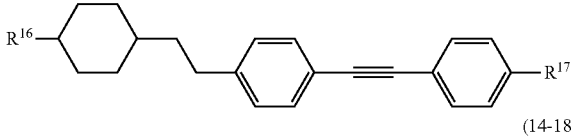

(14-18)
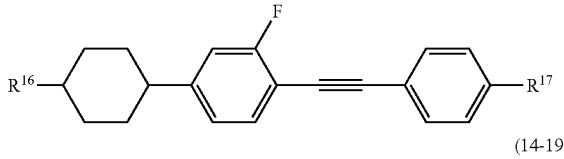

(14-19)
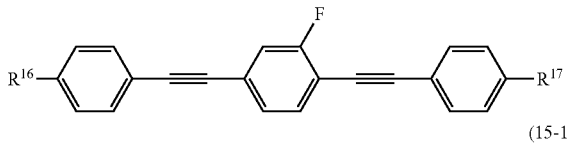

(15-1)
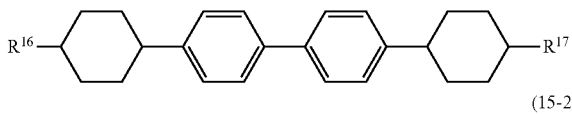

(15-2)
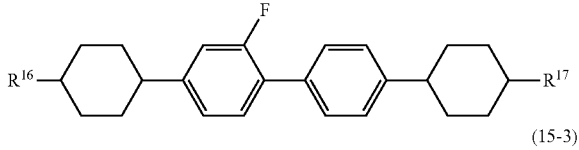

(15-3)

(15-4)
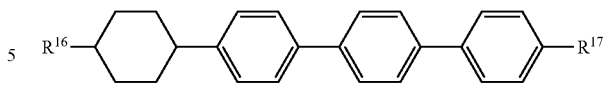

(15-5)
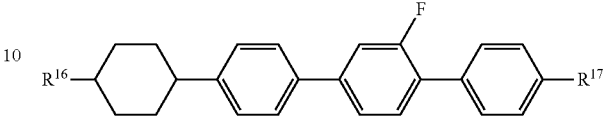

(15-6)
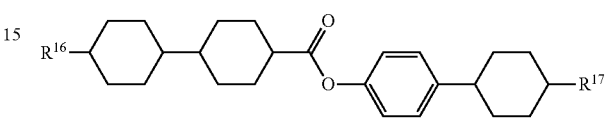

(15-7)
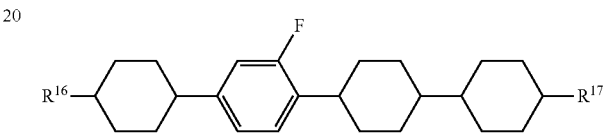

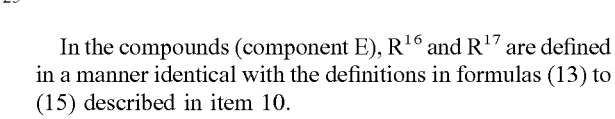

In the compounds (component E), $R^{16}$ and $R^{17}$ are defined in a manner identical with the definitions in formulas (13) to (15) described in item 10.

Component E has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or effective in adjusting the optical anisotropy.

When a content of component E is increased, the viscosity of the composition decreases, but the dielectric anisotropy also decreases. Then, the content is desirably as large as possible, as long as the composition meets a desired value of threshold voltage of the device. Therefore, when a composition for the VA mode or the PSA mode is prepared, the content of component E is preferably approximately 30% by weight or more, and further preferably, approximately 40% by weight or more, based on the total weight of the composition.

Preparation of composition (1) is performed by a method for dissolving required components at a high temperature, or the like. According to an application, an additive may be added to the composition. Examples of the additive include an optically active compound, a polymerizable compound, a polymerization initiator, an antioxidant, an ultraviolet light absorber, a light stabilizer, a heat stabilizer and a defoaming agent. Such additives are well known to those skilled in the art, and described in literature.

Composition (1) may further contain at least one optically active compound. A publicly known chiral dopant can be added as the optically active compound. The chiral dopant is effective in inducing helical structure in liquid crystal molecules to give a necessary twist angle, thereby preventing a reverse twist. Preferred examples of the chiral dopant include compounds (Op-1) to (Op-18) described below. In compound (Op-18), ring J is 1,4-cyclohexylene or 1,4-phenylene, and $R^{24}$ is alkyl having 1 to 10 carbons.

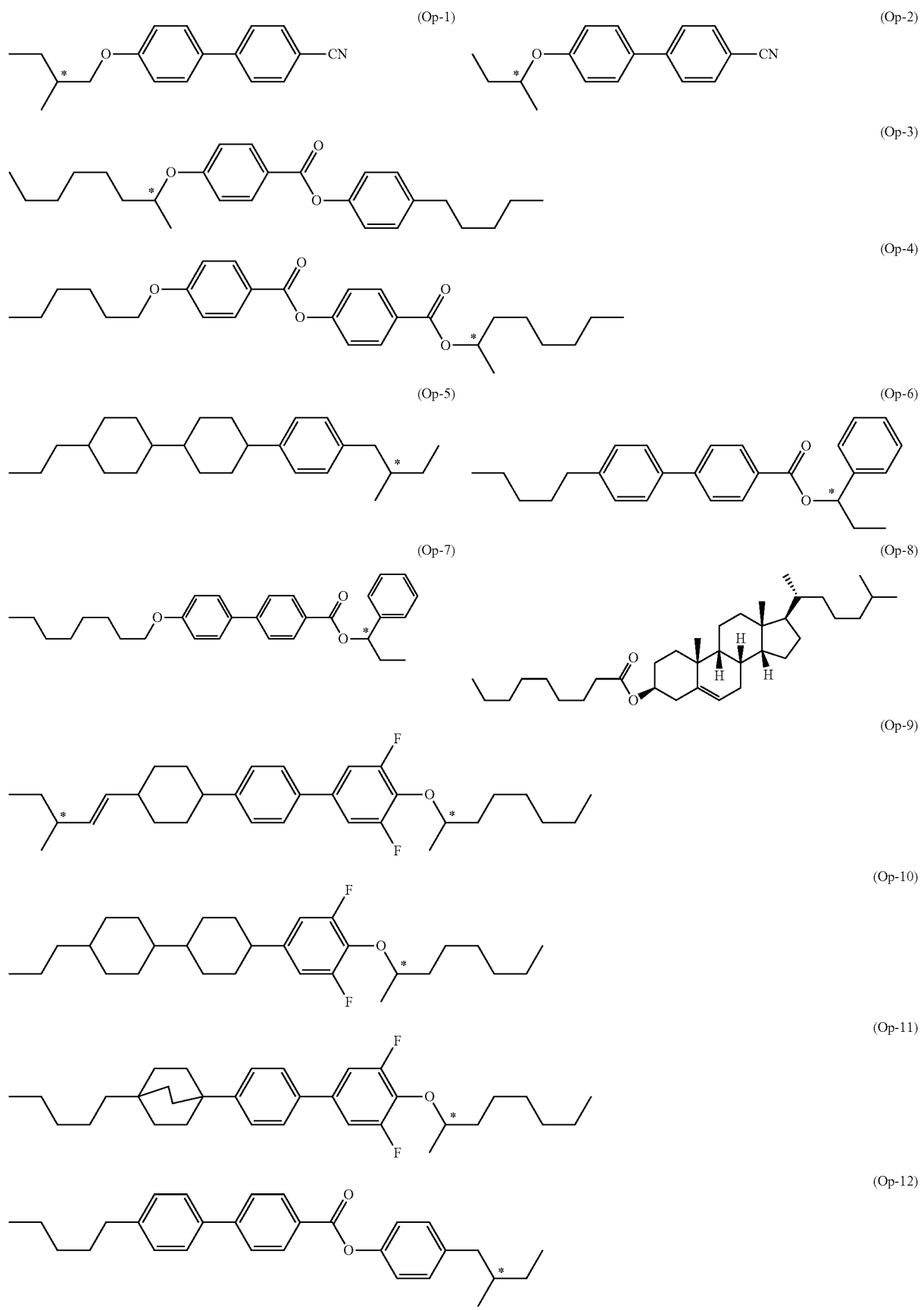

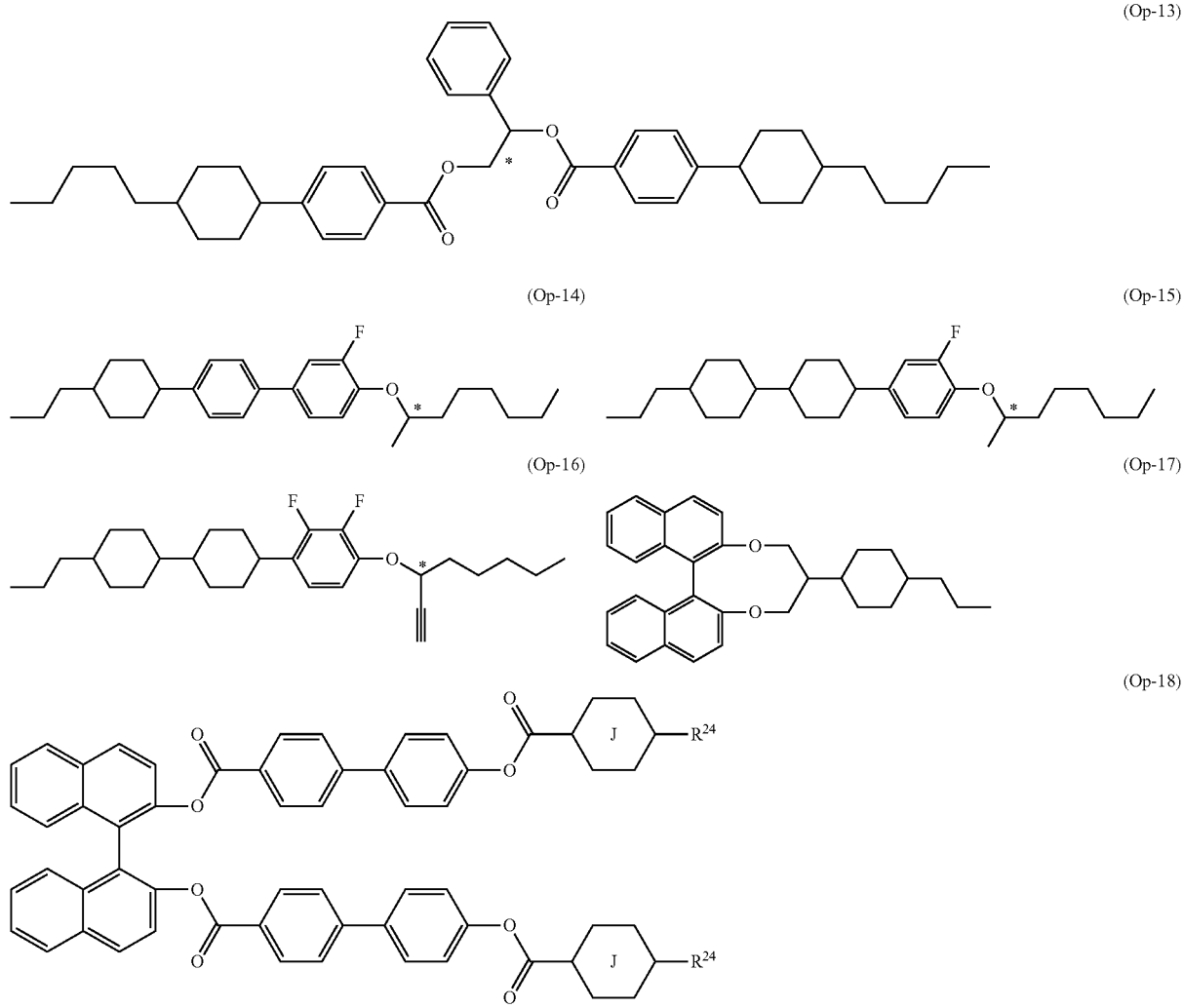

In composition (1), a helical pitch is adjusted by adding such an optically active compound. The helical pitch is preferably adjusted in the range of approximately 40 to approximately 200 micrometers in a liquid crystal composition for the TFT mode and the TN mode. In a composition for the STN mode, the helical pitch is preferably adjusted in the range of approximately 6 to approximately 20 micrometers. In the case of a composition for a BTN mode, the helical pitch is preferably adjusted in the range of approximately 1.5 to approximately 4 micrometers. For the purpose of adjusting temperature dependence of the helical pitch, two or more optically active compounds may be added.

Composition (1) can also be used for the PSA mode by adding the polymerizable compound. Examples of the polymerizable compound include acrylate, methacrylate, a vinyl compound, a vinyloxy compound, propenyl ether, an epoxy compound (oxirane, oxetane) and vinyl ketone. Preferred examples include compounds (M-1) to (M-16) described below. The polymerizable compound polymerizes by irradiation with ultraviolet light or the like. The compound may be polymerized in the presence of a suitable initiator such as a photopolymerization initiator. Suitable conditions for polymerization, suitable types of the initiator and suitable amounts thereof are known to those skilled in the art and are described in literature.

In compounds (M-1) to (M-16), $R^{25}$, $R^{26}$, $R^{27}$ and $R^{28}$ are independently hydrogen or methyl; s, v and x are independently 0 or 1; and t and u are independently an integer from 1 to 10. $L^{21}$, $L^{22}$, $L^{23}$, $L^{24}$, $L^{25}$, $L^{26}$, $L^{27}$ and $L^{28}$ are independently hydrogen or fluorine.

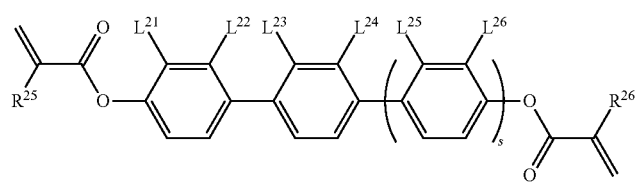

(M-2)
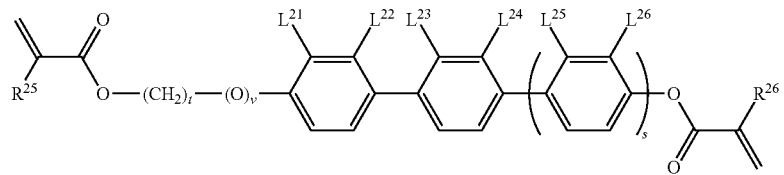
(M-3)
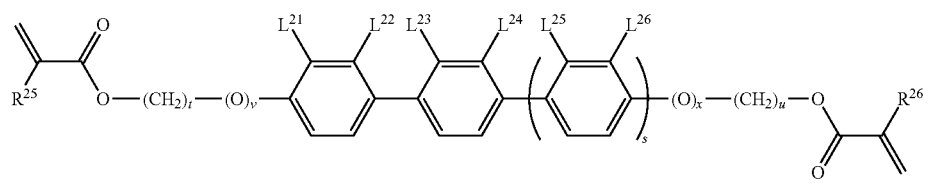
(M-4)
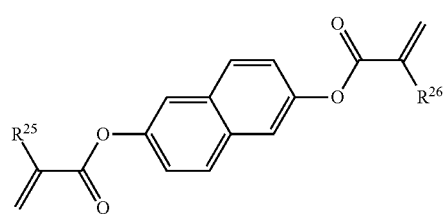
(M-5)
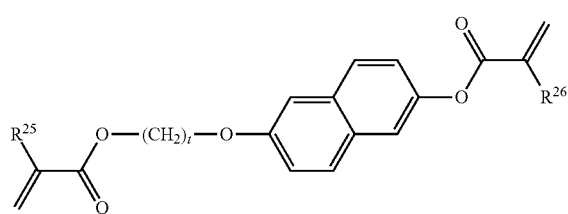
(M-6)
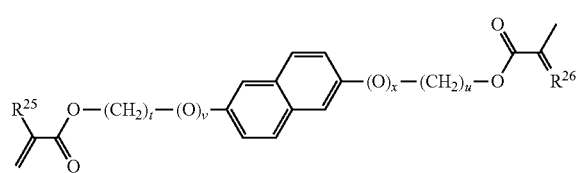
(M-7)
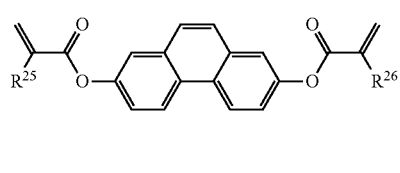
(M-8)
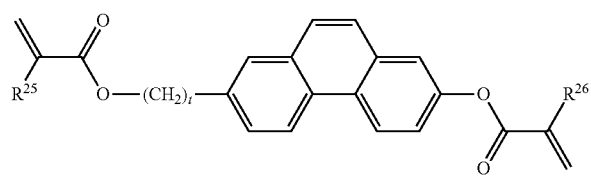
(M-9)
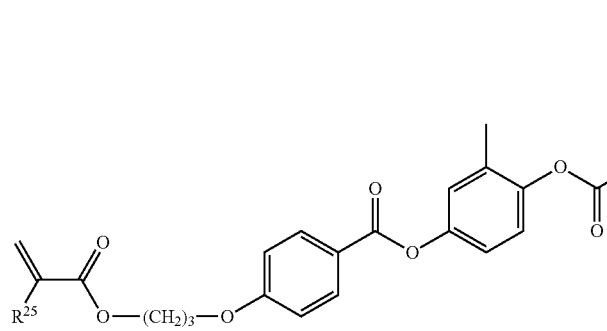
(M-10)
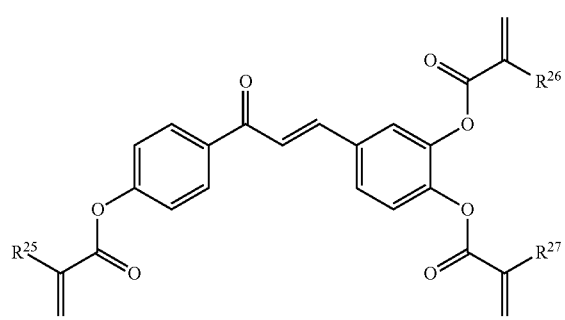

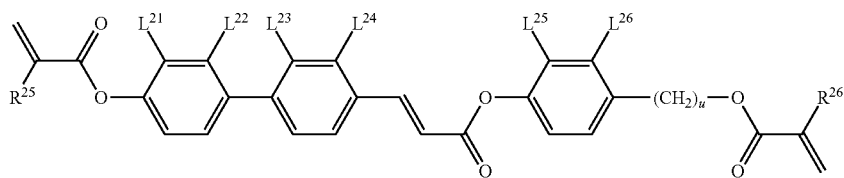
(M-11)

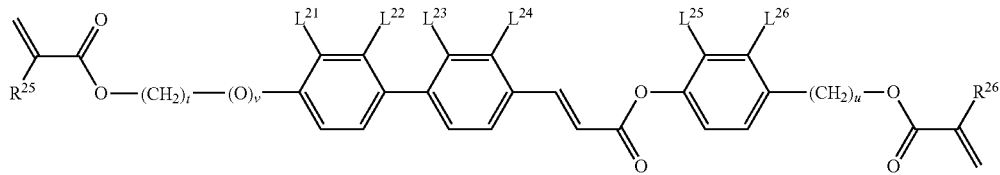
(M-12)

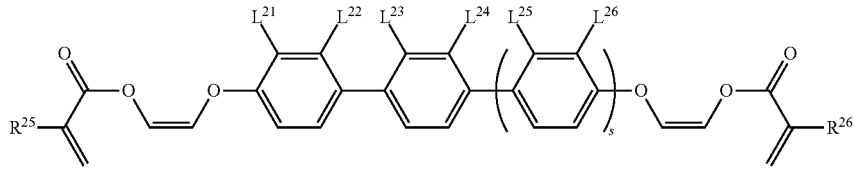
(M-13)

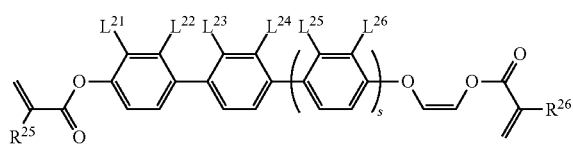
(M-14)

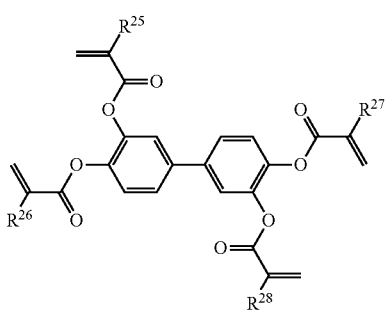
(M-15)

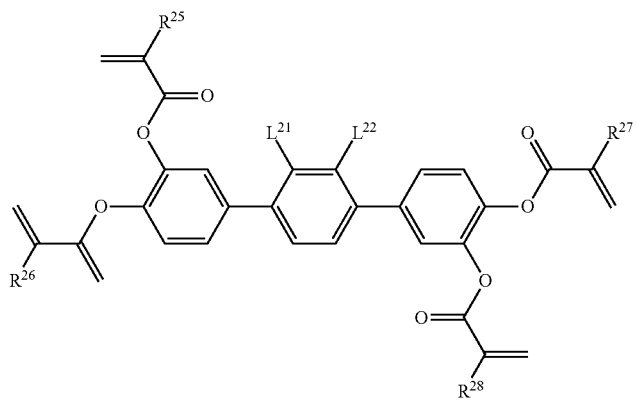
(M-16)

The antioxidant is effective for maintaining a large voltage holding ratio. Preferred examples of the antioxidant include compounds (AO-1) or (AO-2) described below; or Irganox 415, Irganox 565, Irganox 1010, Irganox 1035, Irganox 3114 or Irganox 1098 (trade names: BASF SE). The ultraviolet light absorber is effective for preventing a decrease in the maximum temperature. Preferred examples of the ultraviolet light absorber include a benzophenone derivative, a benzoate derivative and a triazole derivative. Specific examples include compounds (AO-3) or (AO-4) described below; Tinuvin 329, Tinuvin P, Tinuvin 326, Tinuvin 234, Tinuvin 213, Tinuvin 400, Tinuvin 328 or Tinuvin 99-2 (trade names: BASF SE); and 1,4-diazabicyclo [2.2.2]octane (DABCO).

A light stabilizer such as an amine having steric hindrance is preferred for maintaining the large voltage holding ratio. Preferred examples of the light stabilizer include compounds (AO-5) or (AO-6) described below; and Tinuvin 144, Tinuvin 765 or Tinuvin 770DF (trade names: BASF SE). The heat stabilizer is also effective for maintaining the large voltage holding ratio, and preferred examples include Irgafos 168 (trade name: BASF SE). The defoaming agent is effective in preventing foam formation. Preferred examples of the defoaming agent include dimethyl silicone oil and methylphenyl silicone oil.

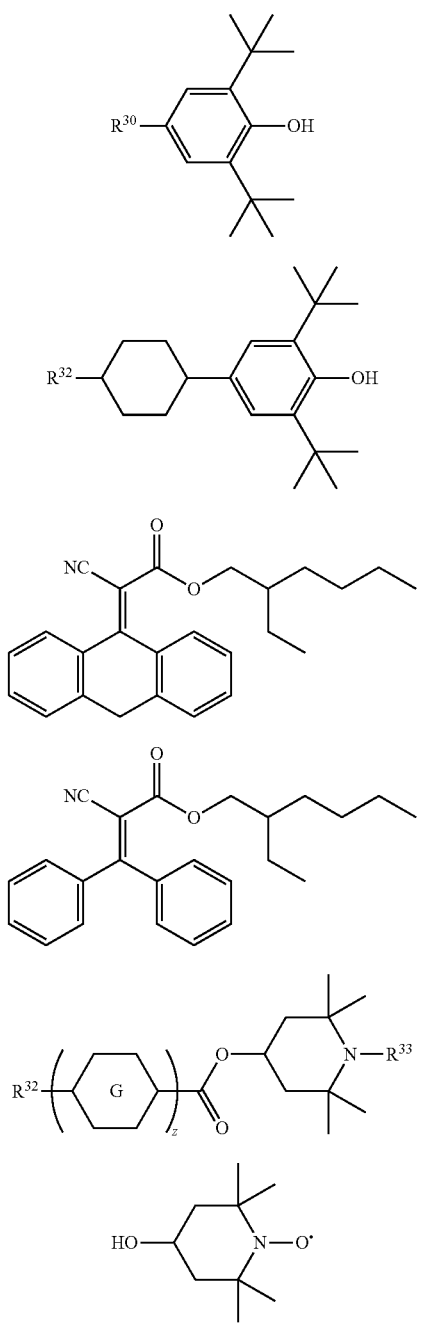

In compound (AO-1), $R^{30}$ is alkyl having 1 to 20 carbons, alkoxy having 1 to 20 carbons, —COOR$^{31}$ or —CH$_2$CH$_2$COOR$^{31}$, and $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl or O. (oxygen radical); ring G is 1,4-cyclohexylene or 1,4-phenylene; and z is 1, 2 or 3.

Composition (1) can also be used for a guest host (GH) mode by addition of a dichroic dye such as a merocyanine type, a stylyl type, an azo type, an azomethine type, an azoxy type, a quinophthalone type, an anthraquinone type and a tetrazine type.

In composition (1), the maximum temperature can be adjusted to approximately 70° C. or higher and the minimum temperature can be adjusted to approximately −10° C. or lower by appropriately adjusting a kind and a ratio of component compounds, and therefore the temperature range of the nematic phase is wide. Accordingly, a liquid crystal display device including the composition can be used in the wide temperature range.

In composition (1), the optical anisotropy can be adjusted into the range of approximately 0.10 to approximately 0.13 or into the range of approximately 0.05 to approximately 0.18 by appropriately adjusting a kind and a ratio of component compounds. In a similar manner, the dielectric anisotropy can be adjusted into the range of approximately −5.0 to approximately −2.0. Preferred dielectric anisotropy is in the range of approximately −4.5 to approximately −2.5. Composition (1) having the dielectric anisotropy in the above range can be suitably used for a liquid crystal display device that operates by the IPS mode, VA mode or PSA mode.

3. Liquid Crystal Display Device

Composition (1) can be used for an AM device. The composition can also be used for a PM device. The composition can be used for an AM device and a PM device having a mode such as PC, TN, STN, ECB, OCB, IPS, FFS, VA, PSA or FPA. Use for an AM device having the TN, OCB, IPS or FFS mode is particularly preferred. In an AM device having the IPS or FFS mode, alignment of liquid crystal molecules in a state in which no voltage is applied may be parallel or perpendicular to a panel substrate. The device may be of a reflective type, a transmissive type or a transreflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, and for a polymer dispersed (PD) device in which a three-dimensional network-polymer is formed in the composition.

Composition (1) has the negative dielectric anisotropy, and therefore can be suitably used for a liquid crystal display device that has an operating mode such as the VA mode, the IPS mode or the PSA mode and is driven by an AM mode. The composition can be particularly suitably used for a liquid crystal display device that has the VA mode and is driven by the AM mode.

In a liquid crystal display device that operates in the TN mode, the VA mode or the like, a direction of an electric field is perpendicular to a direction of a liquid crystal layer. On the other hand, in a liquid crystal display device that operates in the IPS mode or the like, the direction of the electric field is parallel to the direction of the liquid crystal layer. A structure of a liquid crystal display device that operates in the VA mode is reported by K. Ohmuro, S. Kataoka, T. Sasaki and Y. Koike, SID '97 Digest of Technical Papers, 28, 845 (1997). A structure of a liquid crystal display device that operates in the IPS mode is reported in WO 91/10936 A (family: U.S. Pat. No. 5,576,867 B).

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLE

The invention will be described in greater detail by way of Examples. However, the invention is not limited by the Examples.

NMR Analysis

As a measuring apparatus, DRX-500 (made by Bruker BioSpin Corporation) was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. Then, $^{19}$F-NMR measurement was carried out using $CFCl_3$ as an internal standard and under conditions of 24 times of accumulation. In the explanation of nuclear magnetic resonance spectra, symbols s, d, t, q, quin, sex and m stand for a singlet, a doublet, a triplet, a quartet, a quintet, a sextet, a multiplet, and br being broad, respectively.

Sample for Measurement

When phase structure and transition temperature were measured, a liquid crystal compound itself was used as a sample. When physical properties such as a maximum temperature of a nematic phase, viscosity, optical anisotropy and dielectric anisotropy were measured, a composition prepared by mixing the compound with a base liquid crystal was used as a sample.

When the sample in which the compound was mixed with the base liquid crystal was used, measurement was carried out according to a method described below. The sample was prepared by mixing 15% by weight of the compound and 85% by weight of the base liquid crystal. Then, extrapolated values were calculated from measured values of the sample according to an extrapolation method represented by an equation below, and the extrapolated values were described. {Extrapolated value}={100×(measured value of a sample)−(% by weight of base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal is changed in the order of (10% by weight:90% by weight), (5% by weight:95% by weight) and (1% by weight:99% by weight), and physical properties of the sample were measured at a ratio at which the crystals (or the smectic phase) did not precipitate at 25° C. In addition, unless otherwise noted, the ratio of the compound to the base liquid crystal was 15% by weight:85% by weight As the base liquid crystal, base liquid crystal (i) described below was used. Ratios of components of base liquid crystal (i) are expressed in terms of % by weight.

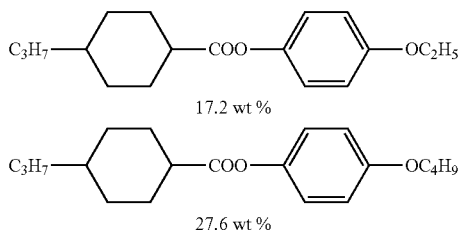

-continued

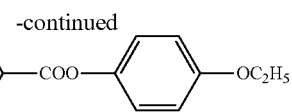

20.7 wt %

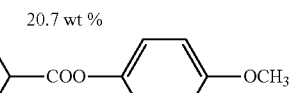

20.7 wt %

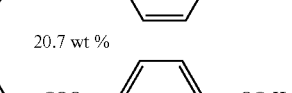

13.8 wt %

Measurement Methods

Physical properties were measured according to methods described below. Most of the methods are applied as described in the Standard of the Japan Electronics and Information Technology Industries Association (hereinafter, abbreviated as JEITA) (JEITA ED-2521A) discussed and established by JEITA, or as modified thereon. No TFT was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

A sample was heated and then cooled at a rate of 3° C. per minute using a scanning calorimeter, DSC-7 System or Diamond DSC System, made by PerkinElmer, Inc., and a starting point of an endothermic peak or an exothermic peak caused by a change of phases of the sample was determined by extrapolation, and thus a transition temperature was determined. Temperature at which a compound undergoes transition from a solid to a liquid crystal phase such as a smectic phase and a nematic phase may be occasionally abbreviated as "minimum temperature of the liquid crystal phase". Temperature at which a compound undergoes transition from the liquid crystal phase to a liquid may be occasionally abbreviated as a "clearing point."

Crystals were expressed as C. When kinds of the crystals were distinguishable, each of the crystals was expressed as $C_1$ or $C_2$. The smectic phase was expressed as S, and the nematic phase was expressed as N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. The transition temperature was expressed as "C 50.0 N 100.0 I," for example. The expression indicates that the transition temperature from the crystal to the nematic phase is 50.0° C., and the transition temperature from the nematic phase to the liquid is 100.0° C.

(3) Compatibility at a Low Temperature

Samples in which the base liquid crystal and the compound were mixed for the compound to be 20% by weight, 15% by weight, 10% by weight, 5% by weight, 3% by weight and 1% by weight were prepared, and placed in glass vials. After the glass vials were kept in freezers at −10° C. or −20° C. for a predetermined period of time, whether or not crystals (or a smectic phase) precipitated was observed.

(4) Maximum Temperature of a Nematic Phase ($T_{NI}$ or NI; ° C.)

A sample was placed on a hot plate in a melting point apparatus equipped with a polarizing microscope and was heated at the rate of 1° C. per minute. Temperature was measured when part of the sample began to change from a nematic phase to an isotropic liquid. When the sample was a mixture of a compound and the mother liquid crystal, the maximum temperature was expressed using a symbol $T_{NI}$. When the sample was a mixture of a compound and component B, the maximum temperature was expressed using a symbol NI.

(5) Minimum Temperature of a Nematic Phase ($T_C$; ° C.)

Samples each having a nematic phase were kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_c$ was expressed as $T_c \leq -20°$ C.

(6) Viscosity (Bulk Viscosity; η; measured at 20° C.; mPa·s)

A cone-plate (E type) rotational viscometer was used for measurement (7) Viscosity (Rotational Viscosity; γ1; measured at 25° C.; mPa·s)

Measurement was carried out according to a method described in M. Imai et al., Molecular Crystals and Liquid Crystals, Vol. 259, 37 (1995). A sample was put in a VA device in which a distance (cell gap) between two glass substrates was 20 micrometers. Voltage was applied stepwise to the device in the range of 30 V to 50 V at an increment of 1 V. After a period of 0.2 second with no voltage application, voltage was applied repeatedly under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. As a value of dielectric anisotropy necessary for the calculation, a value measured in the section of dielectric anisotropy described below was used (8) Optical Anisotropy (Refractive Index Anisotropy; Measured at 25° C.; Δn)

Measurement was carried out by an Abbe refractometer with a polarizing plate mounted on an ocular by using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥−n⊥.

(9) Dielectric Anisotropy (Δ∈; Measured at 25° C.)

A value of dielectric anisotropy was calculated from an equation: Δ∈=∈∥−∈⊥. A dielectric constant (∈∥ and ∈⊥) was measured as described below.

(1) Measurement of dielectric constant (∈∥): An ethanol (20 mL) solution of octadecyltriethoxysilane (0.16 mL) was applied to well-cleaned glass substrates. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(10) Elastic Constant ($K_{11}$ and $K_{33}$; Measured at 25° C.; pN)

For measurement, Elastic Constant Measurement System Model EC-1 made by TOYO Corporation was used. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) applied to the device was increased stepwise from 0 V to 20 V at an increment of 0.02 V. On the occasion, the device was irradiated with light from a perpendicular direction, and an amount of light transmitted through the device was measured. A voltage-transmittance curve was prepared, in which the maximum value of the amount of light corresponded to 100% transmittance and the minimum value of the amount of light corresponded to 0% transmittance. A threshold voltage is voltage at 10% transmittance.

(12) Voltage Holding Ratio (VHR-1; Measured at 25° C.; %)

A TN device used for measurement had a polyimide alignment film and a distance (cell gap) between two glass substrates was 5 micrometers. A sample was put in the device, and then the device was sealed with an ultraviolet-curable adhesive. The TN device was charged by applying a pulse voltage (60 microseconds at 5 V). A decaying voltage was measured for 16.7 milliseconds with a high-speed voltmeter, and area A between a voltage curve and a horizontal axis in a unit cycle was obtained. Area B was an area without decay. A voltage holding ratio was a percentage of area A to area B.

(13) Voltage Holding Ratio (VHR-2; Measured at 80° C.; %)

A TN device used for measurement had a polyimide alignment film and a distance (cell gap) between two glass substrates was 5 micrometers. A sample was put in the device, and then the device was sealed with an ultraviolet-curable adhesive. The TN device was charged by applying a pulse voltage (60 microseconds at 5 V). A decaying voltage was measured for 16.7 milliseconds with a high-speed voltmeter, and area A between a voltage curve and a horizontal axis in a unit cycle was obtained. Area B was an area without decay. A voltage holding ratio was a percentage of area A to area B.

1-1. Example of Compound (1)

Compound (1) was prepared according to procedures described below. The prepared compound was identified by a method such as an NMR analysis. Physical properties of the compound were measured by methods described above.

Example 1

Synthesis of Compound (1-1-2)

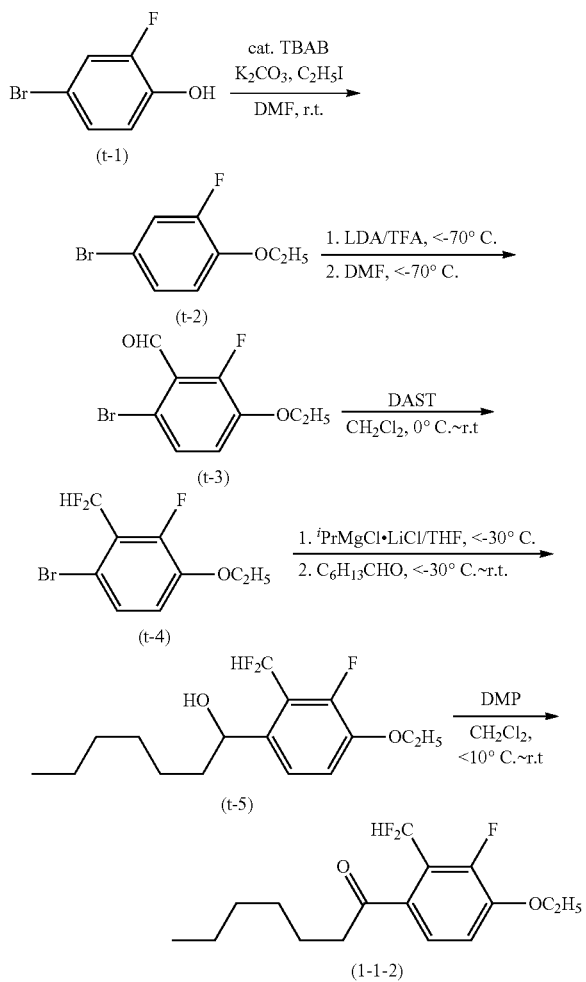

First Step

In a reaction vessel, 4-bromo-2-fluorophenol (t-1) (48 g, 252 mmol), potassium carbonate (69.6 g, 504 mmol), tetrabutylammonium bromide (TBAB; 4.07 g, 12.6 mmol) and N,N-dimethylformamide (DMF; 400 mL) were put. Ethyl iodide (78.6 g, 504 mmol) was slowly added dropwise thereto at room temperature, and then the resulting mixture was stirred at room temperature for 5 hours. The resulting reaction mixture was poured into saturated brine, and subjected to extraction with hexane. Organic layers combined were washed with water and saturated brine, and dried over anhydrous sodium sulfate. The resulting solution was concentrated under reduced pressure, and the residue was purified by distillation under reduced pressure to give compound (t-2) (49.6 g, 226 mmol; 89.7%).

Second Step

Under a nitrogen atmosphere, compound (t-2) (40 g, 182.6 mmol) obtained in the first step and THF (600 mL) were put in a reaction vessel, and then cooled to −70° C. or lower. Next, a THF solution (1.09 M, 167.5 mL, 182.6 mmol) of lithium diisopropylamide (LDA) was added dropwise thereto at −70° C. or lower. The resulting mixture was stirred at −70° C. or lower for 1 hour, and then a THF (30 mL) solution of N,N-dimethylformamide (DMF; 14.7 g, 200.8 mmol) was added dropwise thereto at −70° C. or lower. The resulting mixture was stirred at −70° C. or lower for 2 hours, and then the resulting reaction mixture was poured into an ice-added aqueous solution of ammonium chloride, and stirred for 15 minutes. The resulting reaction liquid was separated into an organic layer and an aqueous layer, and the aqueous layer was subjected to extraction with ethyl acetate. Organic layers combined were washed with water and saturated brine, and dried over anhydrous sodium sulfate. The resulting solution was concentrated under reduced pressure, and the residue was purified by column chromatography (filler: silica gel, eluate: hexane/ethyl acetate=4/1), and then recrystallized from heptane to give compound (t-3) (30.5 g, 123.4 mmol; 67.6%).

Third Step

Under a nitrogen atmosphere, compound (t-3) (30.0 g, 121.4 mmol) obtained in the second step and dichloromethane (300 mL) were put in a reaction vessel, and then cooled with ice. Next, diethylaminosulfur trifluoride (DAST; 41.1 g, 255 mmol) was added dropwise thereto, and then the resulting mixture was stirred at room temperature for 12 hours. The resulting reaction mixture was poured into ice-added saturated sodium bicarbonate water, and stirred for 30 minutes. The resulting reaction liquid was separated into an organic layer and an aqueous layer, and then the aqueous layer was subjected to extraction with ethyl acetate. Organic layers combined were washed with water and saturated brine, and dried over anhydrous sodium sulfate. The resulting solution was concentrated under reduced pressure, and the residue was purified by column chromatography (filler: silica gel, eluate: hexane/ethyl acetate=9/1) to give compound (t-4) (29.2 g, 108.5 mmol; 89.4%).

Fourth Step

Under a nitrogen atmosphere, compound (t-4) (3.65 g, 13.56 mmol) obtained in the third step and THF (55 mL) were put in a reaction vessel, and then cooled to −30° C. or lower. Next, a THF solution (1.3 M, 10.4 mL, 13.52 mmol) of isopropylmagnesium bromide and lithium chloride was added dropwise thereto at −30° C. or lower, and then the resulting mixture was stirred at room temperature for 1 hour. The resulting reaction liquid was again cooled to −30° C. or lower, and then a THF (10 mL) solution of 1-heptanal (1.86 g, 16.27 mmol) was added dropwise thereto. The resulting reaction mixture was stirred at room temperature for 2 hours, and then the resulting reaction mixture was poured into a saturated aqueous solution of ammonium chloride, and subjected to extraction with ethyl acetate. An organic layer extracted was washed with water and saturated brine, and dried over anhydrous sodium sulfate. The resulting solution was concentrated under reduced pressure, and the residue was purified by column chromatography (filler: silica gel, eluate: hexane/ethyl acetate=4/1) to give compound (t-5) (3.92 g, 12.88 mmol; 95%).

Fifth Step

Under a nitrogen atmosphere, compound (t-5) (3.92 g, 12.88 mmol) obtained in the fourth step and dichloromethane (60 mL) were put in a reaction vessel, and then cooled with ice, and Dess-Martin periodinane (DMP; 8.19 g, 19.32 mmol) was added thereto divisionally 3 times. The resulting mixture was further stirred for 2 hours while being returned to room temperature. The resulting reaction mixture was poured into saturated sodium bicarbonate water, and subjected to extraction with ethyl acetate. Organic layers combined were washed with water, a sodium sulfite aqueous solution, water and saturated brine in the order, and dried over anhydrous sodium sulfate. The resulting solution was concentrated under reduced pressure, and the residue was purified by silica gel chromatography (volume ratio, heptane:ethyl acetate=9:1), and then recrystallized (heptane/ethanol) to give object compound (1-1-2) (2.31 g, 7.64 mmol; 59.3%).

$^1$H-NMR (CDCl$_3$) δ 7.43 (d, 1H), 7.38 (t, 1H; CF$_2$H, J=53.4), 7.04 (t, 1H), 4.17 (q, 2H), 2.73 (t, 2H), 1.52 (t, 3H), 1.27-1.11 (m, 4H), 0.99-0.91 (m, 4H), 0.87 (t, 3H).

Physical properties of compound (1-1-2) were as described below.

Phase transition temperature: C 47.1 I.

Maximum temperature (NI)=−154.1° C.; dielectric anisotropy (Δ∈)=−8.03; optical anisotropy (Δn)=−0.0597.

Example 2

Synthesis of Compound (1-2-1)

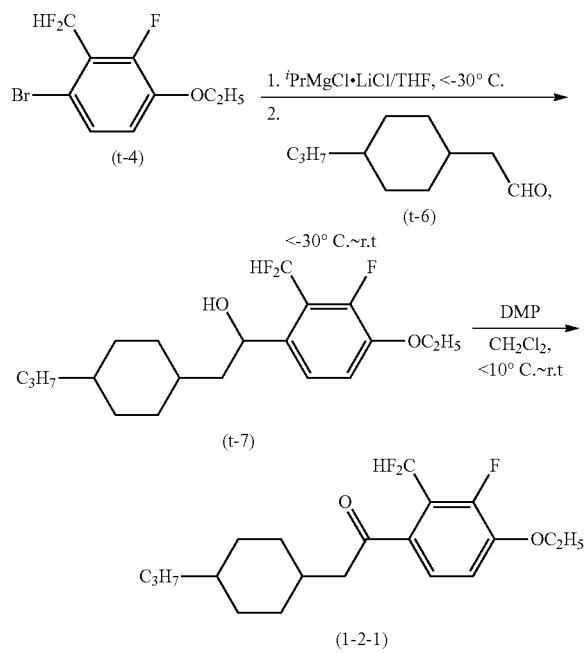

First Step

Compound (t-7) (g, mmol; %) was obtained by performing operations in a manner similar to the operations in the fourth step in Example 1, using compound (t-4) (g, mmol) obtained in the third step in Example 1, THF (55 mL), a THF solution (1.3 M, mL, mmol) of isopropylmagnesium bromide and lithium chloride, and aldehyde (t-6) (g, mmol).

Second Step

Object compound (1-2-1) (g, mmol; %) was obtained by performing operations in a manner similar to the operations in the fifth step in Example 1, using compound (t-7) (g, mmol) obtained in the first step, dichloromethane (60 mL) and Dess-Martin periodinane (DMP; g, mmol).

$^1$H-NMR (CDCl$_3$) δ 7.42 (d, 1H), 7.25 (t, 1H; CF$_2$H, J=53.3), 7.04 (t, 1H), 4.17 (q, 2H), 2.75 (d, 2H), 1.91-1.72 (m, 5H), 1.51 (t, 3H), 1.37-1.12 (m, 4H), 1.02-0.91 (m, 4H), 0.86 (t, 3H).

Physical properties of compound (1-2-1) were as described below.

Phase transition temperature: C 61.0 I.

Maximum temperature (NI)=−73.4° C.; dielectric anisotropy (Δ∈)=−12.43; optical anisotropy (Δn)=0.0243.

Example 3

Synthesis of Compound (1-4-1)

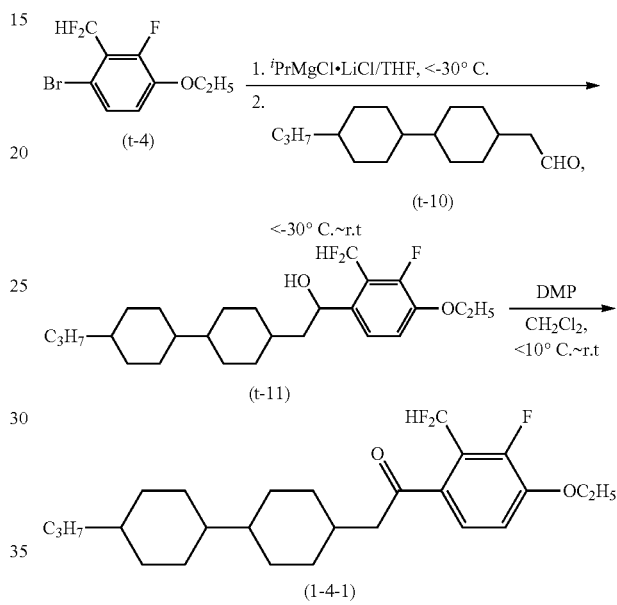

First Step

Compound (t-11) (2.12 g, 4.52 mmol; 33.1%) was obtained by performing operations in a manner similar to the operations in the fourth step in Example 1, using compound (t-4) (4.78 g, 17.74 mmol) obtained in the third step of Example 1, THF (80 mL), a THF solution (1.3 M, 13.64 mL, 17.74 mmol) of isopropylmagnesium bromide and lithium chloride, and aldehyde (t-10) (3.8 g, 13.64 mmol).

Second Step

Object compound (1-4-1) (0.74 g, 1.59 mmol; 70.1%) was obtained by performing operations in a manner similar to the operations in the fifth step in Example 1, using compound (t-11) (1.06 g, 2.26 mmol) obtained in the first step, dichloromethane (15 mL) and Dess-Martin periodinane (DMP; 1.44 g, 3.39 mmol).

$^1$H-NMR (CDCl$_3$) δ 7.43 (d, 1H), 7.39 (t, 1H; CF$_2$H, J=53.3), 7.04 (t, 1H), 4.16 (q, 2H), 2.86 (t, 2H), 1.76-1.66 (m, 6H), 1.51 (t, 3H), 1.28-1.11 (m, 8H), 1.01-0.82 (m, 13H).

Physical properties of compound (1-4-1) were as described below.

Phase transition temperature: C 102.3 I.

Maximum temperature (NI)=52.6° C.; dielectric anisotropy (Δ∈)=−13.26; optical anisotropy (Δn)=0.079.

Example 4

Synthesis of Compound (1-4-20)

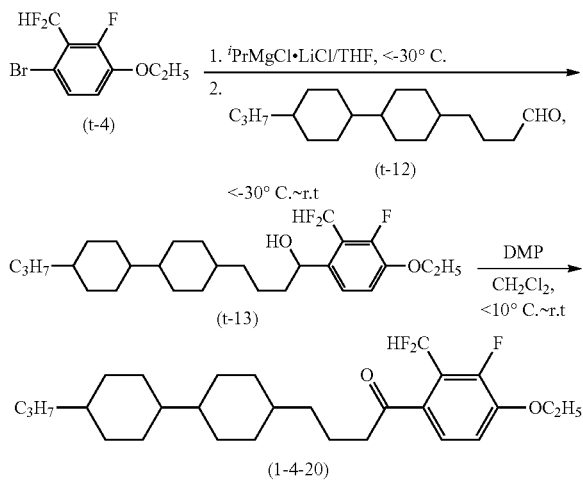

First Step

Compound (t-13) (1.06 g, 2.26 mmol; 33.1%) was obtained by performing operations in a manner similar to the operations in the fourth step in Example 1, using compound (t-4) (2.39 g, 8.87 mmol) obtained in the third step in Example 1, THF (55 mL), a THF solution (1.3 M, 6.82 mL, 8.87 mmol) of isopropylmagnesium bromide and lithium chloride, and aldehyde (t-12) (1.9 g, 6.82 mmol).

Second Step

Object compound (1-4-20) (0.74 g, 1.59 mmol; 70.1%) was obtained by performing operations in a manner similar to the operations in the fifth step in Example 1, using compound (t-13) (1.06 g, 2.26 mmol) obtained in the first step, dichloromethane (15 mL) and Dess-Martin periodinane (DMP; 1.44 g, 3.39 mmol).

$^1$H-NMR (CDCl$_3$) δ 7.43 (d, 1H), 7.38 (t, 1H; CF$_2$H, J=53.5), 7.04 (t, 1H), 4.17 (q, 2H), 2.86 (t, 2H), 1.76-1.66 (m, 10H), 1.51 (t, 3H), 1.30-1.11 (m, 8H), 1.00-0.81 (m, 13H).

Physical properties of compound (1-4-20) were as described below.

Phase transition temperature: C 121.5 I.

Maximum temperature (NI)=84.6° C.; dielectric anisotropy (Δ∈)=−11.23; optical anisotropy (Δn)=0.107.

Example 5

Synthesis of Compound (1-6-2)

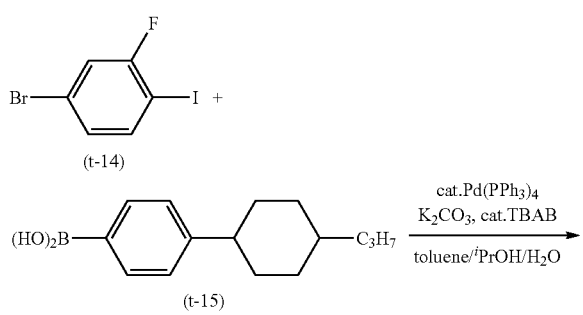

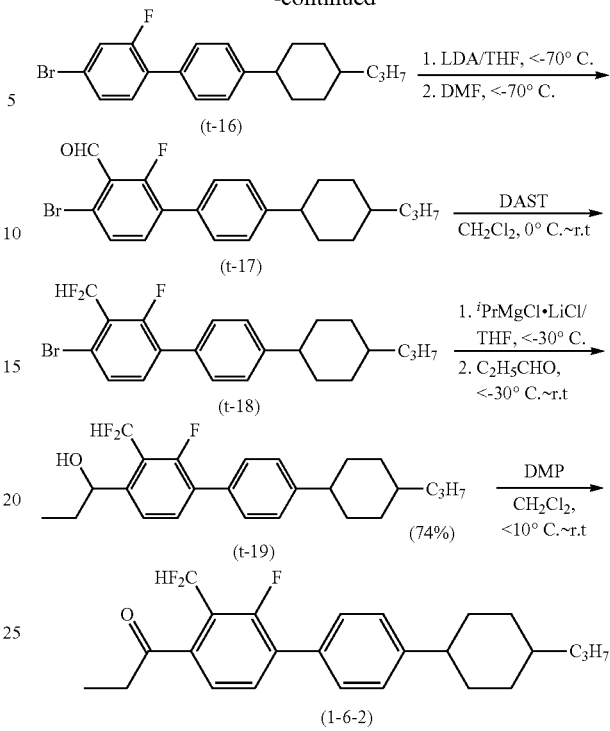

First Step

Under a nitrogen atmosphere, 3-fluoro-4-iodobromobenzene (t-14) (10.17 g, 33.85 mmol), compound (t-15) (10 g, 40.63 mmol) prepared by a publicly known method, potassium carbonate (9.36 g, 67.71 mmol), tetrabutylammonium bromide (TBAB; 2.18 g, 6.77 mmol), toluene (50 mL), isopropanol (50 mL) and water (50 mL) were put in a reaction vessel. Next, tetrakis(triphenylphosphine)palladium (0.39 g, 0.34 mmol) was added thereto at room temperature, and then the resulting mixture was heated and refluxed for 10 hours. The resulting reaction mixture cooled to room temperature was poured into water, and subjected to extraction with toluene. Organic layers combined were washed with water and saturated brine in the order, and dried over anhydrous sodium sulfate. The resulting solution was concentrated under reduced pressure, and the residue was purified by silica gel chromatography (volume ratio, heptane:ethyl acetate=9:1), and then recrystallized (heptane/ethanol) to give object compound (t-16) (11.1 g, 29.57 mmol; 87.4%).

Second Step

Compound (t-17) (9.4 g, 23.31 mmol; 78.8%) was obtained by performing operations in a manner similar to the operations in the second step in Example 1, using compound (t-16) (11.1 g, 29.57 mmol) obtained in the first step, THF (240 mL), a THF solution (1.09 M, 27.13 mL, 29.57 mmol) of lithium diisopropylamide (LDA), and N,N-dimethylformamide (DMF; 2.38 g, 32.53 mmol).

Third Step

Compound (t-18) (9.9 g, 23.3 mmol; 99%) was obtained by performing operations in a manner similar to the operation in the third step in Example 1, using compound (t-17) (9.4 g, 23.31 mmol) obtained in the second step, dichloromethane (100 mL) and diethylaminosulfur trifluoride (DAST; 7.89 g, 48.94 mmol).

Fourth Step

Compound (t-19) (6 g, 14.83 mmol; 73.6%) was obtained by performing operations in a manner similar to the operations in the fourth step in Example 1, using compound (t-18) (8.57 g, 20.15 mmol) obtained in the third step, THF (140 mL), a THF solution of isopropylmagnesium bromide and lithium chloride (1.3 M, 18.6 mL, 24.18 mmol), and 1-propanal (1.64 g, 28.21 mmol).

Fifth Step

Object compound (1-6-2) (3.3 g, 8.2 mmol; 94.8%) was obtained by performing operations in a manner similar to the operations in the fifth step in Example 1, using compound (t-19) (3.5 g, 8.65 mmol) obtained in the fourth step, dichloromethane (50 mL) and Dess-Martin periodinane (DMP; 5.5 g, 12.982 mmol).

$^1$H-NMR (CDCl$_3$) δ 7.60 (t, 1H), 7.48 (dd, 2H), 7.39 (d, 1H), 7.32 (d, 2H), 7.16 (t, 1H; CF$_2$H, J=53.5), 2.97 (q, 2H), 2.53 (tt, 1H), 1.90 (t, 4H), 1.52 (q, 2H), 1.41-1.23 (m, 8H), 1.14-1.05 (m, 2H), 0.91 (t, 3H).

Physical properties of compound (1-6-2) were as described below.

Phase transition temperature: C 67.1 I.

Maximum temperature (NI)=71.9° C.; dielectric anisotropy (Δ∈)=−6.52; optical anisotropy (Δn)=0.1377.

Example 6

Synthesis of Compound (1-4-29)

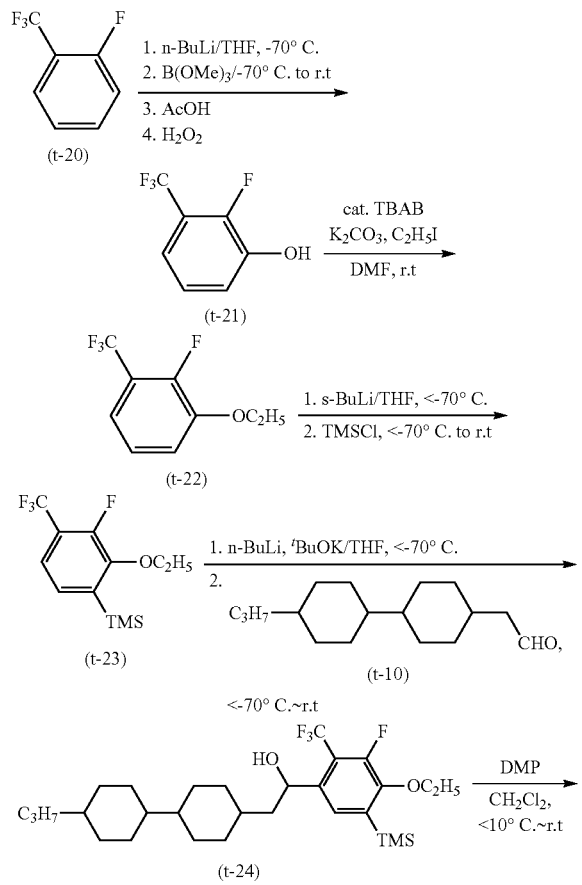

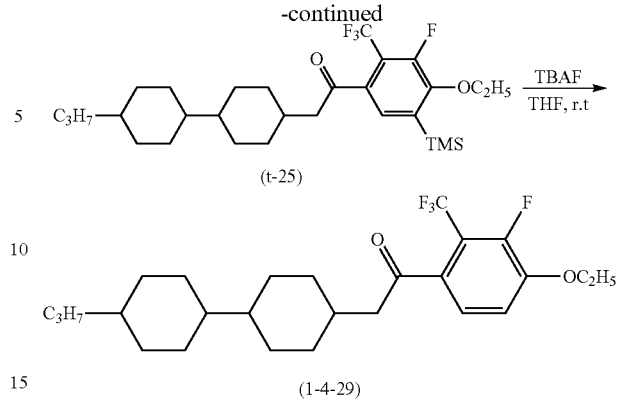

First Step

Under a nitrogen atmosphere, compound (t-20) (24.5 g, 149.30 mmol) and THF (300 mL) were put in a reaction vessel, and cooled to −70° C. or lower. Then, n-butyllithium (1.60 M; n-hexane solution; 111.97 mL, 179.16 mmol) was added dropwise thereto in the temperature range of −75° C. to −70° C., and the resulting mixture was further stirred for 1 hour. A THF (50 mL) solution of trimethyl borate (18.62 g, 179.16 mmol) was added dropwise thereto in the temperature range of −75° C. to −70° C., and the resulting mixture was stirred for 3 hours while being returned to room temperature. Acetic acid (12.82 mL, 223.95 mmol) was added dropwise thereto in the temperature range of 20° C. to 25° C. After 30 minutes, hydrogen peroxide (30% aqueous solution, 33.86 g, 298.60 mmol) was added dropwise thereto in the temperature range of 25° C. to 35° C., and the resulting mixture was further stirred for 10 hours. The resulting reaction mixture was poured into water, and subjected to extraction with ethyl acetate. Organic layers combined were washed with water, a sodium sulfite aqueous solution, water and saturated brine in the order, and dried over anhydrous sodium sulfate. The resulting solution was concentrated under reduced pressure to give compound (t-21) (26.89 g, 149.30 mol; 99%). Compound (t-21) was used for a next reaction without purification.

Second Step

Compound (t-22) (21.1 g, 101.37 mmol; 67.9%) was obtained by performing operations in a manner similar to the operation in the second step in Example 1, using compound (t-21) (26.89 g, 149.30 mmol) obtained in the first step, potassium carbonate (41.27 g, 298.6 mmol), tetrabutylammonium bromide (TBAB; 2.41 g, 7.47 mmol), N,N-dimethylformamide (DMF; 250 mL) and ethyl iodide (46.57 g, 298.61 mmol).

Third Step

Under a nitrogen atmosphere, compound (t-22) (16.73 g, 80.37 mmol) obtained in the second step and THF (170 mL) were put in a reaction vessel, and cooled to −70° C. or lower. Then, sec-butyllithium (1.00 M; n-hexane solution; 96.0 mL, 96.0 mmol) was added dropwise thereto in the temperature range of −75° C. to −70° C., and the resulting mixture was stirred for 1 hour. A THF (20 mL) solution of trimethylsilyl chloride (10.72 mL, 98.67 mmol) was added dropwise thereto in the temperature range of −75° C. to −70° C., and the resulting mixture was stirred for 4 hours while being returned to room temperature. The resulting reaction mixture was poured into water, and subjected to extraction with ethyl acetate. Organic layers combined were washed with water and saturated brine in the order, and dried over anhydrous sodium sulfate. The resulting solution was concentrated under reduced pressure, and the residue was purified by silica gel chromatography (heptane) to give compound (t-23) (21.14 g, 75.41 mmol; 93.8%).
Fourth Step Under a nitrogen atmosphere, compound (t-23) (5.0 g, 15.61 mmol) obtained in the third step, potassium-tert-butoxide (1.94 g, 17.29 mmol) and THF (30 mL) were put in a reaction vessel, and cooled to −70° C. or lower. Then, n-butyllithium (1.60 M; n-hexane solution; 10.7 mL, 17.12 mmol) was added dropwise thereto in the temperature range of −75° C. to −70° C., and the resulting mixture was further stirred for 2 hours. A THF (20 mL) solution of compound (t-10) (8.60 g, 17.17 mmol) was added dropwise thereto in the temperature range of −75° C. to −70° C., and the resulting mixture was stirred for 4 hours while being returned to room temperature. Organic layers combined were washed with water and saturated brine in the order, and dried over anhydrous sodium sulfate. The resulting solution was concentrated under reduced pressure, and the residue was purified by silica gel chromatography (volume ratio, heptane:ethyl acetate=9:1) to give compound (t-24) (2.73 g, 5.14 mmol; 32.9%).
Fifth Step Compound (t-25) (0.84 g, 1.59 mmol; 56.2%) was obtained by performing operations in a manner similar to the operations in the fifth step in Example 1, using compound (t-24) (2.73 g, 5.14 mmol) obtained in the fourth step, dichloromethane (50 mL) and Dess-Martin periodinane (DMP; 3.27 g, 7.71 mmol).
Sixth Step Under a nitrogen atmosphere, compound (t-25) (0.84 g, 1.59 mmol) obtained in the fifth step and THF (15 mL) were put in a reaction vessel, and then tetrabutylammonium fluoride (TBAF, 1.0 M; THF solution; 1.7 mL, 1.7 mmol) was added dropwise thereto, and then the resulting mixture was stirred for 2 hours. The resulting reaction mixture was poured into water, and subjected to extraction with ethyl acetate. Organic layers combined were washed with water and saturated brine in the order, and dried over anhydrous sodium sulfate. The resulting solution was concentrated under reduced pressure, and the residue was purified by silica gel chromatography (toluene), and then recrystallized (heptane/ethanol) to give object compound (1-4-29) (0.46 g, 1.01 mmol; 63.4%).

$^1$H-NMR (CDCl$_3$) δ 7.10 (t, 1H), 7.01 (d, 1H), 4.14 (q, 2H), 2.63 (d, 2H), 1.86-1.79 (d, 3H), 1.71 (q, 6H), 1.48 (t, 3H), 1.33-1.26 (m, 2H), 1.13-0.90 (m, 13H), 0.86 (t, 3H).

Physical properties of compound (1-4-29) were as described below.

Phase transition temperature: C 90.0 N 92.0 I.

Maximum temperature (NI)=85.3° C.; dielectric anisotropy (Δ∈)=−8.8; optical anisotropy (Δn)=0.087.

Example 7

Synthesis of Compound (1-6-9)

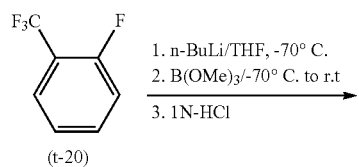

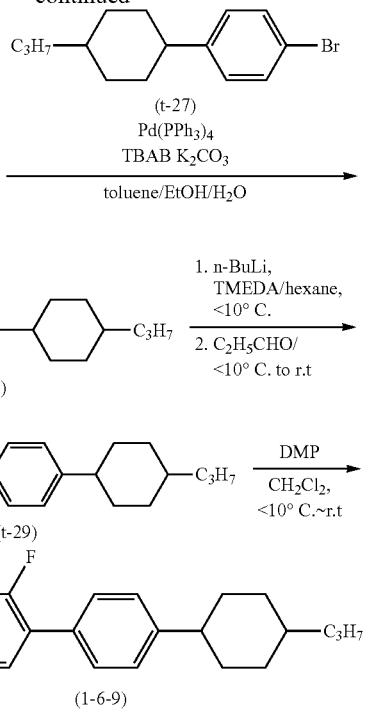

First Step

Under a nitrogen atmosphere, compound (t-20) (25 g, 152.35 mmol) and THF (300 mL) were put in a reaction vessel, and cooled to −70° C. or lower. Then, n-butyllithium (1.60 M; n-hexane solution; 105 mL, 168 mmol) was added dropwise thereto in the temperature range of −75° C. to −70° C., and the resulting mixture was further stirred for 1 hour. A THF (50 mL) solution of trimethyl borate (19.06 g, 183.47 mmol) was added dropwise thereto in the temperature range of −75° C. to −70° C., and the resulting mixture was stirred for 3 hours while being returned to room temperature. The resulting reaction mixture was poured into 1N-hydrochloric acid (300 mL), and further stirred for 1 hour, and then subjected to extraction with ethyl acetate. Organic layers combined were washed with water and saturated brine in the order, and dried over anhydrous sodium sulfate. The resulting solution was concentrated under reduced pressure, and then the residue was washed with heptane to give compound (t-26) (27.82 g, 133.8 mmol; 9987.8%).
Second Step Compound (t-28) (11.16 g, 30.6 mmol; 86.6%) was obtained by performing operations in a manner similar to the operations in the first step in Example 5, using compound (t-26) (7.35 g, 35.35 mmol) obtained in the first step, compound (t-27) (10.60 g, 37.90 mmol) prepared by a publicly known method, potassium carbonate (12.25 g, 88.64 mmol), tetrabutylammonium bromide (TBAB; 3.22 g, 9.99 mmol), toluene (35 mL), ethanol (35 mL), water (14 mL) and tetrakis(triphenylphosphine)palladium (0.39 g, 0.34 mmol).
Third Step Under a nitrogen atmosphere, compound (t-28) (1.86 g, 5.10 mmol) obtained in the second step, tetramethylethylenediamine (0.68 g, 5.85 mmol) and hexane (50 mL) were put in a reaction vessel, and cooled to 10° C. or lower. Then, n-butyllithium (1.60 M; n-hexane solution; 3.51 mL, 5.62 mmol) was added dropwise thereto in the temperature range of 0° C. to 10° C., and the resulting mixture was further stirred for 2 hours. A hexane (3 mL) solution of propionaldehyde (0.35 g, 6.03 mmol) was added dropwise thereto in the temperature range of 0° C. to 10° C., and the resulting mixture was stirred for 2 hours while being returned to room temperature. The resulting reaction mixture was poured into a saturated aqueous solution of ammonium chloride, and subjected to extraction with ethyl acetate. Organic layers combined were washed with water and saturated brine in the order, and dried over anhydrous sodium sulfate. The resulting solution was concentrated under reduced pressure, and the residue was purified by silica gel chromatography (volume ratio, heptane:ethyl acetate=4:1) to give compound (t-29) (0.64 g, 1.51 mmol; 29.7%).

operations in the fifth step in Example 1, using compound (t-29) (0.64 g, 1.51 mmol) obtained in the third step, dichloromethane (10 mL) and Dess-Martin periodinane (DMP; 0.66 g, 1.56 mmol).

$^1$H-NMR (CDCl$_3$) δ 7.64 (t, 1H), 7.45 (dd, 2H), 7.31 (d, 2H), 7.09 (d, 1H), 2.82 (q, 2H), 2.52 (tt, 1H), 1.91 (t, 4H), 1.55-1.03 (m, 12H), 0.91 (t, 3H).

Physical properties of compound (1-6-9) were as described below.

Phase transition temperature: C 74.5 I.

Example 8

Synthesis of Compound (1-8-3)

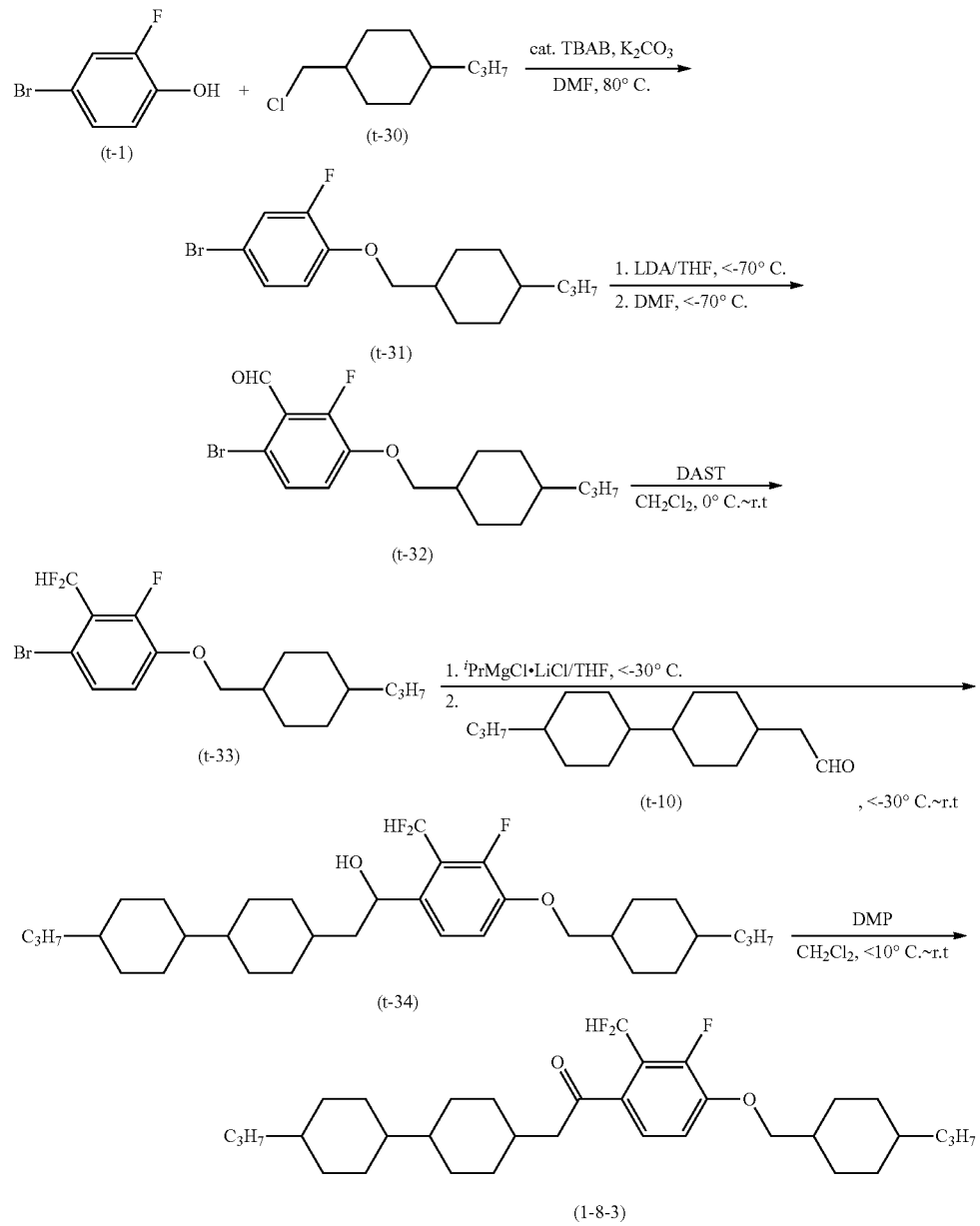

Fourth Step

Object compound (1-6-9) (0.40 g, 0.95 mmol; 62.9%) was obtained by performing operations in a manner similar to the First Step To a reaction vessel, 4-bromo-2-fluorophenol (t-1) (10 g, 52.36 mmol), compound (t-30) (10.98 g, 62.83 mmol), potassium carbonate (14.47 g, 100.71 mmol), tetrabutylammonium bromide (TBAB; 1.68 g, 5.24 mmol) and N,N-dimethylformamide (DMF; 150 mL) were put, and then the resulting mixture was stirred at 80° C. for 20 hours. The resulting reaction mixture cooled to room temperature was poured into saturated brine, and subjected to extraction with toluene. Organic layers combined were washed with water and saturated brine, and dried over anhydrous sodium sulfate. The resulting solution was concentrated under reduced pressure, and the residue was purified by column chromatography (filler: silica gel, eluate: hexane/ethyl acetate=20/1) to give compound (t-31) (13.18 g, 40.0 mmol; 76.4%).

Second Step

Compound (t-32) (7.5 g, 20.99 mmol; 93.6%) was obtained by performing operations in a manner similar to the operations in the second step in Example 1, using compound (t-31) (7 g, 21.26 mmol) obtained in the first step, THF (140 mL), a THF solution (1.09 M, 22.4 mL, 24.4 mmol) of lithium diisopropylamide (LDA) and N,N-dimethylformamide (DMF; 1.86 g, 25.5 mmol).

Third Step

Compound (t-33) (5.96 g, 15.7 mmol; 74.8%) was obtained by performing operations in a manner similar to the operations in the third step in Example 1, using compound (t-32) (7.5 g, 20.99 mmol) obtained in the second step, dichloromethane (80 mL) and diethylaminosulfur trifluoride (DAST; 7.1 g, 44.09 mmol).

Fourth Step

Compound (t-34) (6.54 g, 11.87 mmol; 77.2%) was obtained by performing operations in a manner similar to the operations in the fourth step in Example 1, using compound (t-33) (5.44 g, 14.34 mmol) obtained in the third step, a THF solution (1.3 M, 11.0 mL, 14.34 mmol) of isopropylmagnesium bromide (chloride, or the figure described above is erroneous) and lithium chloride, and compound (t-10) (2.99 g, 11.95 mmol).

Fifth Step

Object compound (1-8-3) (0.75 g, 1.37 mmol; 38%) was obtained by performing operations in a manner similar to the operations in the fifth step in Example 1, using compound (t-34) (2 g, 3.63 mmol) obtained in the fourth step, dichloromethane (60 mL) and Dess-Martin periodinane (DMP; 1.84 g, 4.36 mmol).

$^1$H-NMR (CDCl$_3$) δ 7.42 (d, 1H), 7.25 (t, 1H; CF$_2$H, J=53.6), 7.02 (t, 1H), 3.87 (d, 2H), 2.74 (d, 2H), 1.91-1.66 (m, 14H), 1.35-0.81 (m, 30H).

Physical properties of compound (1-8-3) were as described below.

Phase transition temperature: C 77.8 S$_B$ 97.2 S$_A$ 109.5 N 127.9 I.

Maximum temperature (NI)=121.6° C.; dielectric anisotropy (Δ∈)=−12.6×; optical anisotropy (Δn)=0.100.

Compounds (1-1-1) to (1-1-14), compounds (1-2-1) to (1-2-59), compounds (1-3-1) to (1-3-30), compounds (1-4-1) to (1-4-58), compounds (1-5-1) to (1-5-15), compounds (1-6-1) to (1-6-14), compounds (1-7-1) to (1-7-30), compounds (1-8-1) to (1-8-15), compounds (1-9-1) to (1-9-15), compounds (1-10-1) to (1-10-15) and compounds (1-A) to (1-D) described below can be prepared according to the method for preparing compound (1) as already described and preparation procedures described in Examples 1 to 5.

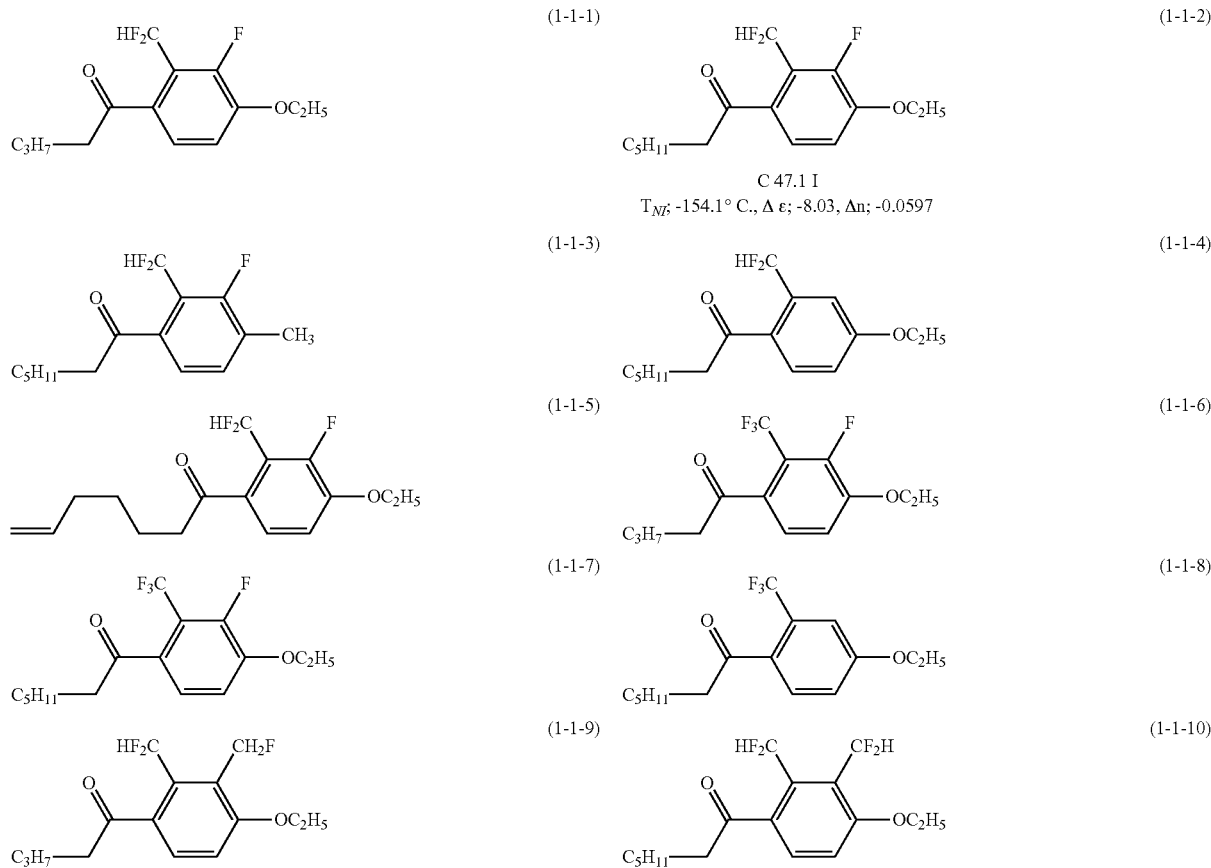

C 47.1 I
T$_{NI}$; -154.1° C., Δ ε; -8.03, Δn; -0.0597

-continued
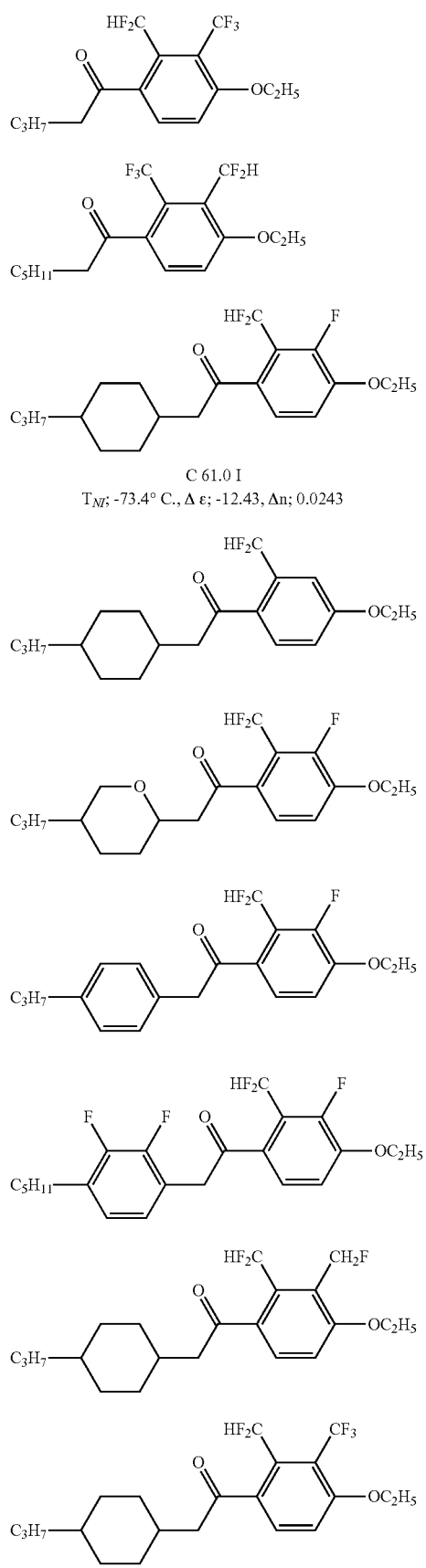
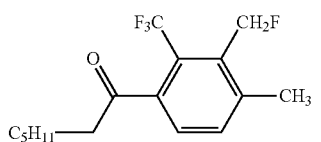
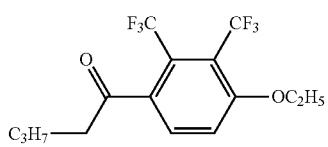
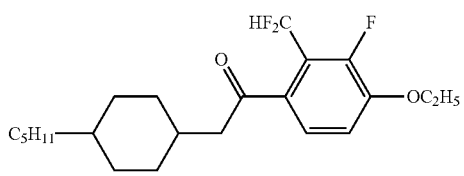
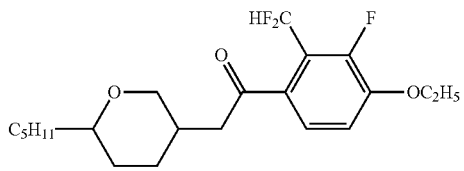
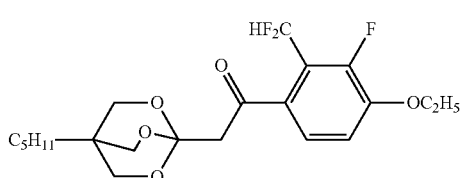
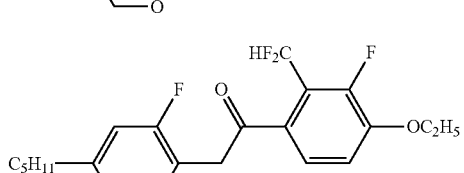
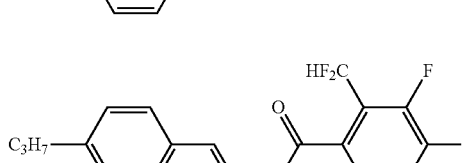
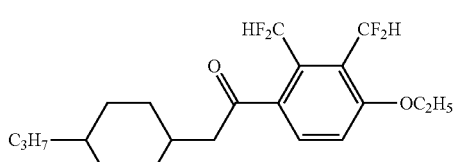
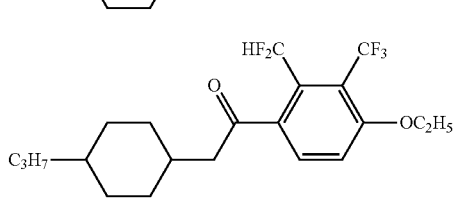

-continued (1-2-15)
(1-2-16)
(1-2-17)
(1-2-18)
(1-2-19)
(1-2-20)
(1-2-21)
(1-2-22)
(1-2-23)
(1-2-24)
(1-2-25)
(1-2-26)
(1-2-27)
(1-2-28)
(1-2-29)
(1-2-30)
(1-2-31)
(1-2-32)

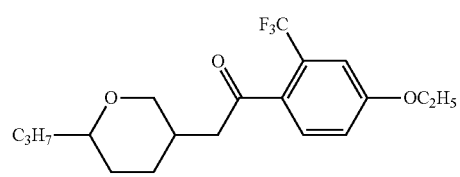 (1-2-33)
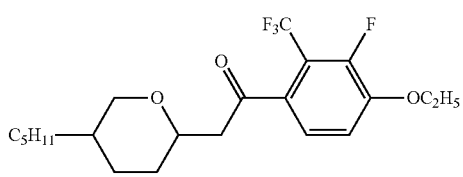 (1-2-34)
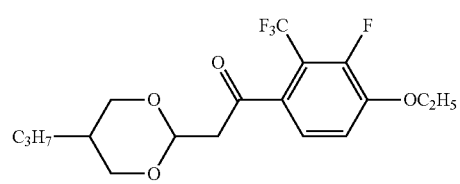 (1-2-35)
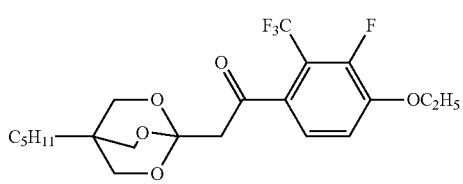 (1-2-36)
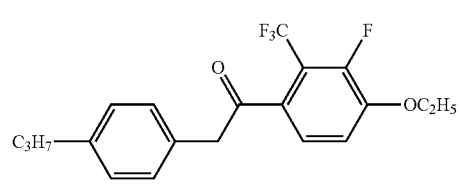 (1-2-37)
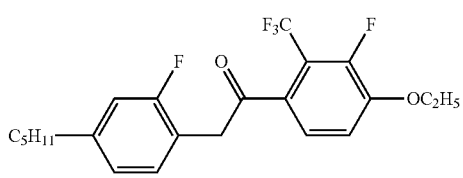 (1-2-38)
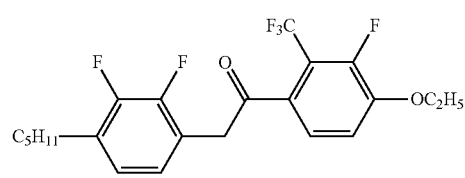 (1-2-39)
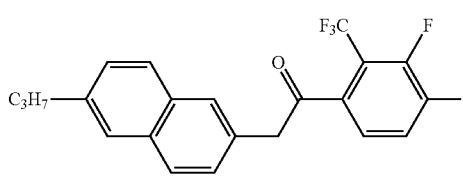 (1-2-40)
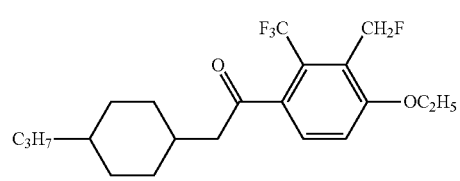 (1-2-41)
(1-2-42)
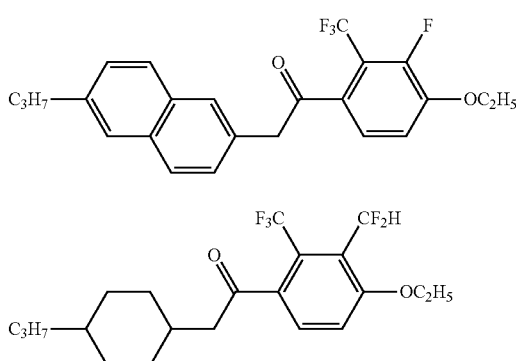
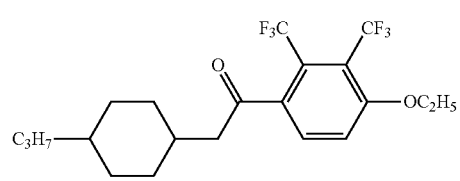 (1-2-43)
(1-2-44)
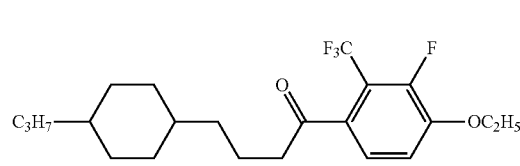 (1-2-45)
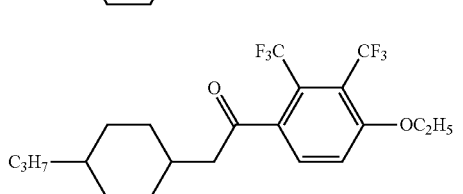 (1-2-46)
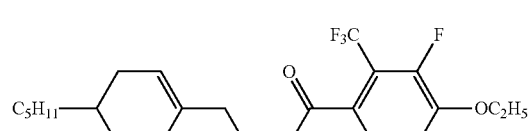 (1-2-47)
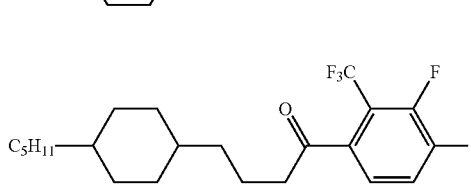 (1-2-48)
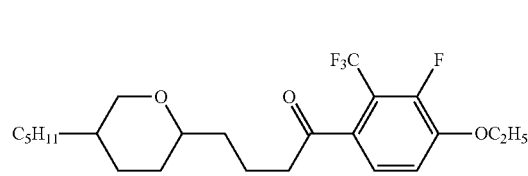 (1-2-49)
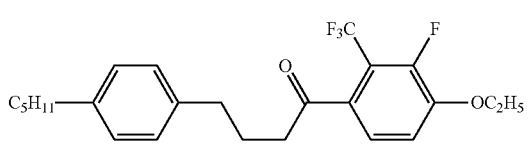 (1-2-50)

-continued
(1-2-51)
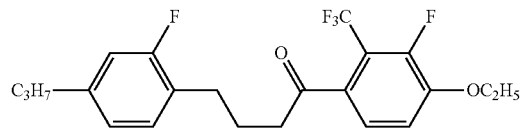
(1-2-52)
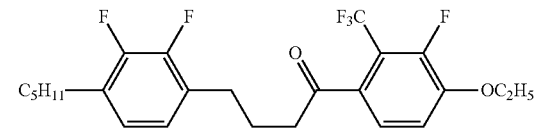
(1-2-53)
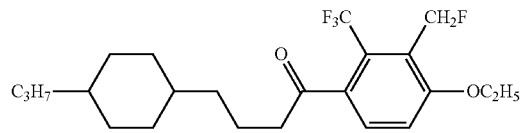
(1-2-54)
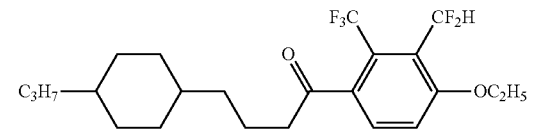
(1-2-55)
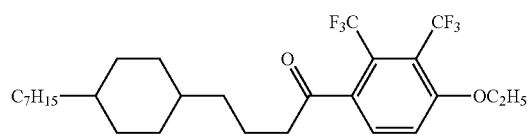
(1-2-56)
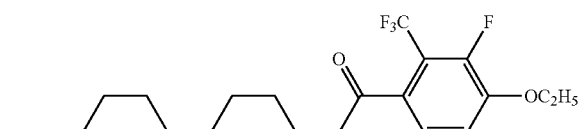
(1-2-57)
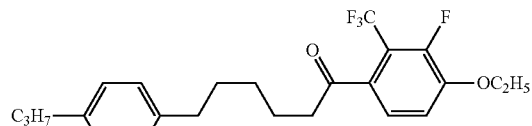
(1-2-58)
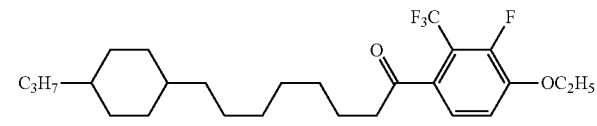
(1-2-59)
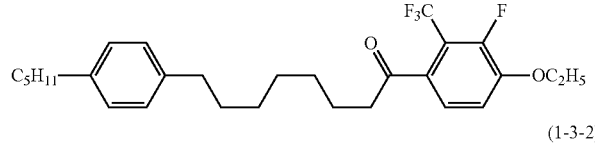
(1-3-1)
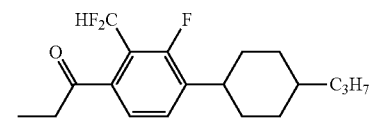
(1-3-2)
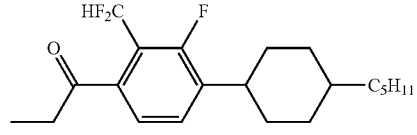
(1-3-3)
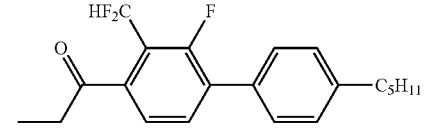
(1-3-4)
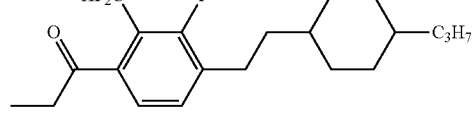
(1-3-5)
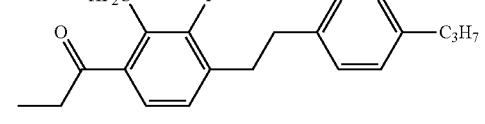
(1-3-6)
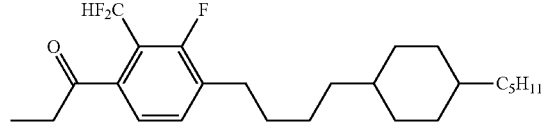
(1-3-7)
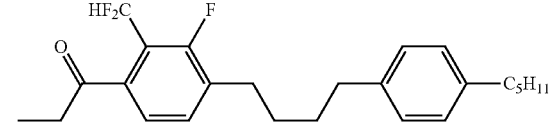
(1-3-8)
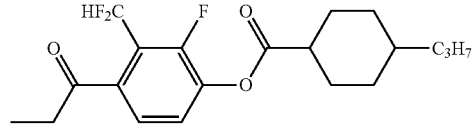
(1-3-9)
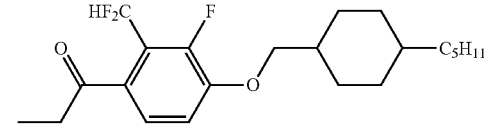
(1-3-10)
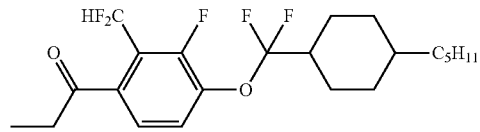
(1-3-11)
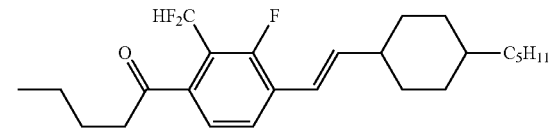

-continued
(1-3-12)
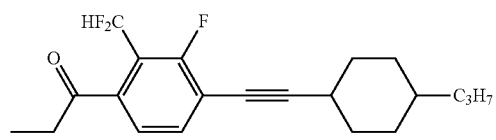
(1-3-13)
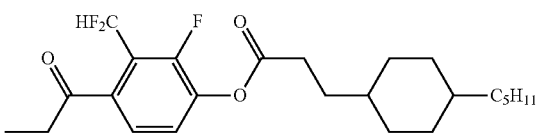
(1-3-14)
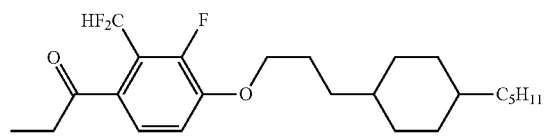
(1-3-15)
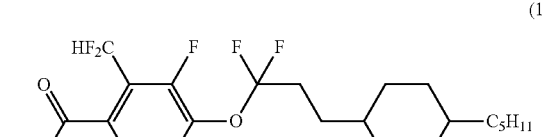
(1-3-16)
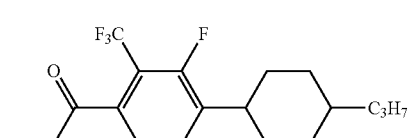
(1-3-17)
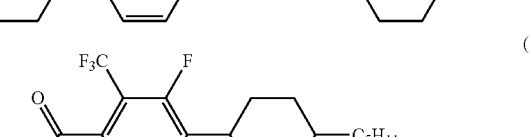
(1-3-18)
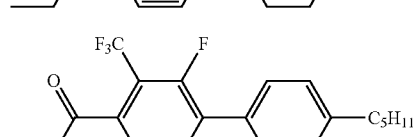
(1-3-19)
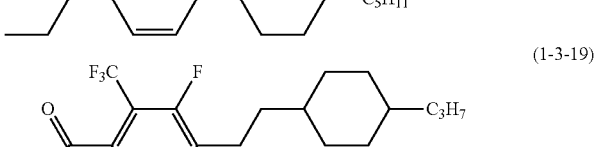
(1-3-20)
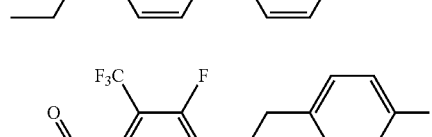
(1-3-21)
(1-3-22)
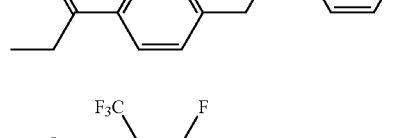
(1-3-23)
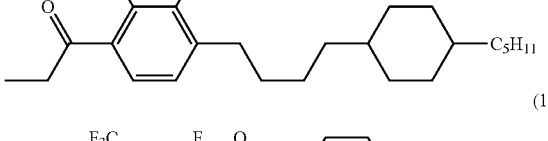
(1-3-24)
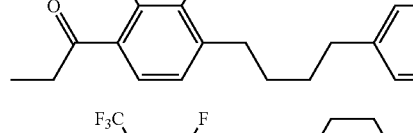
(1-3-25)
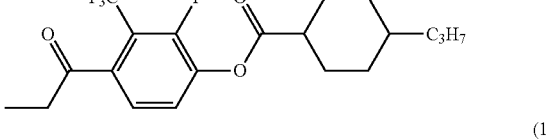
(1-3-26)
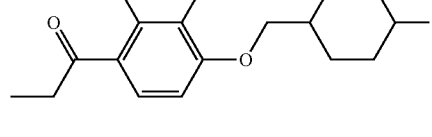
(1-3-27)
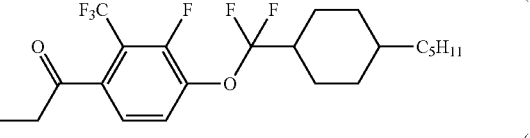
(1-3-28)
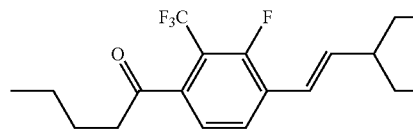
(1-3-29)
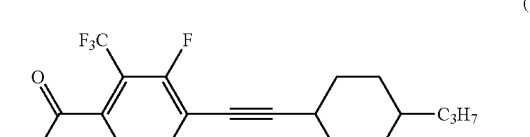
(1-3-30)
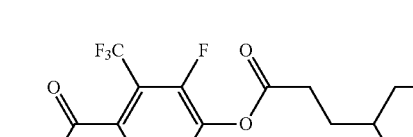
(1-4-1)
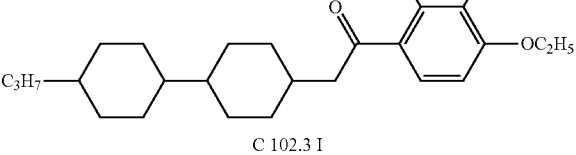
C 102.3 I
$T_{NI}$; 52.6° C., Δ ε; -13.26, Δn; 0.079

-continued
(1-4-2)
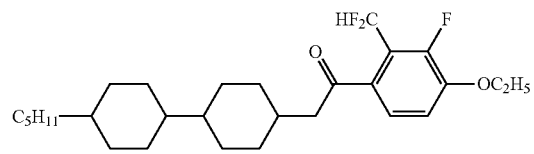
(1-4-3)
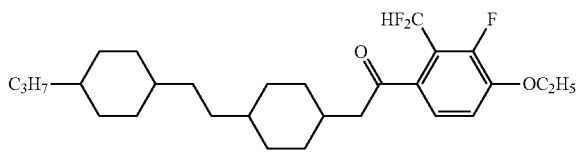
(1-4-4)
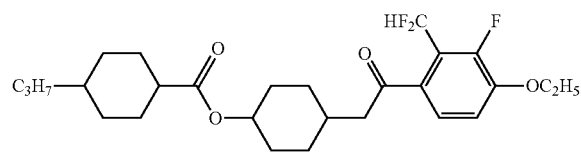
(1-4-5)
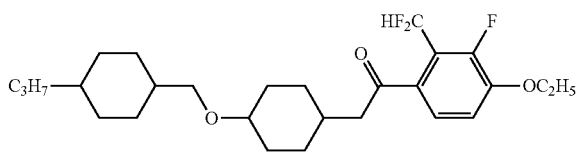
(1-4-6)
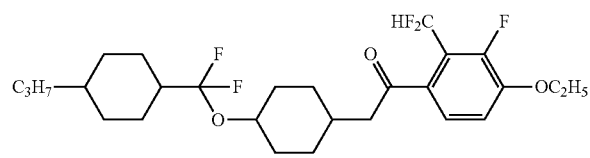
(1-4-7)
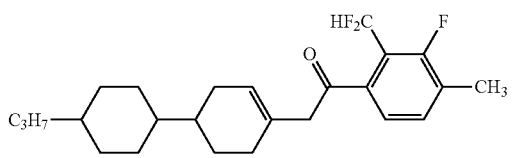
(1-4-8)
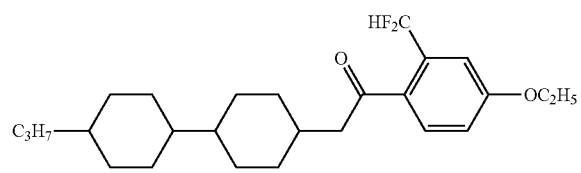
(1-4-9)
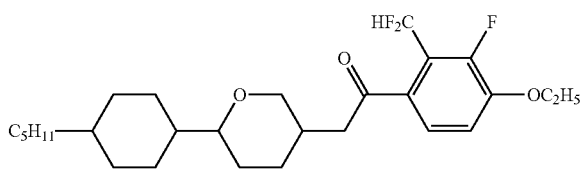
(1-4-10)
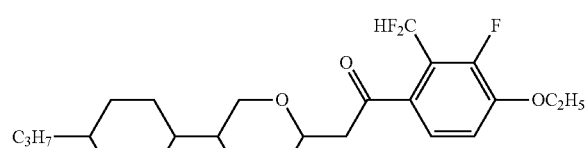
(1-4-11)
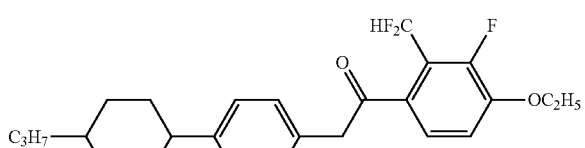
(1-4-12)
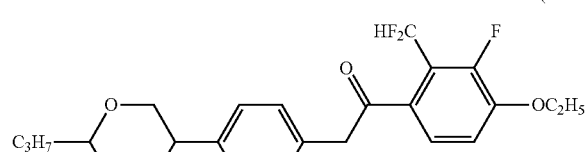
(1-4-13)
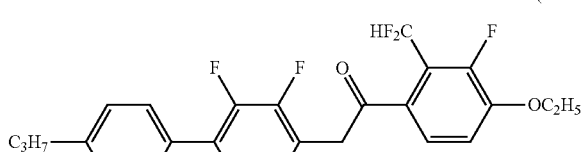
(1-4-14)
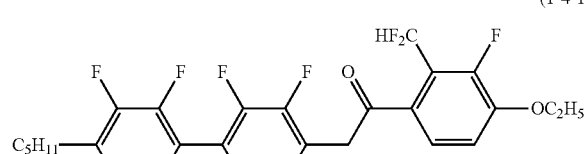
(1-4-15)
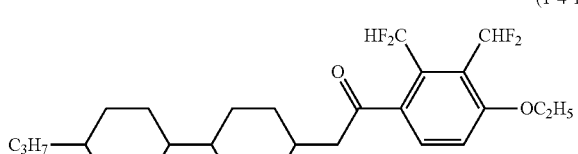
(1-4-16)
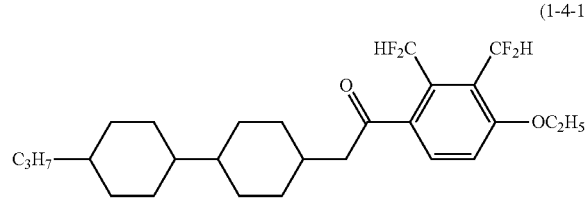
(1-4-17)
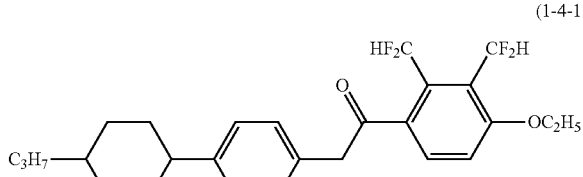

-continued
(1-4-18)
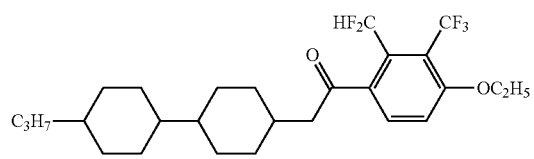
(1-4-19)
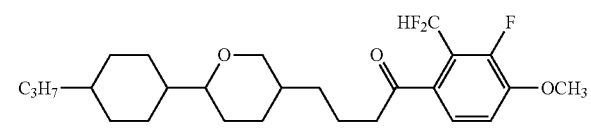
(1-4-20)
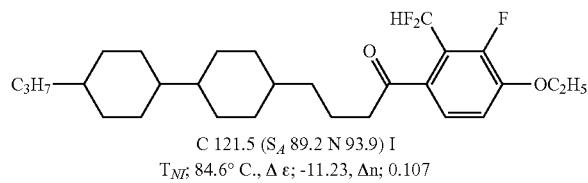
C 121.5 (S$_A$ 89.2 N 93.9) I
T$_{NI}$; 84.6° C., Δ ε; -11.23, Δn; 0.107
(1-4-21)
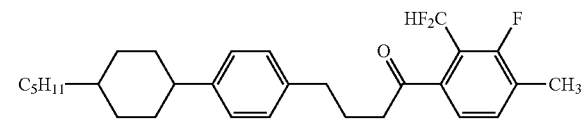
(1-4-22)
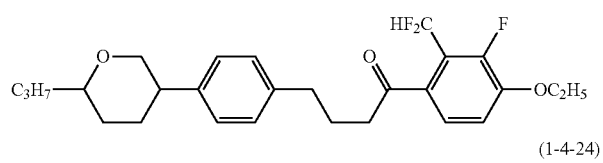
(1-4-23)
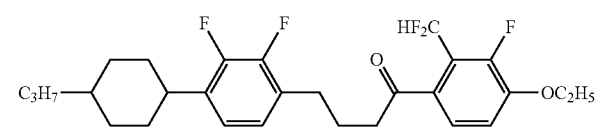
(1-4-24)
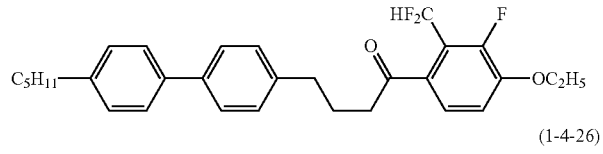
(1-4-25)
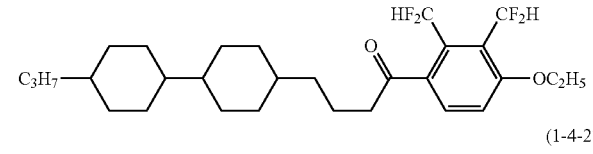
(1-4-26)
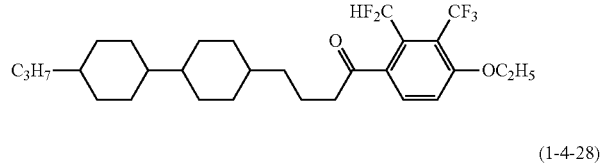
(1-4-27)
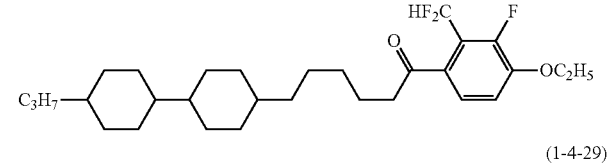
(1-4-28)
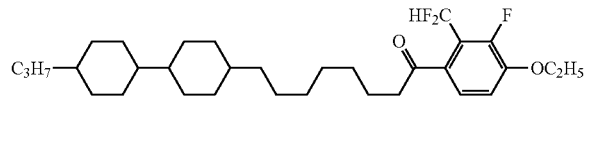
(1-4-29)
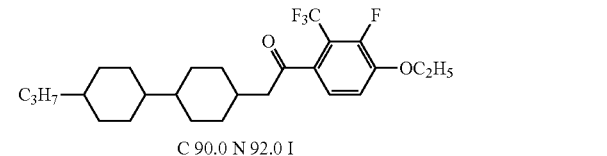
C 90.0 N 92.0 I
T$_{NI}$; 85.3° C., Δ ε; -8.8, Δn; 0.087
(1-4-30)
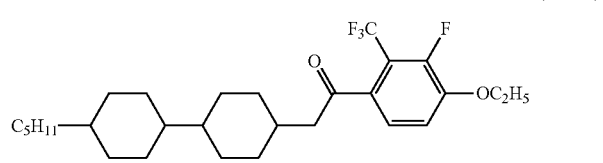
(1-4-31)
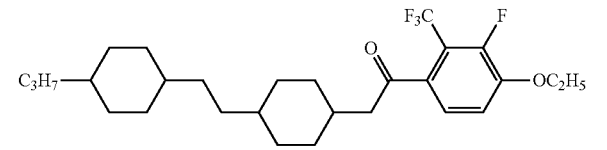
(1-4-32)
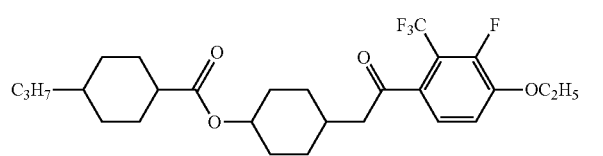
(1-4-33)
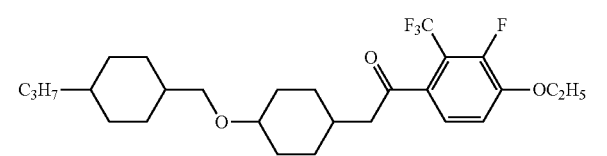
(1-4-34)
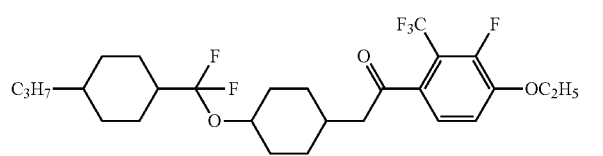
(1-4-35)
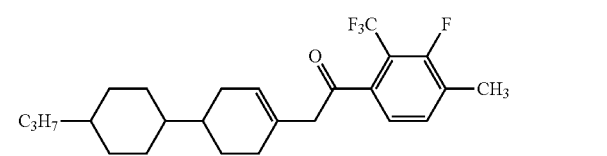

-continued
(1-4-36)
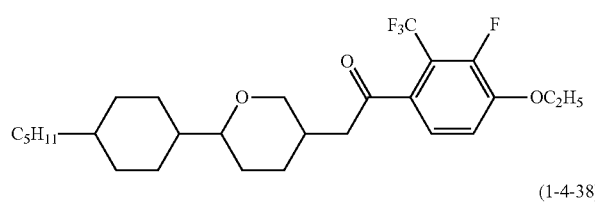
(1-4-37)
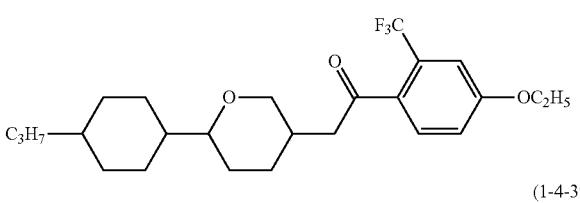
(1-4-38)
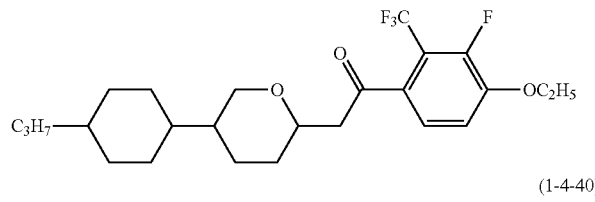
(1-4-39)
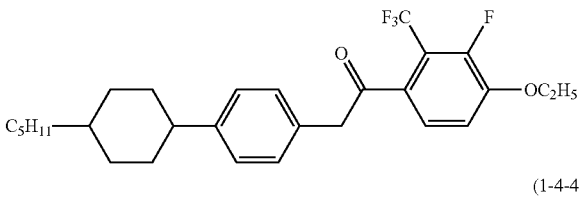
(1-4-40)
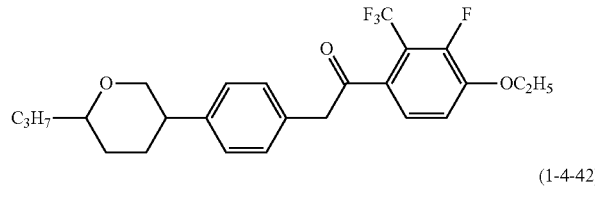
(1-4-41)
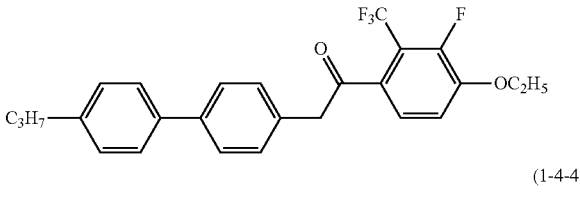
(1-4-42)
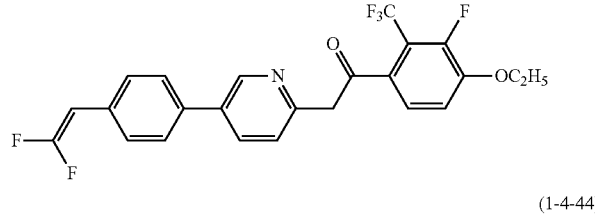
(1-4-43)
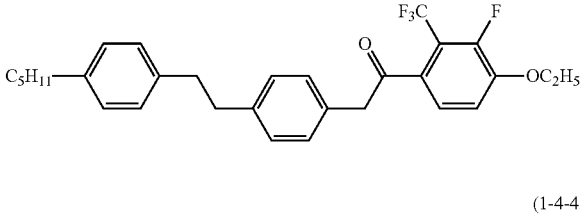
(1-4-44)
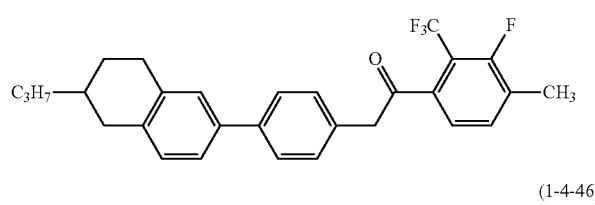
(1-4-45)
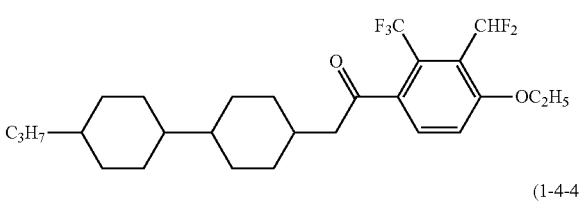
(1-4-46)
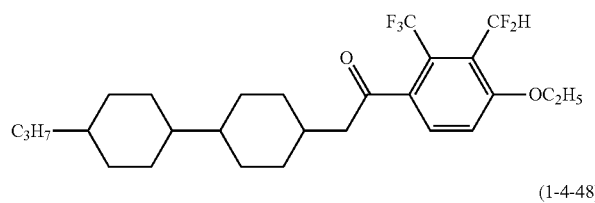
(1-4-47)
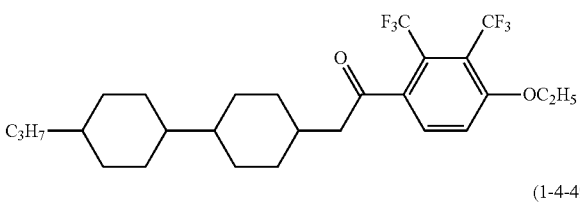
(1-4-48)
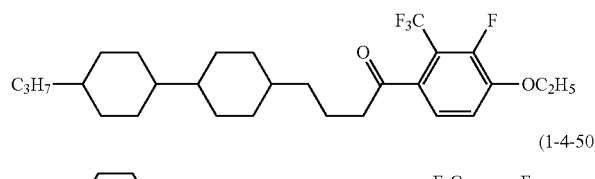
(1-4-49)
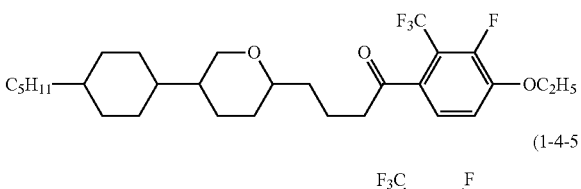
(1-4-50)
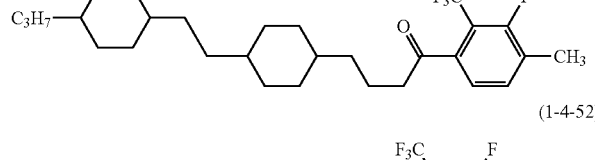
(1-4-51)
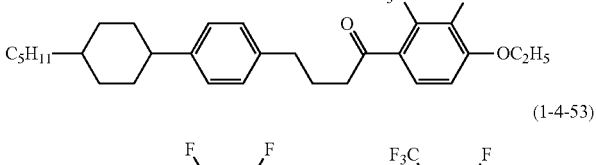
(1-4-52)
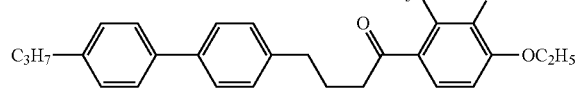
(1-4-53)

(1-4-54)
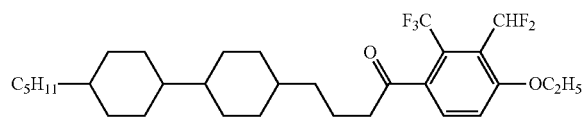
(1-4-55)
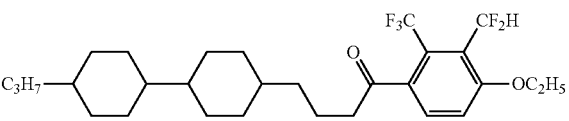
(1-4-56)
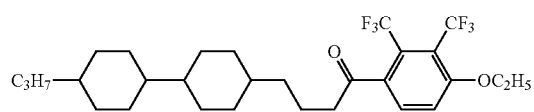
(1-4-57)
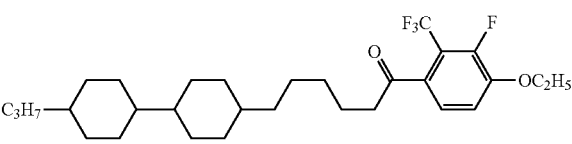
(1-4-58)
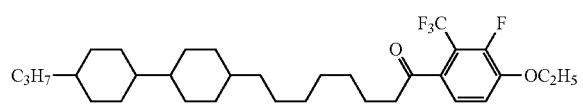
(1-5-1)
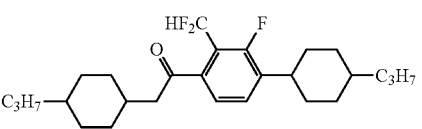
(1-5-2)
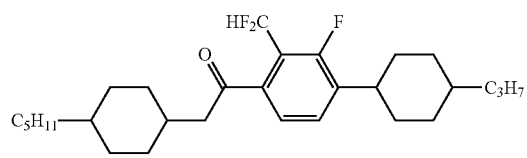
(1-5-3)
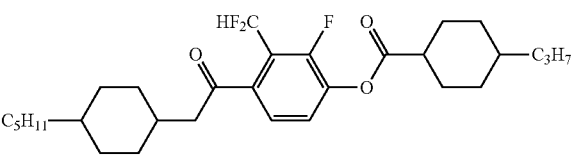
(1-5-4)
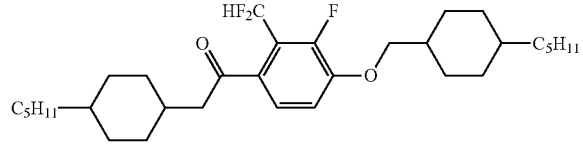
(1-5-5)
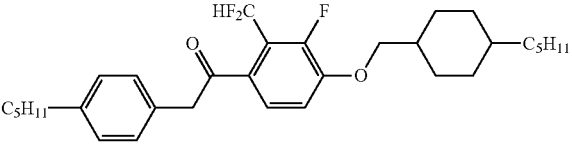
(1-5-6)
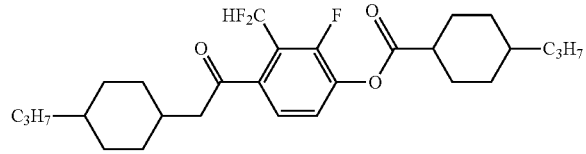
(1-5-7)
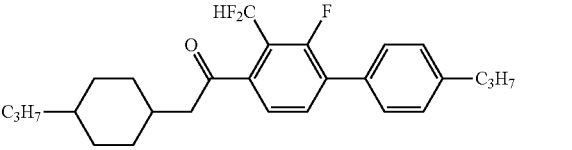
(1-5-8)
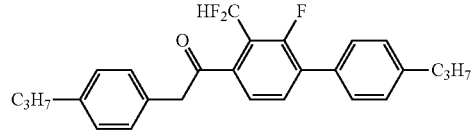
(1-5-9)
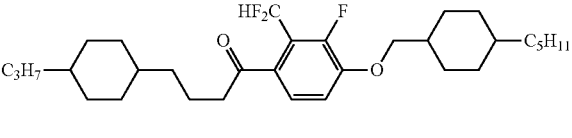
(1-5-10)
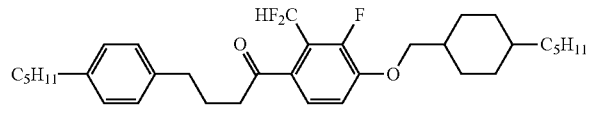
(1-5-11)
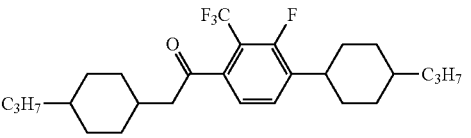
(1-5-12)
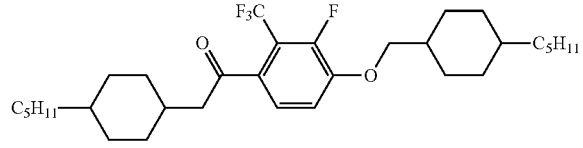
(1-5-13)
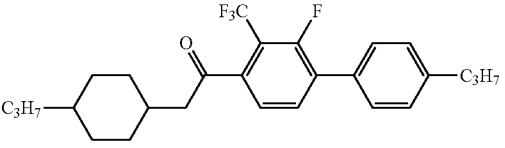

-continued
(1-5-14)
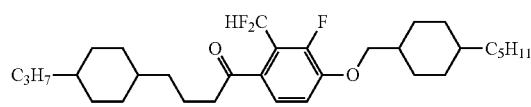
(1-5-15)
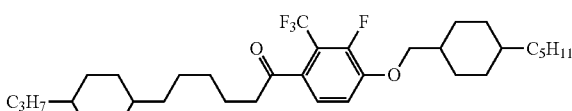
(1-6-1)
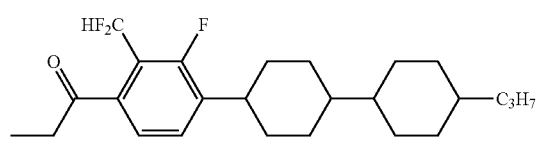
(1-6-2)
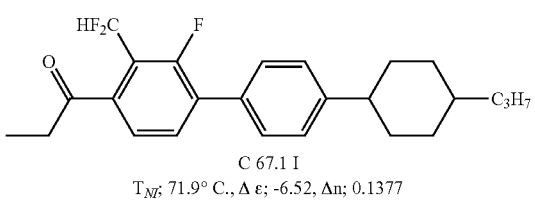
C 67.1 I
$T_{NI}$; 71.9° C., $\Delta\varepsilon$; -6.52, $\Delta n$; 0.1377
(1-6-3)
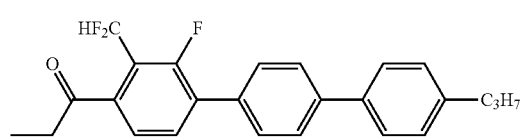
(1-6-4)
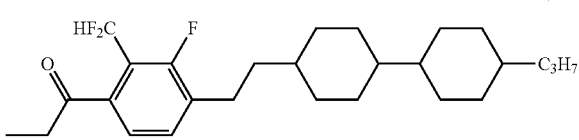
(1-6-5)
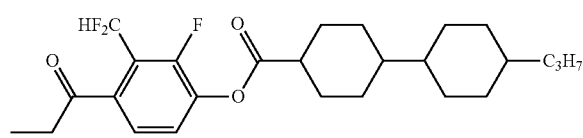
(1-6-6)
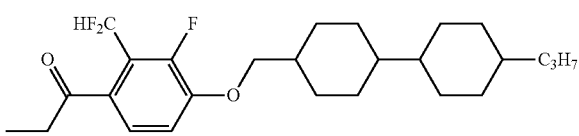
(1-6-7)
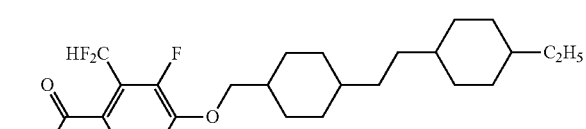
(1-6-8)
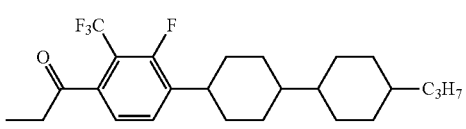
(1-6-9)
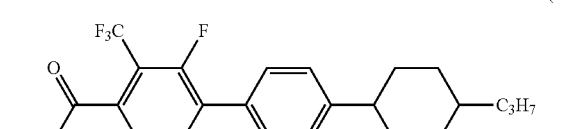
(1-6-10)
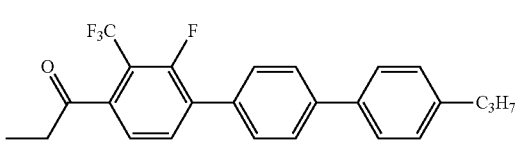
(1-6-11)
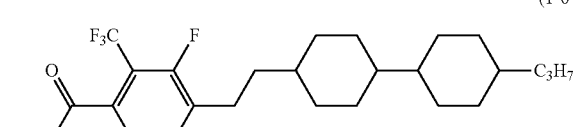
(1-6-12)
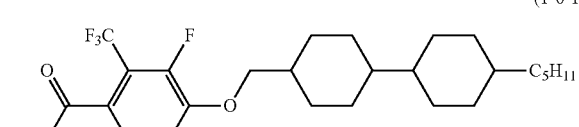
(1-6-13)
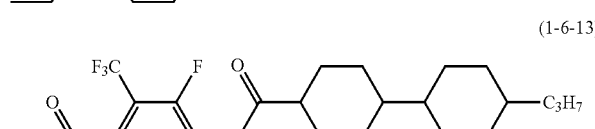
(1-6-14)
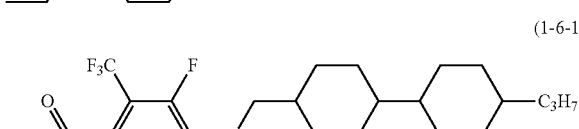
(1-7-1)
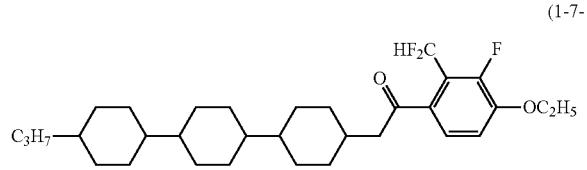
(1-7-2)
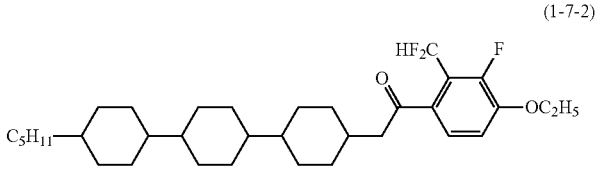

-continued
(1-7-3)
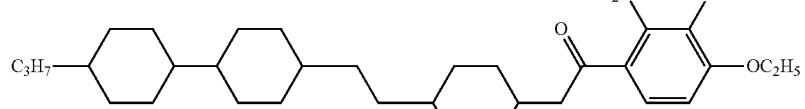
(1-7-4)
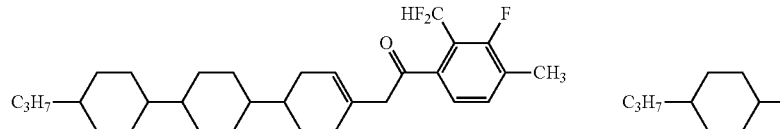
(1-7-5)
(1-7-6)
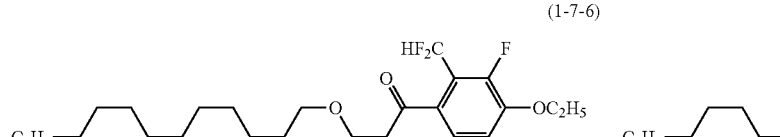
(1-7-7)
(1-7-8)
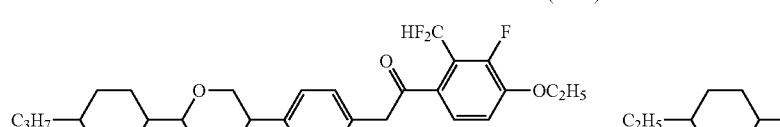
(1-7-9)
(1-7-10)
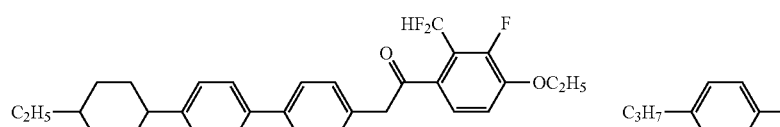
(1-7-11)
(1-7-12)
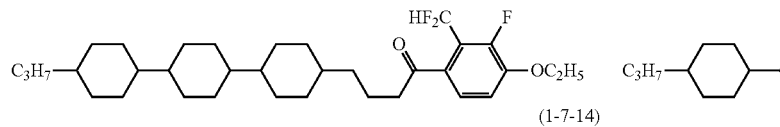
(1-7-13)
(1-7-14)
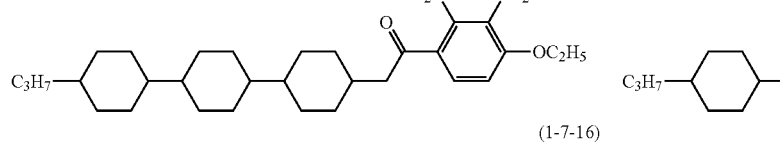
(1-7-15)
(1-7-16)
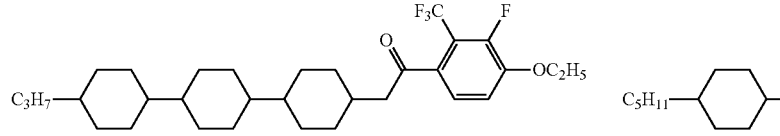
(1-7-17)
(1-7-18)
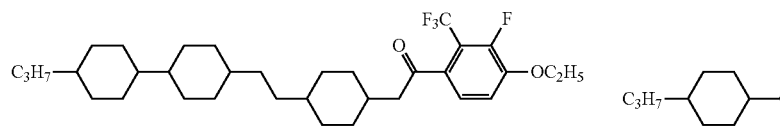
(1-7-19)
(1-7-20)
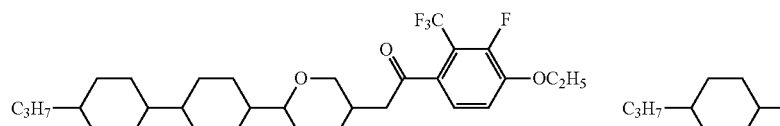
(1-7-21)

(1-7-22)
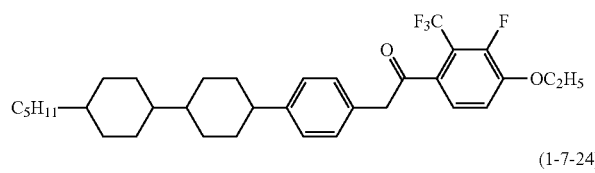
(1-7-23)
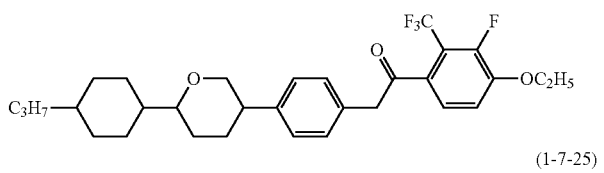
(1-7-24)
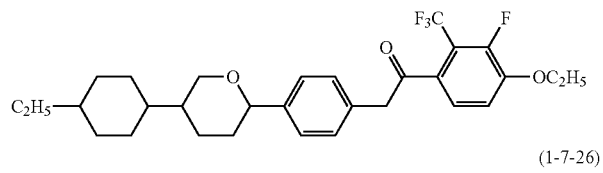
(1-7-25)
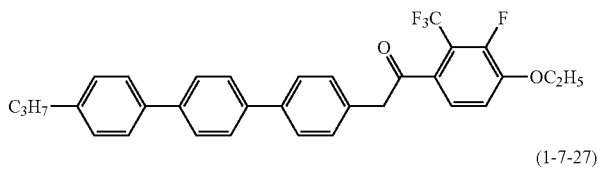
(1-7-26)
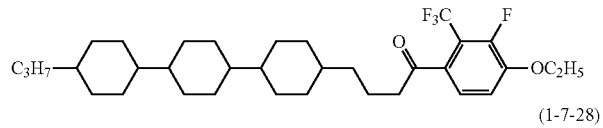
(1-7-27)
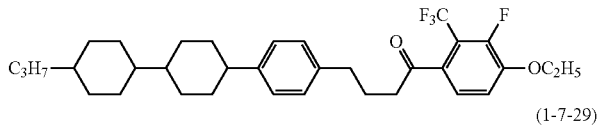
(1-7-28)
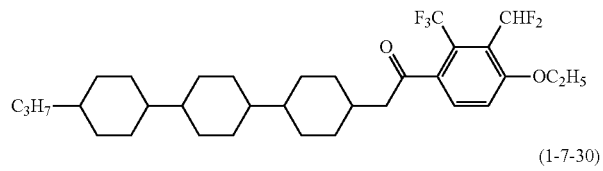
(1-7-29)
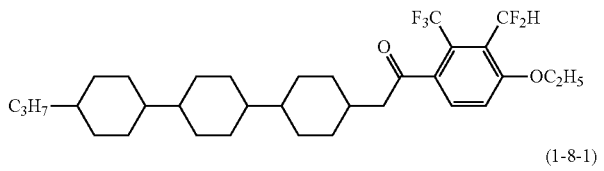
(1-7-30)
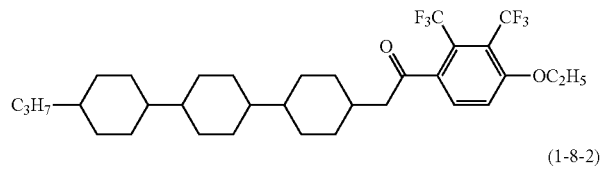
(1-8-1)
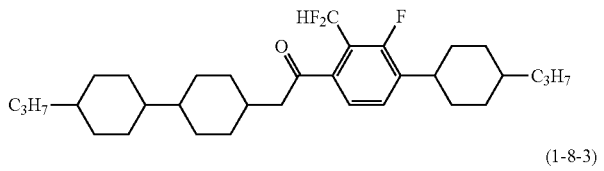
(1-8-2)
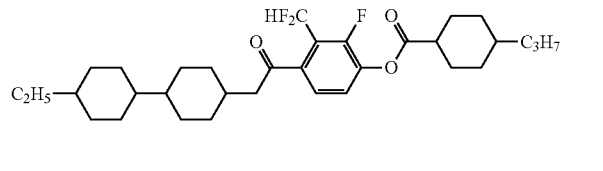
(1-8-3)
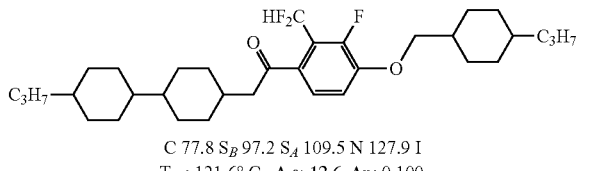
C 77.8 $S_B$ 97.2 $S_A$ 109.5 N 127.9 I
$T_{NI}$; 121.6° C., Δ ε; 12.6, Δn; 0.100
(1-8-4)
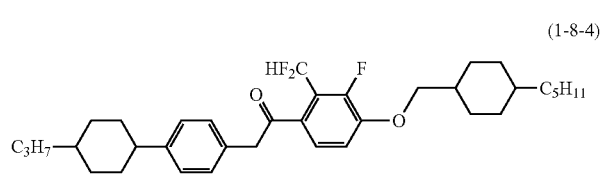
(1-8-5)
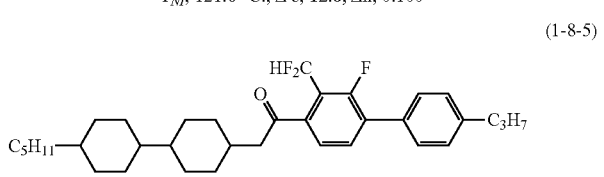
(1-8-6)
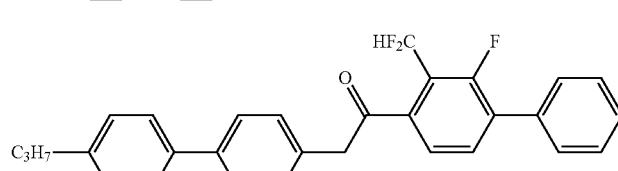
(1-8-7)
(1-8-8)

-continued
(1-8-9)
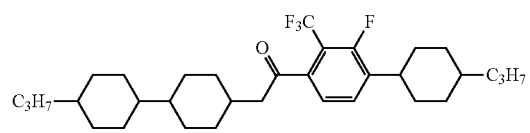
(1-8-10)
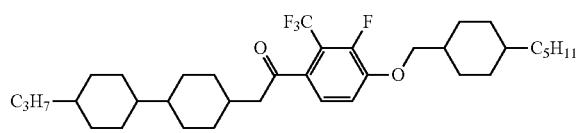
(1-8-11)
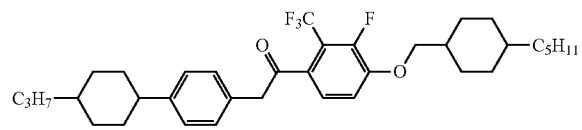
(1-8-12)
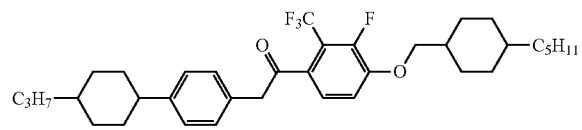
(1-8-13)
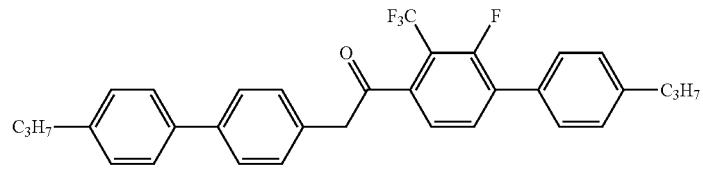
(1-8-14)
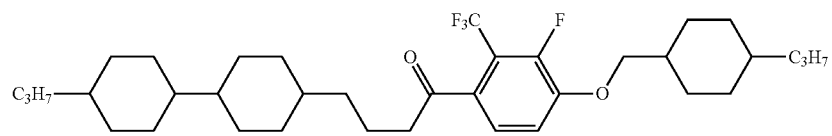
(1-8-15)
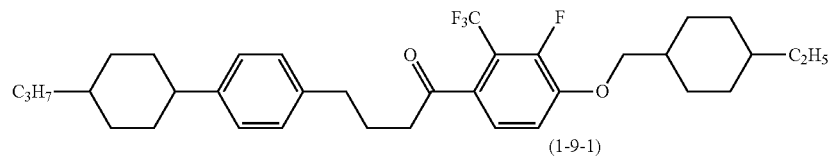
(1-9-1)
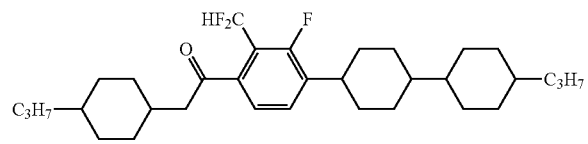
(1-9-2)
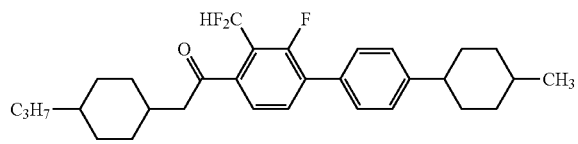
(1-9-3)
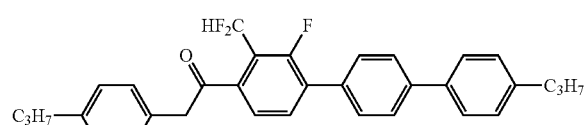
(1-9-4)
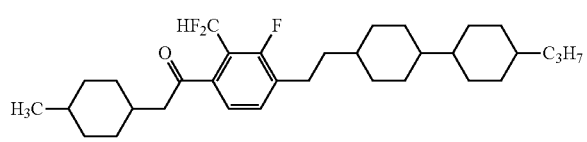
(1-9-5)
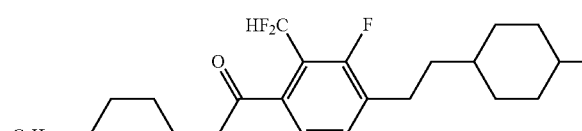
(1-9-6)
(1-9-7)
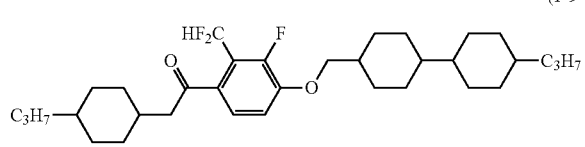
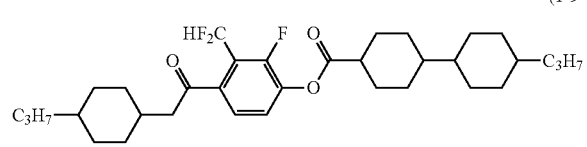
(1-9-8)
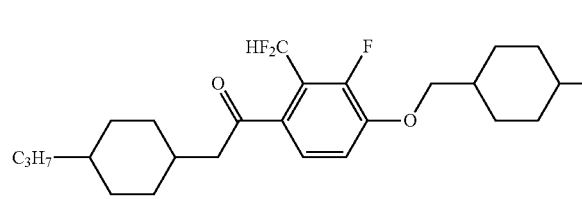

-continued
(1-9-9)
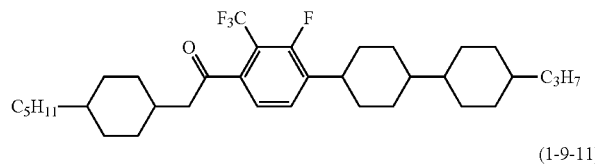
(1-9-10)
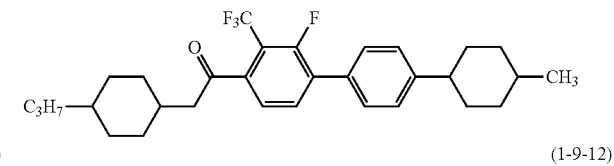
(1-9-11)
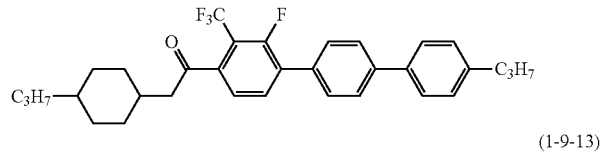
(1-9-12)
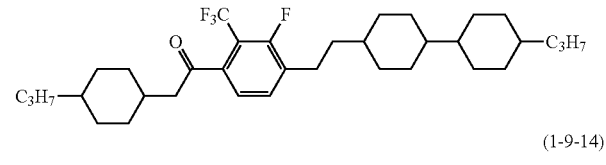
(1-9-13)
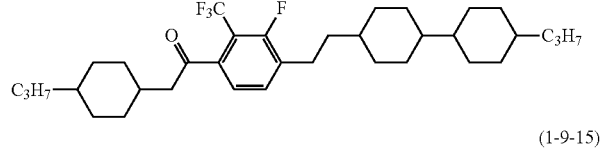
(1-9-14)
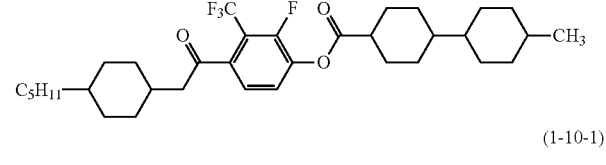
(1-9-15)
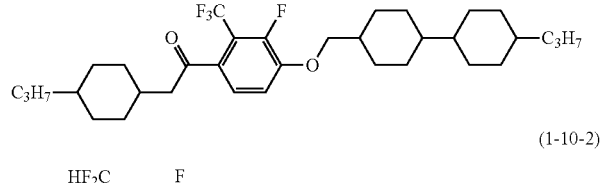
(1-10-1)
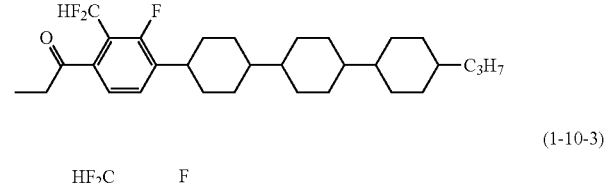
(1-10-2)
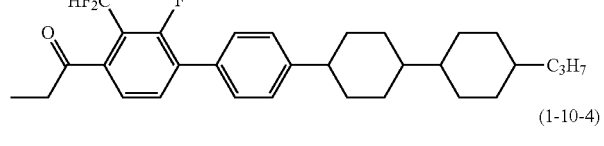
(1-10-3)
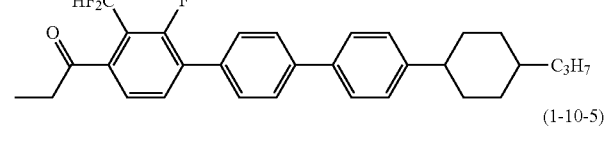
(1-10-4)
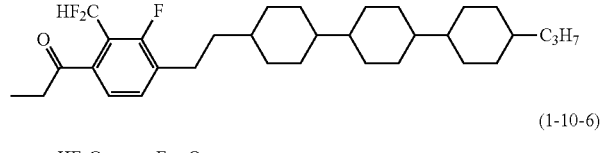
(1-10-5)
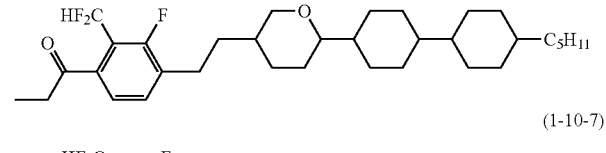
(1-10-6)
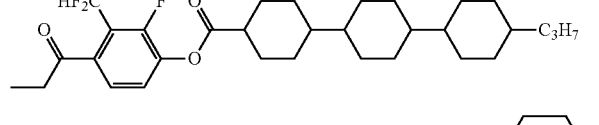
(1-10-7)
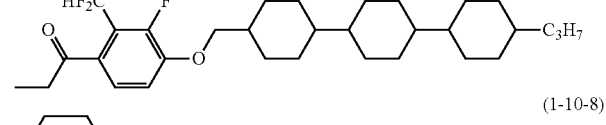
(1-10-8)
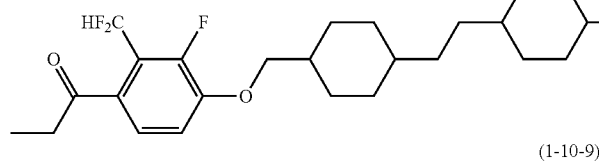
(1-10-9)
(1-10-10)
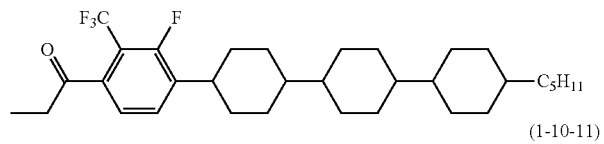
(1-10-11)
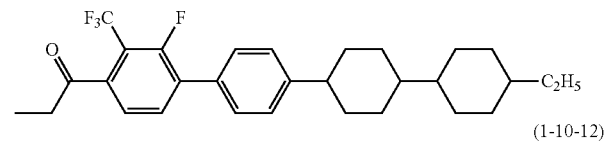
(1-10-12)
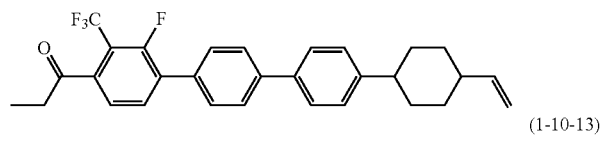
(1-10-13)
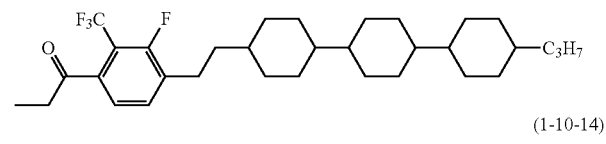
(1-10-14)

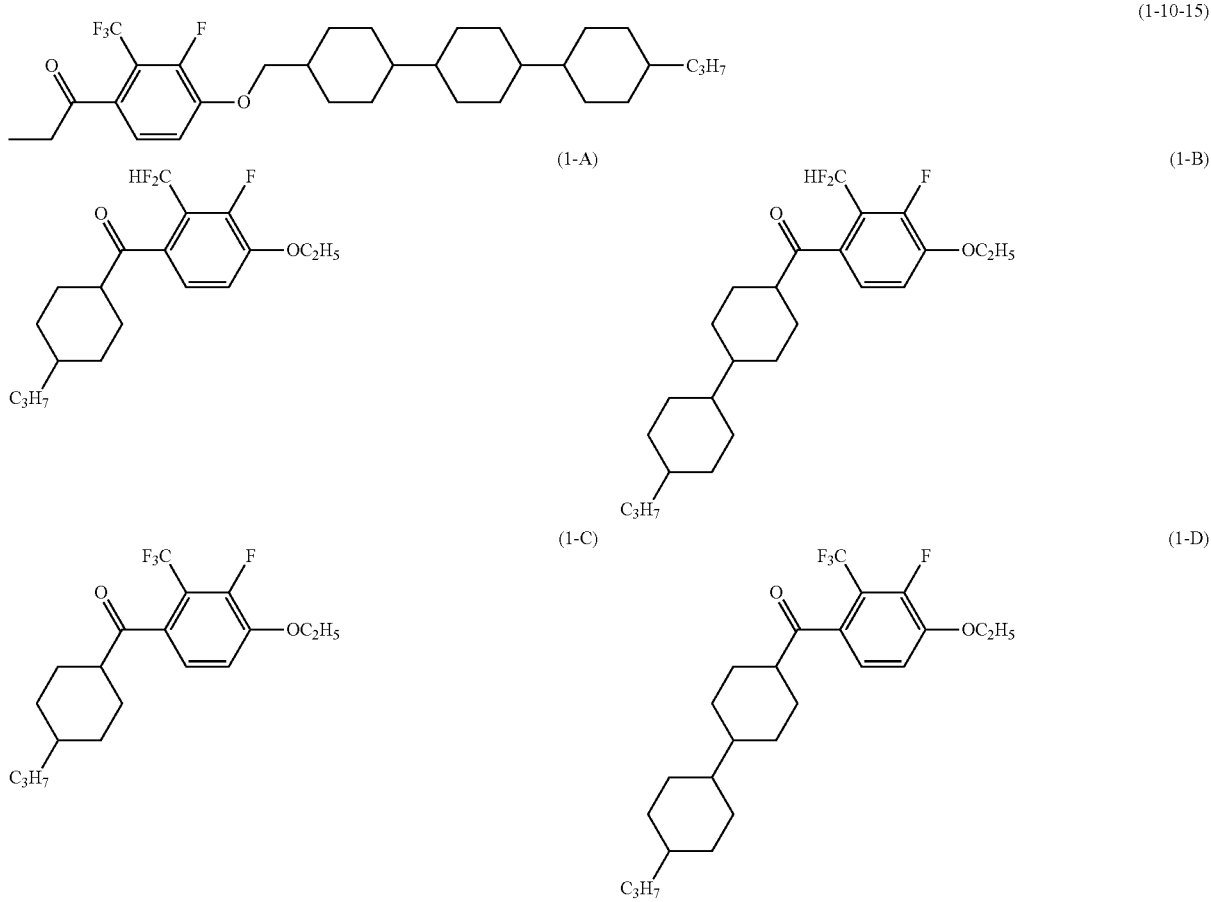

(1-10-15)

(1-A)

(1-B)

(1-C)

(1-D)

Comparative Example 1

Synthesis of Compound (CO-1)

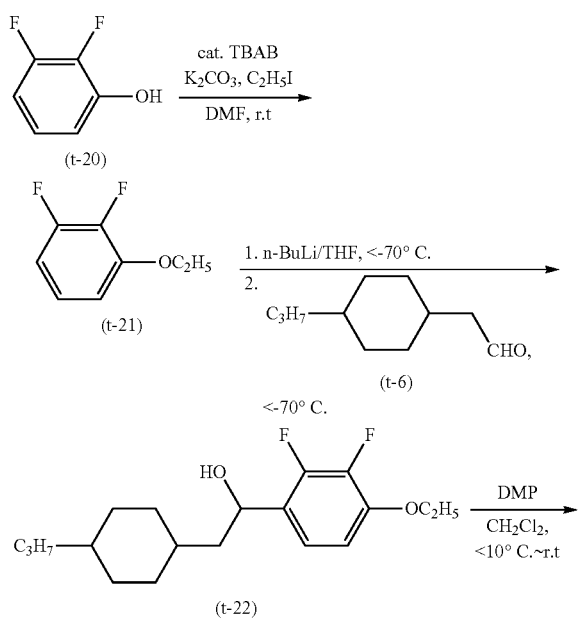

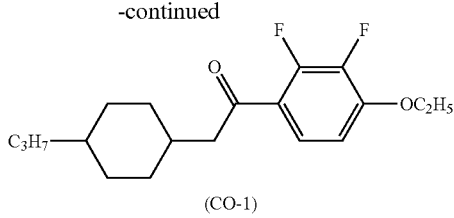

(CO-1)

First Step

Compound (t-21) (21.59 g, 136.5 mmol; 91%) was obtained by performing operations in a manner similar to the operations in the first step in Example 1, using 2,3-difluorophenol (t-20) (19.5 g, 150 mmol), potassium carbonate (41.46 g, 300 mmol), tetrabutylammonium bromide (TBAB; 2.42 g, 7.5 mmol), N,N-dimethylformamide (DMF; 200 mL) and ethyl iodide (46.8 g, mmol) in a reaction vessel.

Second Step

Under a nitrogen atmosphere, compound (t-21) (5.6 g, 35.4 mmol) obtained in the first step and THF (100 mL) were put in a reaction vessel, and cooled to −70° C. or lower, and n-butyllithium (n-BuLi; 1.60 M, 24.3 mL, 38.9 mmol) was added dropwise thereto at −70° C. or lower, and then the resulting mixture was stirred for 1 hour. Next, a THF (15 mL) solution of compound (t-6) (5.96 g, 35.4 mmol) was added dropwise thereto. The resulting mixture was stirred at −70° C. for 2 hours, and then the resulting reaction mixture was poured into an ice-added aqueous solution of ammonium chloride, and stirred for 15 minutes. The resulting reaction liquid was separated into an organic layer and an aqueous layer, and then the aqueous layer was subjected to extraction with ethyl acetate. Organic layers combined were washed with water and saturated brine, and dried over anhydrous sodium sulfate. The resulting solution was concentrated under reduced pressure, and the residue was purified by column chromatography (filler: silica gel, eluate: hexane/ethyl acetate=4/1) to give compound (t-22) (9.38 g, 28.74 mmol; 81.2%).

Third Step

Object compound (CO-1) (6.57 g, 20.26 mmol; 70.5%) was obtained by performing operations in a manner similar to the operations in the fifth step in Example 1, using compound (t-22) (9.38 g, 28.74 mmol) obtained in the second step, dichloromethane (100 mL) and Dess-Martin periodinane (DMP; 14.6 g, 34.5 mmol).

$^1$H-NMR (CDCl$_3$) δ 7.10 (td, 1H), 6.72 (td, 1H), 4.18 (q, 2H), 2.70 (d, 2H), 1.85-1.70 (m, 5H), 1.51 (t, 3H), 1.35-1.12 (m, 4H), 1.02-0.90 (m, 4H), 0.86 (t, 3H).

Physical properties of compound (CO-1) were as described below.

Phase transition temperature: C 86.7 I.

Maximum temperature (NI)=27.6° C.; dielectric anisotropy (Δ∈)=1.19; optical anisotropy (Δn)=0.107.

Thus, compound (1-2-1) of the invention was found to have a larger negative dielectric anisotropy in comparison with the dielectric anisotropy of compound (CO-1).

Comparative Example 2

Physical Properties of Compound (t-11)

Physical properties of compound (t-11) obtained in the first step in Example 3 will be described below.

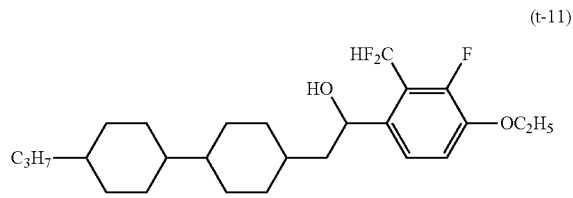

(t-11)

$^1$H-NMR (CDCl$_3$) δ 7.45 (d, 1H), 7.12 (t, 1H; CF$_2$H, J=53.5), 7.06 (t, 1H), 5.27 (d, 1H), 4.12 (q, 2H), 1.80-1.65 (m, 6H), 1.51 (t, 3H), 1.32-1.11 (m, 10H), 1.01-0.82 (m, 13H).

Physical properties of compound (t-11) were as described below.

Phase transition temperature: C 132.4 I.

Maximum temperature (NI)=92.6° C.; dielectric anisotropy (Δ∈)=−1.39; optical anisotropy (Δn)=0.093.

Thus, compound (1-4-1) of the invention was found to have a larger negative dielectric anisotropy in comparison with the dielectric anisotropy of compound (t-11).

Comparative Example 3

Synthesis of Compound (CO-3)

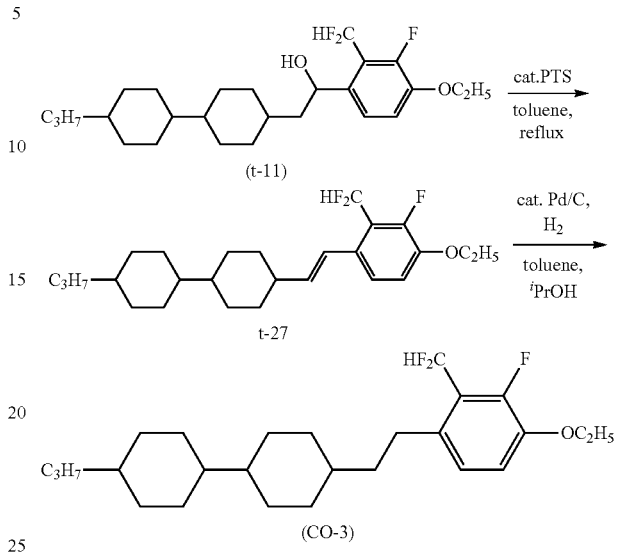

First Step

Compound (t-11) (1.0 g, 2.27 mmol) obtained in the first step in Example 3 and p-toluenesulfonic acid (60 mg, 0.33 mmol) were heated and refluxed in toluene (20 mL) for 1 hour. The resulting reaction liquid was cooled to room temperature, and then washed with saturated sodium bicarbonate water, water and saturated brine, and then dried over anhydrous sodium sulfate. The resulting solution was concentrated under reduced pressure, and the residue was purified by silica gel chromatography (volume ratio, heptane: ethyl acetate=20:1) and recrystallization (solvent; heptane) to give compound (t-27) (0.815 g, 1.93 mmol; 85%).

Second Step

Compound (t-27) (0.815 g, 1.93 mmol) and 5% palladium on carbon (50 mg) were mixed in toluene (5 mL) and isopropanol (5 mL), and then the resulting mixture was stirred under a hydrogen atmosphere for 3 hours. The resulting reaction liquid was filtrated, and then the resulting filtrate was condensed, and the residue was purified by silica gel chromatography (volume ratio, heptane:ethyl acetate=20:1) and recrystallization (solvent; heptane) to give compound (CO-3) (0.54 g, 1.27 mmol; 66%).

$^1$H-NMR (CDCl$_3$) δ 7.42 (d, 1H), 7.05 (t, 1H; CF$_2$H, J=53.3), 7.04 (t, 1H), 4.05 (q, 2H), 2.58 (t, 2H), 1.85-1.66 (m, 6H), 1.48-1.10 (m, 10H), 1.05-0.82 (m, 16H).

Physical properties of compound (CO-3) were as described below.

Phase transition temperature: C 68.0 N 112.8 I.

Maximum temperature (NI)=110.6° C.; dielectric anisotropy (Δ∈)=−6.86; optical anisotropy (Δn)=0.078.

Thus, compound (1-4-1) of the invention was found to have a larger negative dielectric anisotropy in comparison with the dielectric anisotropy of compound (CO-3).

1-2. Example of Composition (1)

Liquid crystal composition (1) of the invention will be described in detail by way of Examples. Compounds in Examples were expressed using symbols according to definitions in Table 1 described below. In the Table, a configuration of 1,4-cyclohexylene is trans. A parenthesized number next to a symbolized compound in Examples corresponds to the number of the compound. A symbol (-) means any other liquid crystal compound. A ratio (percentage) of a liquid crystal compound is expressed in terms of weight percentage (% by weight) based on the total weight of the liquid crystal composition. Values of physical properties of the composition were summarized in a last part. The physical properties were measured according to the methods described above, and were directly described without extrapolating the measured values.

TABLE 1

Method for Description of Compounds using Symbols
R—(A$_1$)—Z$_1$—...—Z$_n$—(A$_n$)—R'

| 1) Left-terminal Group R— | Symbol |
| --- | --- |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |
| C$_n$H$_{2n+1}$—CO— | nK— |

| 2) Right-terminal group —R' | Symbol |
| --- | --- |
| —C$_n$H$_{2n+1}$ | -n |
| —OC$_n$H$_{2n+1}$ | —On |
| —COOCH$_3$ | -EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —CF=CH—CF$_3$ | —FVCF3 |
| —C≡N | —C |
| —CO—C$_n$H$_{2n+1}$ | —Kn |

| 3) Bonding Group —Z$_n$— | Symbol |
| --- | --- |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| —C$_n$H$_{2n}$—K— | nK |

| 4) Ring Structure —A$_n$— | Symbol |
| --- | --- |
| (cyclohexane) | H |
| (benzene) | B |
| (fluorobenzene) | B(F) |

TABLE 1-continued

Method for Description of Compounds using Symbols
R—(A$_1$)—Z$_1$—...—Z$_n$—(A$_n$)—R'

| Structure | Symbol |
| --- | --- |
| (2-fluorobenzene) | B(2F) |
| (3,5-difluorobenzene) | B(F,F) |
| (2,3-difluorobenzene) | B(2F,3F) |
| (2-fluoro-3-chlorobenzene) | B(2F,3CL) |
| (2-CF$_2$H-3-fluorobenzene) | B(2CF2H,3F) |
| (2-fluoro-3-CF$_2$H-benzene) | B(2F,3CF2H) |
| (2-CF$_3$-3-fluorobenzene) | B(2CF3,3F) |
| (2-fluoro-3-CF$_3$-benzene) | B(2F,3CF3) |
| (2,3-bis-CF$_2$H-benzene) | B(2CF2H,3CF2H) |

TABLE 1-continued

Method for Description of Compounds using Symbols
$R—(A_1)—Z_1—\ldots—Z_n—(A_n)—R'$

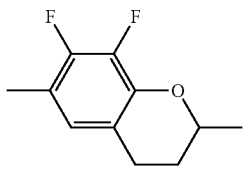  Cro(7F,8F)

5) Examples of Description

Example 1  3-HH1KB(2CF2H,3F)—O2

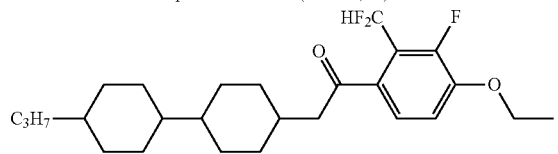

Example 2  3-HBB(2F,3F)—O2

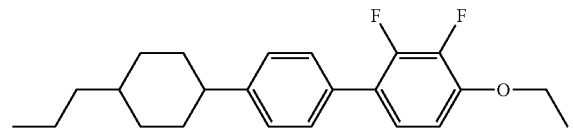 [SMILES: CCCC1CCC(c2ccc(-c3ccc(OCC)c(F)c3F)cc2)CC1]

Example 9

Use Example 1

| | | |
|---|---|---|
| 6K—B(2CF2H,3F)—O2 | (1-1-2) | 5% |
| 3-HB—O1 | (13-5) | 15% |
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 13% |
| 5-HHB(2F,3F)—O2 | (7-1) | 13% |
| 3-HHB-1 | (14-1) | 6% |

NI=75.8° C.; $\Delta n$=0.086; $\Delta\epsilon$=−3.8; $\eta$=40.5 mPa·s.

Example 10

Use Example 2

| | | |
|---|---|---|
| 3-H1KB(2CF2H,3F)—O2 | (1-2-1) | 3% |
| 5-HB—O2 | (13-5) | 9% |
| 3-H2B(2F,3F)—O2 | (6-4) | 20% |
| 5-H2B(2F,3F)—O2 | (6-4) | 20% |
| 2-HHB(2F,3CL)—O2 | (7-12) | 2% |
| 3-HHB(2F,3CL)—O2 | (7-12) | 3% |
| 4-HHB(2F,3CL)—O2 | (7-12) | 2% |
| 5-HHB(2F,3CL)—O2 | (7-12) | 2% |
| 3-HBB(2F,3F)—O2 | (7-7) | 9% |
| 5-HBB(2F,3F)—O2 | (7-7) | 9% |
| V—HHB-1 | (14-1) | 6% |
| 3-HHB-3 | (14-1) | 6% |
| 3-HHEBH-3 | (15-6) | 3% |
| 3-HHEBH-4 | (15-6) | 3% |
| 3-HHEBH-5 | (15-6) | 3% |

NI=91.9° C.; $\Delta n$=0.100; $\Delta\epsilon$=−4.3; $\eta$=33.4 mPa·s.

Example 11

Use Example 3

| | | |
|---|---|---|
| 3-HH1KB(2CF2H,3F)—O2 | (1-4-1) | 5% |
| 3-HB—O1 | (13-5) | 15% |
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 13% |
| 5-HHB(2F,3F)—O2 | (7-1) | 13% |
| 6-HEB(2F,3F)—O2 | (6-6) | 6% |

NI=81.3° C.; $\Delta n$=0.090; $\Delta\epsilon$=−4.4; $\eta$=41.7 mPa·s.

Example 12

Use Example 4

| | | |
|---|---|---|
| 3-HH3KB(2CF2H,3F)—O2 | (1-4-20) | 5% |
| 3-HB—O2 | (13-5) | 15% |
| 5-HB—O2 | (13-5) | 4% |
| 3-H2B(2F,3F)—O2 | (6-4) | 20% |
| 5-H2B(2F,3F)—O2 | (6-4) | 20% |
| 3-HHB(2F,3CL)—O2 | (7-12) | 5% |
| 2-HBB(2F,3F)—O2 | (7-7) | 3% |
| 3-HBB(2F,3F)—O2 | (7-7) | 9% |
| 5-HBB(2F,3F)—O2 | (7-7) | 9% |
| 3-HHB-1 | (14-1) | 3% |
| 3-HHB-3 | (14-1) | 4% |
| 3-HHB—O1 | (14-1) | 3% |

NI=70.8° C.; $\Delta n$=0.105; $\Delta\epsilon$=−5.2; $\eta$=28.3 mPa·s.

Example 13

Use Example 5

| | | |
|---|---|---|
| 2K—B(2CF2H,3F)BH-3 | (1-6-2) | 5% |
| 1-BB-3 | (13-8) | 14% |
| 3-HB—O2 | (13-5) | 7% |
| 5-HB—O2 | (13-5) | 5% |
| 3-BB(2F,3F)—O2 | (6-3) | 9% |
| 5-BB(2F,3F)—O2 | (6-3) | 6% |
| 2-HH1OB(2F,3F)—O2 | (7-5) | 15% |
| 3-HH1OB(2F,3F)—O2 | (7-5) | 20% |
| 5-HBB(2F,3F)—O2 | (7-7) | 9% |
| 3-HHB-1 | (14-1) | 5% |
| 3-HHB—O1 | (14-1) | 3% |
| 2-BBB(2F)-5 | (14-8) | 2% |

NI=85.3° C.; $\Delta n$=0.132; $\Delta\epsilon$=−4.3; $\eta$=30.0 mPa·s.

Example 14

Use Example 6

| | | |
|---|---|---|
| 3-HH1KB(2CF3,3F)—O2 | (1-4-30) | 4% |
| 7-HB-1 | (13-5) | 13% |
| 5-HB—O2 | (13-5) | 11% |
| 3-HB(2F,3F)—O2 | (6-1) | 20% |
| 5-HB(2F,3F)—O2 | (6-1) | 19% |
| 3-HHB(2F,3CL)—O2 | (7-12) | 3% |
| 4-HHB(2F,3CL)—O2 | (7-12) | 3% |

-continued

| | | |
|---|---|---|
| 5-HHB(2F,3CL)—O2 | (7-12) | 2% |
| 3-HH1OCro(7F,8F)-5 | (10-6) | 5% |
| 5-HBB(F)B-2 | (15-5) | 10% |
| 5-HBB(F)B-3 | (15-5) | 10% |

Example 15

Use Example 7

| | | |
|---|---|---|
| 2K—B(2CF3,3F)BH-3 | (1-6-9) | 5% |
| 1-BB-3 | (13-8) | 13% |
| 3-HB—O2 | (13-5) | 4% |
| 5-HB—O2 | (13-5) | 4% |
| 3-BB(2F,3F)—O2 | (6-3) | 18% |
| 2-HH1OB(2F,3F)—O2 | (7-5) | 20% |
| 3-HH1OB(2F,3F)—O2 | (7-5) | 14% |
| 5-HBB(2F,3F)—O2 | (7-7) | 8% |
| 3-HHB-1 | (14-1) | 8% |
| 2-BBB(2F)-5 | (14-8) | 6% |

Example 16

Use Example 8

| | | |
|---|---|---|
| 3-HB1KB(2CF2H,3F)-O2 | (1-4-11) | 5% |
| 3-HB-O1 | (13-5) | 15% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (14-1) | 6% |

Example 17

Use Example 9

| | | |
|---|---|---|
| 3-HB3KB(2CF2H,3F)—O2 | (1-4-21) | 3% |
| 3-H2B(2F,3F)—O2 | (6-4) | 20% |
| 5-H2B(2F,3F)—O2 | (6-4) | 20% |
| 3-HB(2F,3F)—O2 | (6-1) | 9% |
| 2-HHB(2F,3CL)—O2 | (7-12) | 2% |
| 3-HHB(2F,3CL)—O2 | (7-12) | 3% |
| 4-HHB(2F,3CL)—O2 | (7-12) | 2% |
| 5-HHB(2F,3CL)—O2 | (7-12) | 2% |
| 3-HBB(2F,3F)—O2 | (7-7) | 9% |
| 5-HBB(2F,3F)—O2 | (7-7) | 9% |
| V—HHB-1 | (14-1) | 6% |
| 3-HHB-3 | (14-1) | 6% |
| 3-HHEBH-3 | (15-6) | 3% |
| 3-HHEBH-4 | (15-6) | 3% |
| 3-HHEBH-5 | (15-6) | 3% |

Example 18

Use Example 10

| | | |
|---|---|---|
| 2K—B(2CF2H,3F)BB-3 | (1-6-3) | 5% |
| 3-HB—O1 | (13-5) | 15% |

-continued

| | | |
|---|---|---|
| 3-HB(2F,3F)—O2 | (6-1) | 12% |
| 5-HB(2F,3F)—O2 | (6-1) | 12% |
| 2-HHB(2F,3F)-1 | (7-1) | 12% |
| 3-HHB(2F,3F)-1 | (7-1) | 12% |
| 3-HHB(2F,3F)—O2 | (7-1) | 13% |
| 5-HHB(2F,3F)—O2 | (7-1) | 13% |
| 6-HEB(2F,3F)—O2 | (6-6) | 6% |

Example 19

Use Example 11

| | | |
|---|---|---|
| 3-HH1KB(2CF2H,3CF2H)—O2 | (1-4-16) | 5% |
| 3-HB—O2 | (13-5) | 15% |
| 5-HB—O2 | (13-5) | 4% |
| 3-H2B(2F,3F)—O2 | (6-4) | 20% |
| 5-H2B(2F,3F)—O2 | (6-4) | 20% |
| 3-HHB(2F,3CL)—O2 | (7-12) | 5% |
| 2-HBB(2F,3F)—O2 | (7-7) | 3% |
| 3-HBB(2F,3F)—O2 | (7-7) | 9% |
| 5-HBB(2F,3F)—O2 | (7-7) | 9% |
| 3-HHB-1 | (14-1) | 3% |
| 3-HHB-3 | (14-1) | 4% |
| 3-HHB—O1 | (14-1) | 3% |

Example 20

Use Example 12

| | | |
|---|---|---|
| 3-HB1KB(2CF2H,3CF2H)—O2 | (1-4-17) | 5% |
| 1-BB-3 | (13-8) | 14% |
| 3-HB—O2 | (13-5) | 7% |
| 5-HB—O2 | (13-5) | 5% |
| 3-BB(2F,3F)—O2 | (6-3) | 9% |
| 5-BB(2F,3F)—O2 | (6-3) | 6% |
| 2-HH1OB(2F,3F)—O2 | (7-5) | 15% |
| 3-HH1OB(2F,3F)—O2 | (7-5) | 20% |
| 5-HBB(2F,3F)—O2 | (7-7) | 9% |
| 3-HHB-1 | (14-1) | 5% |
| 3-HHB—O1 | (14-1) | 3% |
| 2-BBB(2F)-5 | (14-8) | 2% |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. A liquid crystal composition of the invention contains the compound, and has a high maximum temperature of a nematic phase, a low minimum temperature of the nematic phase, a small viscosity, a suitable optical anisotropy, a large negative dielectric anisotropy and a suitable elastic constant. The composition has a suitable balance regarding at least two of physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a display of a personal computer, a television and so forth.

What is claimed is:

1. A compound represented by any one of formulas (1-21) to (1-27):

wherein, in formulas (1-21) to (1-27),

Ra and Rb are independently alkyl having 1 to 10 carbons, alkenyl having 2 to 10 carbons, alkoxy having 1 to 9 carbons, fluorinated alkyl having 1 to 10 carbons or fluorinated alkoxy having 1 to 9 carbons;

$A^1$ and $A^2$ are independently 1,4-cyclohexylene, 1,4-phenylene, 2-fluoro-1,4-phenylene, 2,3-difluoro-1,4-phenylene, cyclohexene-1,4-diyl or tetrahydropyran-2,5-diyl;

$Z^1$ is independently a single bond, $-(CH_2)_2-$, $-(CH_2)_4-$, $-CH_2O-$, $-OCH_2-$, $-CF_2O-$, $-OCF_2-$, $-CH=CH-$ or $-C\equiv C-$; and $Y^1$ is $-CF_2H$.

2. The compound according to claim 1, wherein, in formulas (1-21) to (1-27) according to claim 1, Ra and Rb are independently alkyl having 1 to 10 carbons, alkenyl having 2 to 10 carbons or alkoxy having 1 to 9 carbons;

$A^1$ and $A^2$ are independently 1,4-cyclohexylene, 1,4-phenylene, 2-fluoro-1,4-phenylene, 2,3-difluoro-1,4-phenylene or tetrahydropyran-2,5-diyl;

$Z^1$ is a single bond; and $Y^1$ is $-CF_2H$.

3. The compound according to claim 1, wherein, in formulas (1-21) to (1-27) according to claim 1, Ra and Rb are independently alkyl having 1 to 10 carbons or alkoxy having 1 to 9 carbons;

$A^1$ and $A^2$ are independently 1,4-cyclohexylene or 1,4-phenylene;

$Z^1$ is a single bond; and $Y^1$ is $CF_2H$.

4. A liquid crystal composition, containing at least one compound according to claim 1.

5. The liquid crystal composition according to claim 4, further containing at least one compound selected from the group of compounds represented by formulas (6) to (12):

-continued

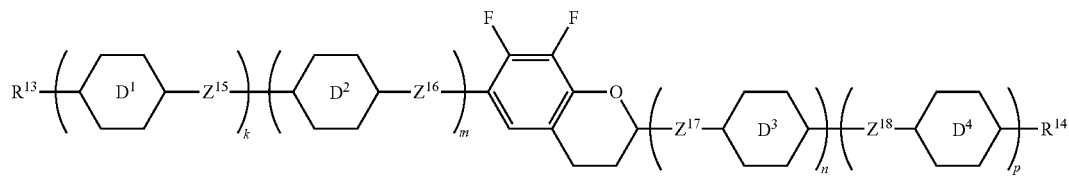
(10)

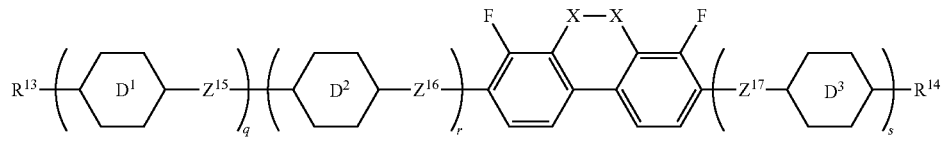
(11)

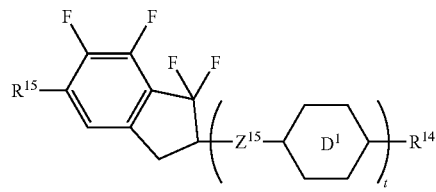
(12)

wherein, in formulas (6) to (12), $R^{13}$ is alkyl having 1 to 10 carbons or alkenyl having 2 to 10 carbons, and in the alkyl and the alkenyl, at least one of —$CH_2$— may be replaced by —O— and at least one of hydrogen may be replaced by fluorine;

$R^{14}$ is alkyl having 1 to 10 carbons, and in the alkyl, at least one of —$CH_2$— may be replaced by —O— and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$S^{11}$ is hydrogen or methyl;

X is —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen is replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

6. The liquid crystal composition according to claim 4, further containing at least one compound selected from the group of compounds represented by formulas (13) to (15):

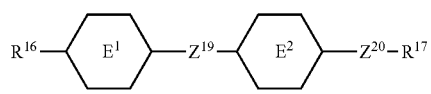
(13)

-continued

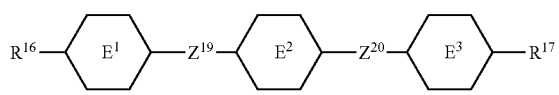
(14)

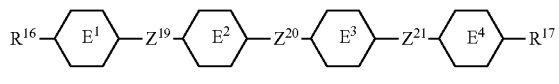
(15)

wherein, in formulas (13) to (15), $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, —C≡C— or —COO—.

7. The liquid crystal composition according to claim 4, further containing at least one compound selected from the group of compounds represented by formulas (2) to (4):

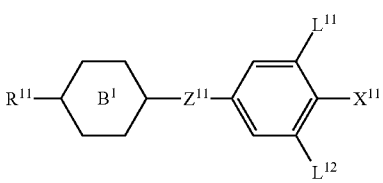
(2)

(3)

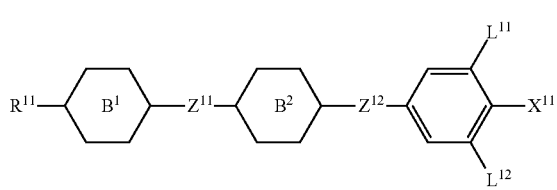

(4)

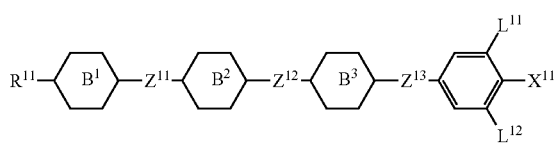

(5)

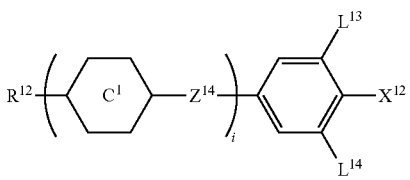

wherein, in formulas (2), (3), and (4)

$R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one of hydrogen is replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —COO—, —$CF_2O$—, —$OCF_2$—, —$CH_2O$— or —$(CH_2)4$-; and $L^{11}$ and $L^{12}$ are independently hydrogen or fluorine.

8. The liquid crystal composition according to claim 4, further containing at least one compound selected from the group of compounds represented by formula (5):

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{12}$ is —C≡N or —C≡C—C≡N;

ring $C^1$ is 1,4-cyclohexylene, 1,4-phenylene in which at least one of hydrogen is replaced by fluorine, tetrahydropyran-2,5-diyl, 1,3-dioxane-2,5-diyl or pyrimidine-2,5-diyl;

$Z^{14}$ is a single bond, —$CH_2CH_2$—, —COO—, —$CF_2O$—, —$OCF_2$— or —$CH_2O$—;

$L^{13}$ and $L^{14}$ are independently hydrogen or fluorine; and i is 1, 2, 3 or 4.

9. The liquid crystal composition according to claim 4, further containing at least one optically active compound and/or at least one polymerizable compound.

10. The liquid crystal composition according to claim 4, further containing at least one antioxidant and/or at least one ultraviolet light absorbent.

11. A liquid crystal display device, including the liquid crystal composition according to claim 4.

* * * * *